US011446613B2

(12) United States Patent
Vail et al.

(10) Patent No.: US 11,446,613 B2
(45) Date of Patent: Sep. 20, 2022

(54) FUNCTIONALIZED COPOLYMERS AND USE THEREOF

(71) Applicant: 3M INNOVATIVE PROPERTIES COMPANY, St. Paul, MN (US)

(72) Inventors: Andrew W. Vail, Bayport, MN (US); Semra Colak Atan, Saint Louis Park, MN (US); Jerald K. Rasmussen, Woodville, WI (US); George W. Griesgraber, Eagan, MN (US); Catherine A. Bothof, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 863 days.

(21) Appl. No.: 16/328,389

(22) PCT Filed: Aug. 30, 2017

(86) PCT No.: PCT/US2017/049365
§ 371 (c)(1),
(2) Date: Feb. 26, 2019

(87) PCT Pub. No.: WO2018/048696
PCT Pub. Date: Mar. 15, 2018

(65) Prior Publication Data
US 2021/0031152 A1 Feb. 4, 2021

Related U.S. Application Data

(60) Provisional application No. 62/385,378, filed on Sep. 9, 2016.

(51) Int. Cl.
| | | |
|---|---|---|
| *B01D 71/00* | (2006.01) | |
| *B01D 69/00* | (2006.01) | |
| *C07K 1/34* | (2006.01) | |
| *B01D 71/40* | (2006.01) | |
| *B01D 69/02* | (2006.01) | |
| *B01D 69/12* | (2006.01) | |
| *B01D 71/78* | (2006.01) | |
| *C07K 16/00* | (2006.01) | |
| *C09D 133/26* | (2006.01) | |
| *B01D 67/00* | (2006.01) | |

(52) U.S. Cl.
CPC ............. *B01D 71/40* (2013.01); *B01D 69/02* (2013.01); *B01D 69/125* (2013.01); *B01D 71/78* (2013.01); *C07K 1/34* (2013.01); *C07K 16/00* (2013.01); *C09D 133/26* (2013.01); *B01D 67/0006* (2013.01); *B01D 2323/385* (2013.01); *B01D 2325/14* (2013.01)

(58) Field of Classification Search
CPC ........ B01D 71/40; B01D 71/78; B01D 69/02; B01D 69/125; C07K 1/34
See application file for complete search history.

(56) References Cited

U.S. PATENT DOCUMENTS

| | | |
|---|---|---|
| 3,876,738 A | 4/1975 | Marinaccio |
| 3,928,517 A | 12/1975 | Knight |
| 4,539,256 A | 9/1985 | Shipman |
| 4,707,265 A | 11/1987 | Barnes, Jr. |
| 4,726,989 A | 2/1988 | Mrozinski |
| 4,867,881 A | 9/1989 | Kinzer |
| 5,120,594 A | 6/1992 | Mrozinski |
| 5,260,360 A | 11/1993 | Mrozinski |
| 5,458,782 A | 10/1995 | Hou |
| 5,506,279 A | 4/1996 | Babu |

(Continued)

FOREIGN PATENT DOCUMENTS

| | | |
|---|---|---|
| JP | S47-040913 | 12/1972 |
| WO | WO 2010-098867 | 9/2010 |

(Continued)

OTHER PUBLICATIONS

Atan, "Novel Ligand Functionalized Membranes for Monoclonal Antibody Purification", Presented at 251$^{st}$ American Chemical Society National Meeting and Exposition, Mar. 2016, 25 pages.

Jain, "High-Capacity Purification of His-tagged Proteins Affinity Membranes Containing Functionalized Polymer Brushes", Biomacromolecule, Oct. 2007, vol. 8, No. 10, pp. 3102-3107.

Mueller, "New Ion Exchangers for The Chromatography of Biopolymers", Journal of Chromatography, Jun. 1990, vol. 510, pp. 133-140.

(Continued)

*Primary Examiner* — Sikarl A Witherspoon
(74) *Attorney, Agent, or Firm* — Jean A. Lown

(57) ABSTRACT

An article that includes a functionalized copolymer and the use thereof, particularly in a process for binding biomaterials, such as in a process for separating aggregated proteins from monomeric proteins in a biological solution; wherein the article includes: a) a porous substrate; and b) a copolymer covalently attached to the porous substrate, the copolymer comprising a hydrocarbon backbone and a plurality of pendant groups attached to the hydrocarbon backbone, wherein 1) each of a first plurality of pendant groups comprises: (a) at least one acidic group or salt thereof; and (b) a spacer group that directly links the at least one acidic group or salt thereof to the hydrocarbon backbone by a chain of at least 6 catenated atoms; and 2) each of a second plurality of pendant groups comprises: (a) at least one acidic group or salt thereof; and (b) a spacer group that directly links the at least one acidic group or salt thereof to the hydrocarbon backbone by a chain of at least 6 catenated atoms; and wherein the first plurality of pendant groups are different than the second plurality of pendant groups; and wherein a mole ratio of the first plurality of pendant groups to the second plurality of pendant groups is in a range of 95:5 to 5:95.

15 Claims, 5 Drawing Sheets

(56) References Cited

U.S. PATENT DOCUMENTS

| | | | |
|---|---|---|---|
| 5,962,544 | A | 10/1999 | Waller, Jr. |
| 6,056,529 | A | 5/2000 | Meyering |
| 6,267,916 | B1 | 7/2001 | Meyering |
| 6,413,070 | B1 | 7/2002 | Meyering |
| 6,776,940 | B2 | 8/2004 | Meyering |
| 7,098,253 | B2 | 8/2006 | Rasmussen |
| 7,125,603 | B2 | 10/2006 | David |
| 7,338,692 | B2 | 3/2008 | Smith |
| 7,674,835 | B2 | 3/2010 | Rasmussen |
| 7,674,836 | B2 | 3/2010 | Rasmussen |
| 7,683,100 | B2 | 3/2010 | Rasmussen |
| 8,277,649 | B2 | 10/2012 | Malenfant |
| 8,530,698 | B2 | 9/2013 | Komiya |
| 8,802,448 | B2 | 8/2014 | Ait-Haddou |
| 2010/0181254 | A1 | 7/2010 | Graalfs |
| 2011/0100916 | A1 | 5/2011 | Shannon |
| 2012/0122759 | A1 | 5/2012 | Brown |
| 2012/0123002 | A1 | 5/2012 | Shinohara |
| 2012/0252091 | A1 | 10/2012 | Rasmussen |
| 2013/0102761 | A1 | 4/2013 | Liao |
| 2013/0245139 | A1 | 9/2013 | Kozlov |
| 2014/0238935 | A1 | 8/2014 | Komkova |
| 2015/0133636 | A1 | 5/2015 | Xenopoulos |
| 2015/0136698 | A1 | 5/2015 | Bothof |

FOREIGN PATENT DOCUMENTS

| | | |
|---|---|---|
| WO | WO 2010-117598 | 10/2010 |
| WO | WO 2013-162449 | 10/2013 |
| WO | WO 2014-052215 | 4/2014 |
| WO | WO 2014-077762 | 5/2014 |
| WO | WO 2015-050767 | 4/2015 |
| WO | WO 2015-088677 | 6/2015 |
| WO | WO 2016-073565 | 5/2016 |
| WO | WO 2018-048698 | 3/2018 |

OTHER PUBLICATIONS

Rasmussen, "Evaluation of Ligand Design for Downstream Processes: Application to Aggregate Removal", Presented at $251^{st}$ American Chemical Society National Meeting and Exposition, Mar. 2016, 19 pages.

Tauzin, "Variable Surface Transport Modalities on Functionalized Nylon Films Revealed with Single Molecule Spectroscopy", RSC Advances vol. 6 No. 33, Mar. 2016, 23 pages.

Wente, "Manufacture of Superfine Organic Fibers", Naval Research Laboratories Report No. 4364, May 1954, 19 pages.

Wente, "Superfine Thermoplastic Fibers," Industrial Engineering Chemistry, Aug. 1956, vol. 48, No. 8, pp. 1342-1346.

Willson, "Enhanced Protein Affinity and Selectivity of Clustered-Charge Anion-Exchange Adsorbents", Analytical Chemistry, Nov. 2007, vol. 79 No. 23, pp. 9060-9065.

Willson, "Nucleic Acid Affinity of Clustered-Charge Anion Exchange Adsorbents: Effects of Ionic Strength and Ligand Density", Journal of Chromatography A, 2011, vol. 1218, pp. 258-262.

Willson, "Spermine Sepharose as a Clustered-Charge Anion Exchange Adsorbent", Journal of Chromatography A, 2014, vol. 1324, pp. 135-140.

International Search Report for PCT International Application No. PCT/US2017/049365, dated Nov. 29, 2017, 5 pages.

International Search Report for PCT International Application No. PCT/US2017/049376, dated May 1, 2018, 4 pages.

US 11,446,613 B2

FUNCTIONALIZED COPOLYMERS AND USE THEREOF

CROSS REFERENCE TO RELATED APPLICATIONS

This application is a national stage filing under 35 U.S.C. 371 of PCT/US2017/049365, filed Aug. 30, 2017, which claims the benefit of U.S. Provisional Application No. 62/385,378, filed Sep. 9, 2016, the disclosure of which is incorporated by reference in its/their entirety herein.

BACKGROUND

Detection, quantification, isolation, and purification of target biomaterials, such as biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases.

Isolation and purification of target biomaterials, particularly monomeric proteins, such as monomeric antibodies (particularly monomeric monoclonal antibodies) are important for therapeutic uses for a variety of diseases including rheumatoid arthritis, Crohn's disease, hypercholesterolemia, and a variety of cancers. Monoclonal antibodies, for example, are preferred over conventional therapies because they can be directed to specific targets without significant adverse effect on healthy tissue. Removal of aggregated proteins from the monomeric proteins is particularly important for such therapeutic uses.

Polymeric materials have been widely used for the separation and purification of various target biomaterials. Such separation and purification methods can be based on any of a number of binding factors or mechanisms including the presence of an ionic group, the size of the target biomaterial, a hydrophobic interaction, an affinity interaction, a hydrogen bonding interaction, the formation of a covalent bond, and so forth.

Membrane-based technologies, especially in disposable format, are becoming increasingly important in biopharmaceutical and vaccine manufacturing processes. Membranes have been used in passive, size-based separations, and, more recently, in active filtration (for example, for the removal of minor contaminants in later stages of purification processes).

Functionalized membranes (including functional polymer-bearing membranes) have typically suffered from relatively low biomaterial binding capacities, however, and this has generally limited their use in large-scale purifications. Porous beaded chromatography resins (bearing ion exchange or other interactive functional groups), rather than functionalized membranes, therefore have been standardly used in "capture-and-elute" or "bind-and-elute" type protein purification processes.

Thus, there is a need for articles and their use in processes that are relatively simple, cost-effective, and/or efficient for isolation and purification of biomolecules, such as in a process that separates aggregated proteins from monomeric proteins, particularly monomeric monoclonal antibodies.

SUMMARY

The present disclosure provides functionalized substrates (particularly, functionalized membranes) having relatively high biomaterial binding capacities. Such materials can be used in processes that are relatively simple, cost-effective, and/or efficient (for example, involving relatively easily accessible starting materials and/or relatively few process steps) for isolation and purification of biomolecules.

The present disclosure provides an article that includes a functionalized copolymer and the use thereof, particularly in a process for binding biomaterials, such as in a process for separating aggregated proteins from monomeric proteins in a biological solution.

In one aspect of the disclosure, an article is provided that includes:
   a) a porous substrate; and
   b) a copolymer covalently attached to the porous substrate, the copolymer including a hydrocarbon backbone and a plurality of pendant groups attached to the hydrocarbon backbone, wherein:
      1) each of a first plurality of pendant groups includes:
         (a) at least one acidic group or salt thereof; and
         (b) a spacer group that directly links the at least one acidic group or salt thereof to the hydrocarbon backbone by a chain of at least 6 catenated atoms; and
      2) each of a second plurality of pendant groups includes:
         (a) at least one acidic group or salt thereof; and
         (b) a spacer group that directly links the at least one acidic group or salt thereof to the hydrocarbon backbone by a chain of at least 6 catenated atoms; and
      wherein the first plurality of pendant groups are different than the second plurality of pendant groups; and
      wherein a mole ratio of the first plurality of pendant groups to the second plurality of pendant groups is in a range of 95:5 to 5:95.

In another aspect of the disclosure, an article is provided that includes:
   a) a porous substrate; and
   b) a copolymer covalently attached to the porous substrate, the copolymer including a reaction product of a monomer composition that includes:
      1) a first monomer including:
         (a) at least one ethylenically unsaturated group;
         (b) at least one acidic group or salt thereof; and
         (c) a spacer group that directly links the at least one ethylenically unsaturated group and the at least one acidic group or salt thereof by a chain of at least 6 catenated atoms; and
      2) a second monomer including:
         (a) at least one ethylenically unsaturated group;
         (b) at least one acidic group or salt thereof; and
         (c) a spacer group that directly links the at least one ethylenically unsaturated group and the at least one acidic group or salt thereof by a chain of at least 6 catenated atoms;
      wherein the second monomer is different than the first monomer; and
      wherein a mole ratio of the first monomer to the second monomer is in a range of 95:5 to 5:95.

In another aspect, the article is a filter element having a contacting surface (e.g., an upstream or upper surface), and in another aspect, the article is an array of sample containers (e.g., a 96-well plate) with each container including a filter element.

In another aspect of the disclosure, a process for capture or removal of a target biomaterial is provided. The process includes: providing a filter element or an array of sample containers of the present disclosure; and allowing a biological solution including a target biomaterial to contact the contacting surface (e.g., upstream or upper surface) of the filter element under conditions effective for binding of the target biomaterial.

Such target biomaterial may include proteins, such as antibodies. In certain processes of the present disclosure, the target biomaterial includes aggregated proteins (in particular, antibodies), which results in purification of monomeric proteins (in particular, antibodies).

Thus, in another aspect of the disclosure, a process is provided that results in the separation of aggregated antibodies from monomeric antibodies. The process involves allowing a biological solution that includes aggregated antibodies (the target biomaterial) and monomeric antibodies, to contact the contacting surface (e.g., upstream or upper surface) of the filter element under conditions effective for binding the aggregated antibodies and passage of the monomeric antibodies.

In a more specific aspect of the disclosure, the process includes: providing at least one filter element having a contacting surface (e.g., an upstream or upper surface), wherein the filter element includes filter media as described herein; and allowing an initial biological solution to contact the contacting surface (e.g., the upstream or upper surface) of the filter element under conditions effective to separate the aggregated proteins (e.g., antibodies) from the monomeric proteins (e.g., antibodies) such that a final biological solution includes purified monomeric proteins.

Definitions

As used in this patent application:

"aggregated protein" or "protein aggregate" refers to an association of at least two molecules (i.e., monomers) of a product of interest, e.g., a therapeutic protein (e.g., antibody). The association of at least two molecules of a product of interest may arise by any means including, but not limited to, covalent, non-covalent, disulfide, or non-reducible cross-linking;

"boronato" means a group of formula —B(OH)$_2$;

"carbonylimino" means a divalent group or moiety of formula —(CO)NR—, where R is hydrogen, alkyl (for example, selected from alkyl groups having from one to four carbon atoms), or aryl (preferably, R is hydrogen);

"carboxy" means a group of formula —COOH;

"catenated atom" means an in-chain atom (rather than an atom of a chain substituent);

"catenated heteroatom" means an atom other than carbon (for example, oxygen, nitrogen, or sulfur) that replaces one or more carbon atoms in a carbon chain (for example, so as to form a carbon-heteroatom-carbon chain or a carbon-heteroatom-heteroatom-carbon chain);

"ethylenically unsaturated" means a group of formula —CY=CH$_2$ where Y is hydrogen, alkyl, cycloalkyl, or aryl;

"graft density" was determined by measuring the mass gain after conversion of the substrate to the finished filter element, divided by the theoretical molecular weight of the monomer mixture used, and expressed as mmol/g, that is, millimoles (or milliequivalents) of ligand group grafted per gram of original substrate;

"heteroatom" means an atom other than carbon or hydrogen;

"hydrogen bond acceptor" means a heteroatom selected from oxygen, nitrogen, and sulfur that has a lone electron pair;

"hydrogen bond donor" means a moiety consisting of a hydrogen atom covalently bonded to a heteroatom selected from oxygen, nitrogen, and sulfur;

"hydrogen bonding moiety" means a moiety that includes at least one hydrogen bond donor and at least one hydrogen bond acceptor;

"hydroxy" means a group of formula —OH;

"iminocarbonylimino" means a divalent group or moiety of formula —N(R)—C(O)—N(R)—, wherein each R is independently hydrogen, alkyl (for example, selected from alkyl groups having from one to four carbon atoms), or aryl (preferably, at least one R is hydrogen; more preferably, both are hydrogen);

"iminothiocarbonylimino" means a divalent group or moiety of formula —N(R)—C(S)—N(R)—, wherein each R is independently hydrogen, alkyl (for example, selected from alkyl groups having from one to four carbon atoms), or aryl (preferably, at least one R is hydrogen; more preferably, both are hydrogen);

"isocyanato" means a group of formula —N=C=O;

"oxycarbonylimino" means a divalent group or moiety of formula —O—C(O)—N(R)—, wherein R is hydrogen, alkyl (for example, selected from alkyl groups having from one to four carbon atoms), or aryl (preferably, R is hydrogen);

"oxythiocarbonylimino" means a divalent group or moiety of formula —O—C(S)—N(R)—, wherein R is hydrogen, alkyl (for example, selected from alkyl groups having from one to four carbon atoms), or aryl (preferably, R is hydrogen);

"phosphato" means a group of formula —OPO$_3$H$_2$;

"phosphono" means a group of formula —PO$_3$H$_2$ wherein this group is not attached to another oxygen atom;

"purified" in the context of monomeric proteins (e.g., antibodies) in a biological solution means that the amount of monomeric proteins (e.g., antibodies) relative to the amount of aggregated proteins (e.g., antibodies) in the final biological solution compared to the initial biological solution is increased;

"sulfato" means a group of formula —OSO$_3$H;

"sulfono" means a group of formula —SO$_3$H wherein this group is not attached to another oxygen atom;

"thiocarbonylimino" means a divalent group or moiety of formula —(CS)NR—, where R is hydrogen, alkyl (for example, selected from alkyl groups having from one to four carbon atoms), or aryl (preferably, R is hydrogen).

Also, herein, the terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements (e.g., preventing and/or treating an affliction means preventing, treating, or both treating and preventing further afflictions).

Herein, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

When a group is present more than once in a formula described herein, each group is "independently" selected, whether specifically stated or not. For example, when more than one $R^2$ group is present in a formula, each $R^2$ group is independently selected. Furthermore, subgroups contained within these groups are also independently selected.

The above Summary section is not intended to describe every embodiment or every implementation of the disclosure. The detailed description that follows more particularly describes illustrative embodiments. Throughout the detailed description, guidance is provided through lists of examples, which examples can be used in various combinations. In each instance, a recited list serves only as a representative group and should not be interpreted as being an exclusive list.

DETAILED DESCRIPTION

Figure 1A:
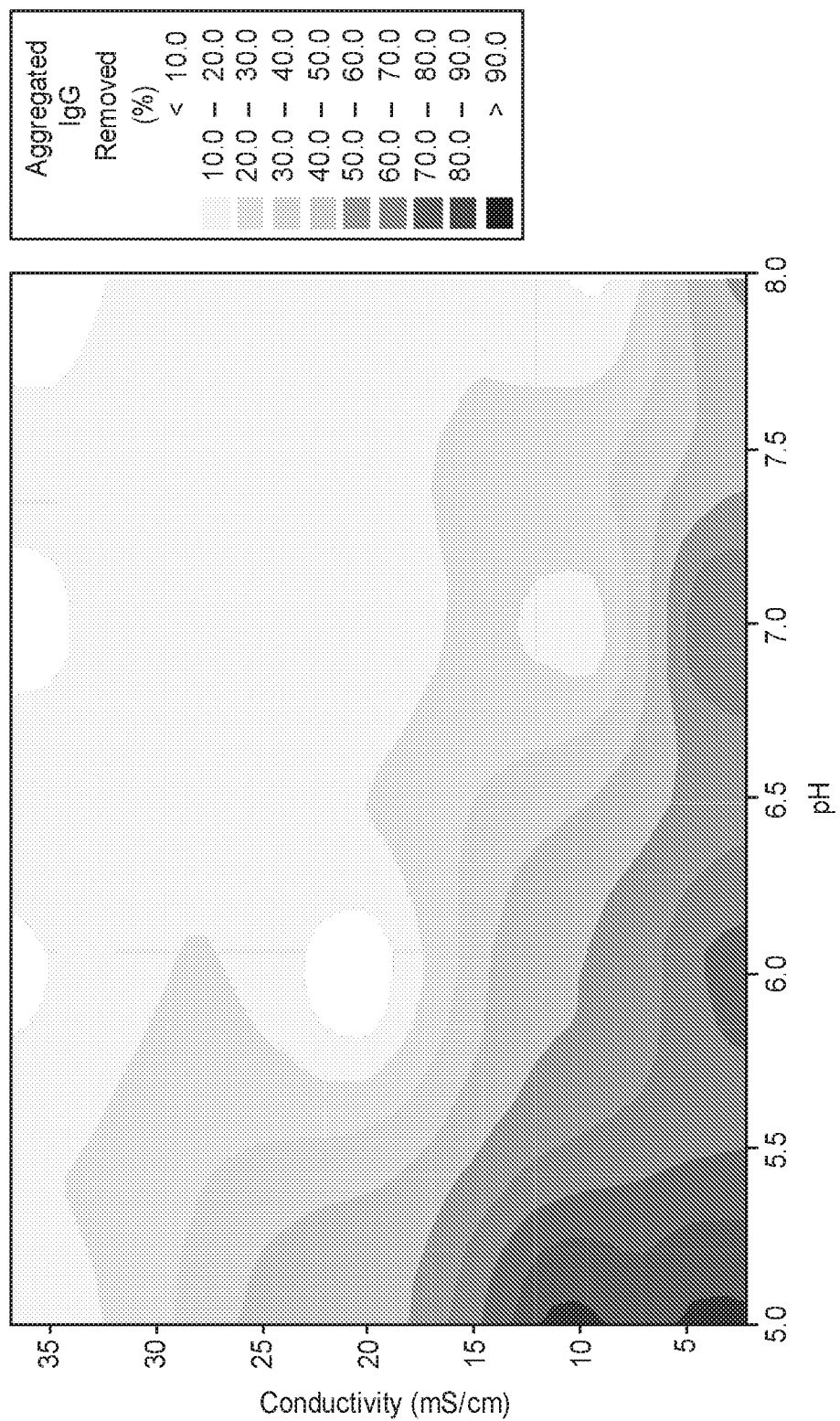
FIG. 1A-1E depict contour plots indicating optimal regions of operation (shown in dark colors) for removal of aggregated IgG at a 386 g/L IgG loading with Comparative Example A (VDM-GABA, FIG. 1A), Example 6 (90:10 of VDM-GABA:VDM-phenylalanine, FIG. 1B), Example 4 (75:25 of VDM-GABA:VDM-phenylalanine, FIG. 1C), Example 5 (50:50 of VDM-GABA:VDM-phenylalanine, FIG. 1D), and Comparative Example D (VDM-phenylalanine, FIG. 1E). Contour plots were generated by Minitab 17 Statistical Software.

The present disclosure provides an article that includes a functionalized copolymer and the use thereof, particularly in a process for binding biomaterials, such as in a process for separating aggregated proteins from monomeric proteins in a biological solution.

The article includes:
a) a porous substrate; and
b) a copolymer covalently attached to the porous substrate, the copolymer including a hydrocarbon backbone and a plurality of pendant groups attached to the hydrocarbon backbone, wherein:
  1) each of a first plurality of pendant groups includes:
    (a) at least one acidic group or salt thereof; and
    (b) a spacer group that directly links the at least one acidic group or salt thereof to the hydrocarbon backbone by a chain of at least 6 catenated atoms; and
  2) each of a second plurality of pendant groups includes:
    (a) at least one acidic group or salt thereof; and
    (b) a spacer group that directly links the at least one acidic group or salt thereof to the hydrocarbon backbone by a chain of at least 6 catenated atoms; and
  wherein the first plurality of pendant groups are different than the second plurality of pendant groups; and
  wherein a mole ratio of the first plurality of pendant groups to the second plurality of pendant groups is in a range of 95:5 to 5:95.

The copolymer disposed on the porous substrate can be formed in a variety of ways. In certain embodiments, a copolymer can be formed from monomers in the presence of the substrate and grafted thereto. For example, monomers that include the acidic group or salt thereof can be subjected to electron beam radiation in the presence of the substrate to graft and polymerize such monomers. In another embodiment, compounds that include the acidic group or salt thereof can be reacted with monomer units previously grafted to the substrate surface.

In certain embodiments, the copolymer attached to the porous substrate includes a reaction product of a monomer composition that includes:
1) a first monomer comprising (in some embodiments, consisting of):
  (a) at least one ethylenically unsaturated group (in some embodiments, a terminal ethylenically unsaturated group);
  (b) at least one acidic group or salt thereof; and
  (c) a spacer group that directly links the at least one ethylenically unsaturated group and the at least one acidic group or salt thereof by a chain of at least 6 catenated atoms; and
2) a second monomer comprising (in some embodiments, consisting of):
  (a) at least one ethylenically unsaturated group (in some embodiments, a terminal ethylenically unsaturated group);

(b) at least one acidic group or salt thereof; and (c) a spacer group that directly links the at least one ethylenically unsaturated group and the at least one acidic group or salt thereof by a chain of at least 6 catenated atoms;

wherein the second monomer is different than the first monomer; and wherein a mole ratio of the first monomer to the second monomer is in a range of 95:5 to 5:95.

In certain embodiments, the acidic groups or salts thereof in the first and/or second plurality of pendant groups of the copolymer or in the first and/or second monomers are selected from carboxy, phosphono, phosphato, sulfono, sulfato, boronato, and combinations thereof.

In certain embodiments, the spacer group in the first and/or second plurality of pendant groups of the copolymer or in the first and/or second monomers includes at least one hydrogen bonding moiety.

Surprisingly, the acidic groups or salts thereof of such copolymers can be especially effective in interacting with target biomaterials (e.g., aggregated proteins relative to monomeric proteins). Porous substrates having the copolymer covalently bonded thereto can exhibit unexpectedly higher biomaterial binding capacities than corresponding porous substrates bearing copolymers with a shorter linking chain. Biomaterial binding capacities can be surprisingly further enhanced by including at least one hydrogen bonding moiety in the linking chain.

Figure 1B:
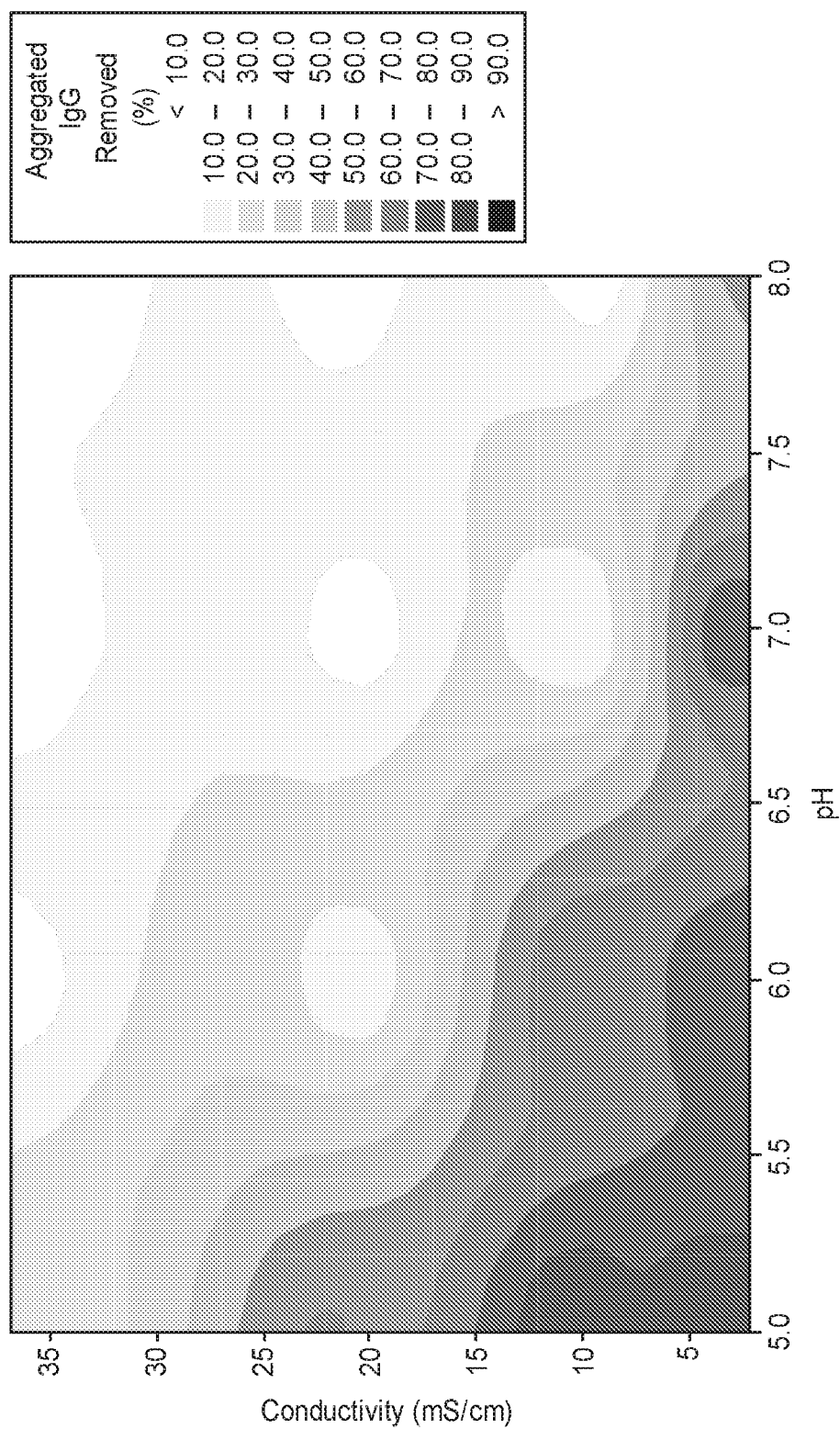
Figure 1C:
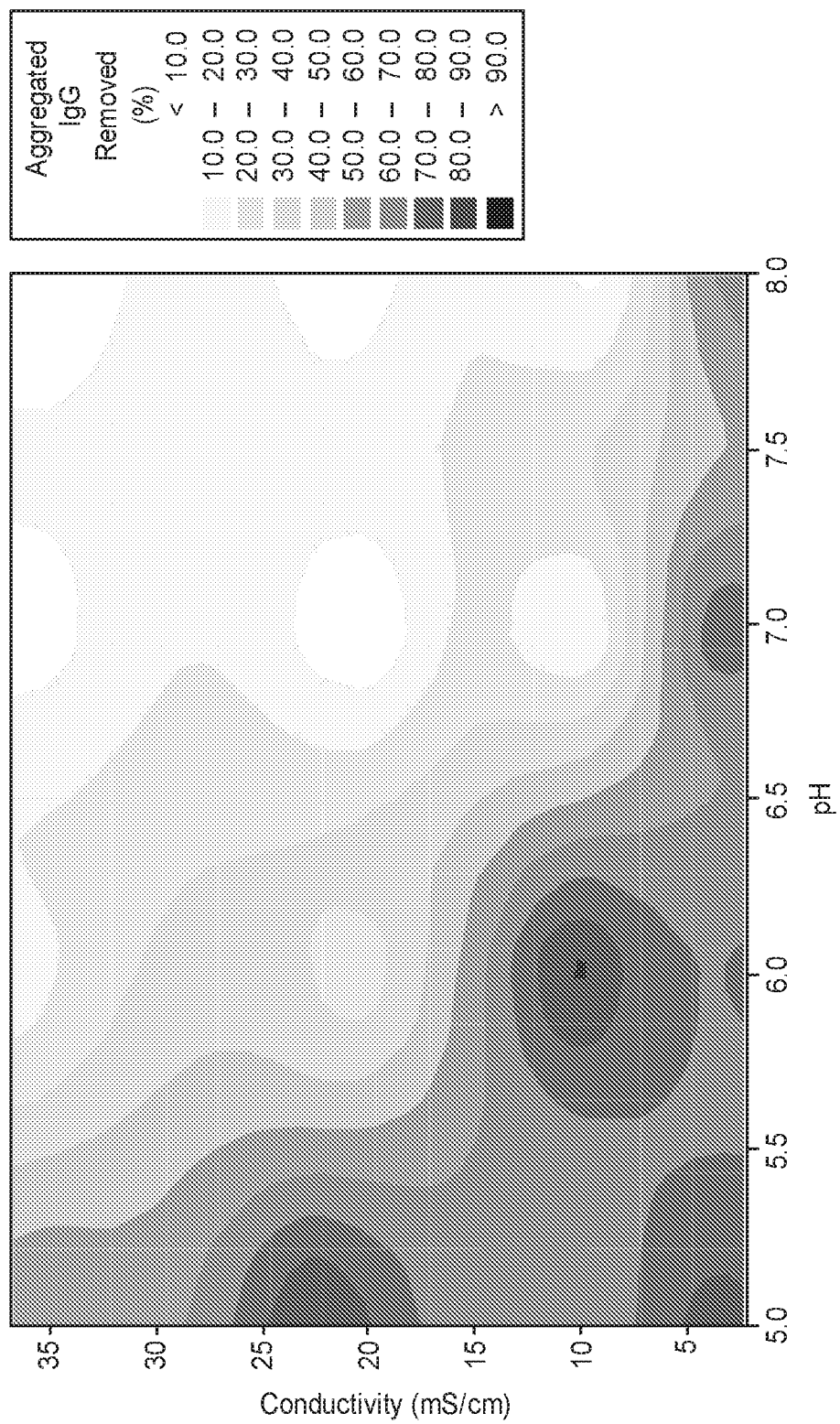
Figure 1D:
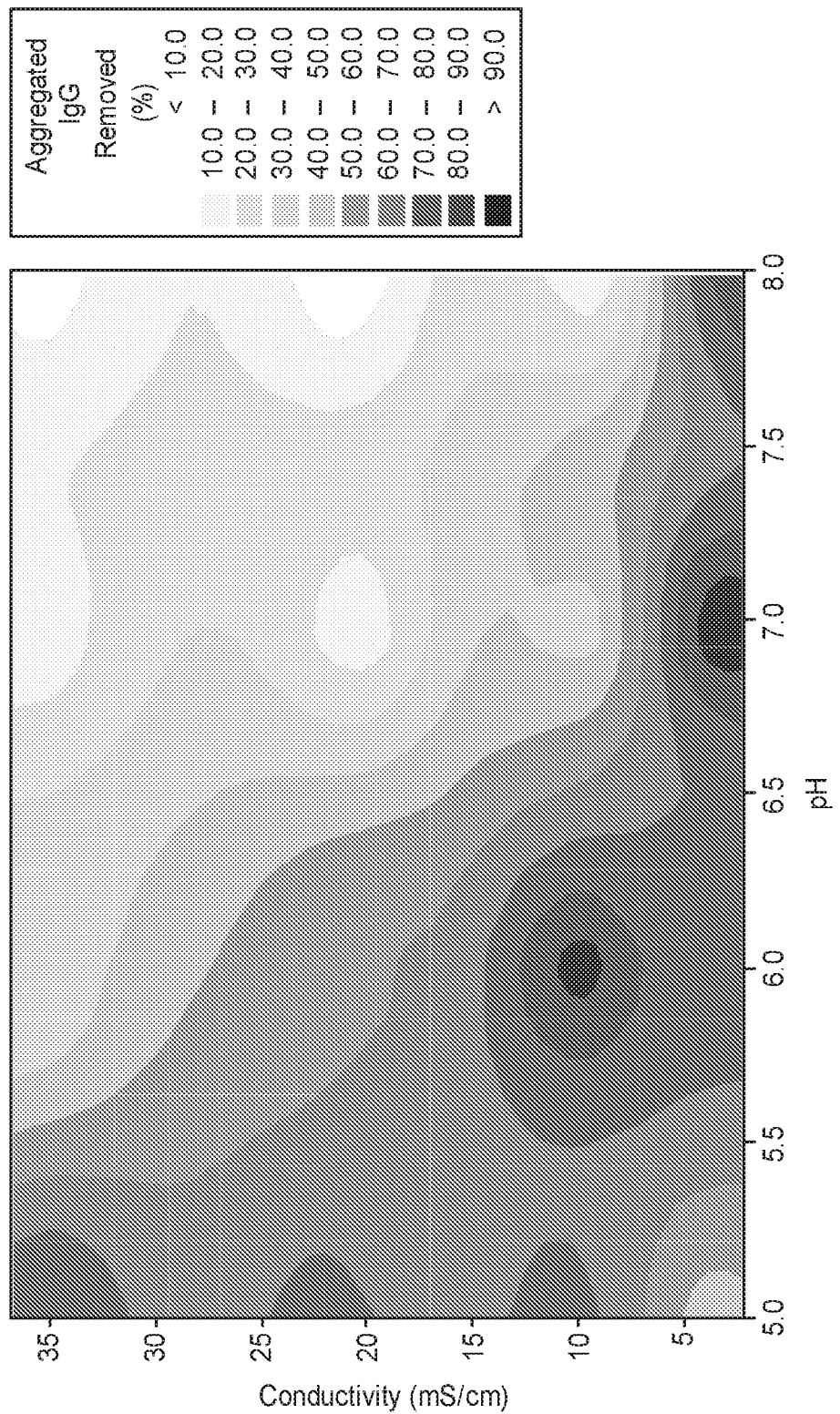
Figure 1E:
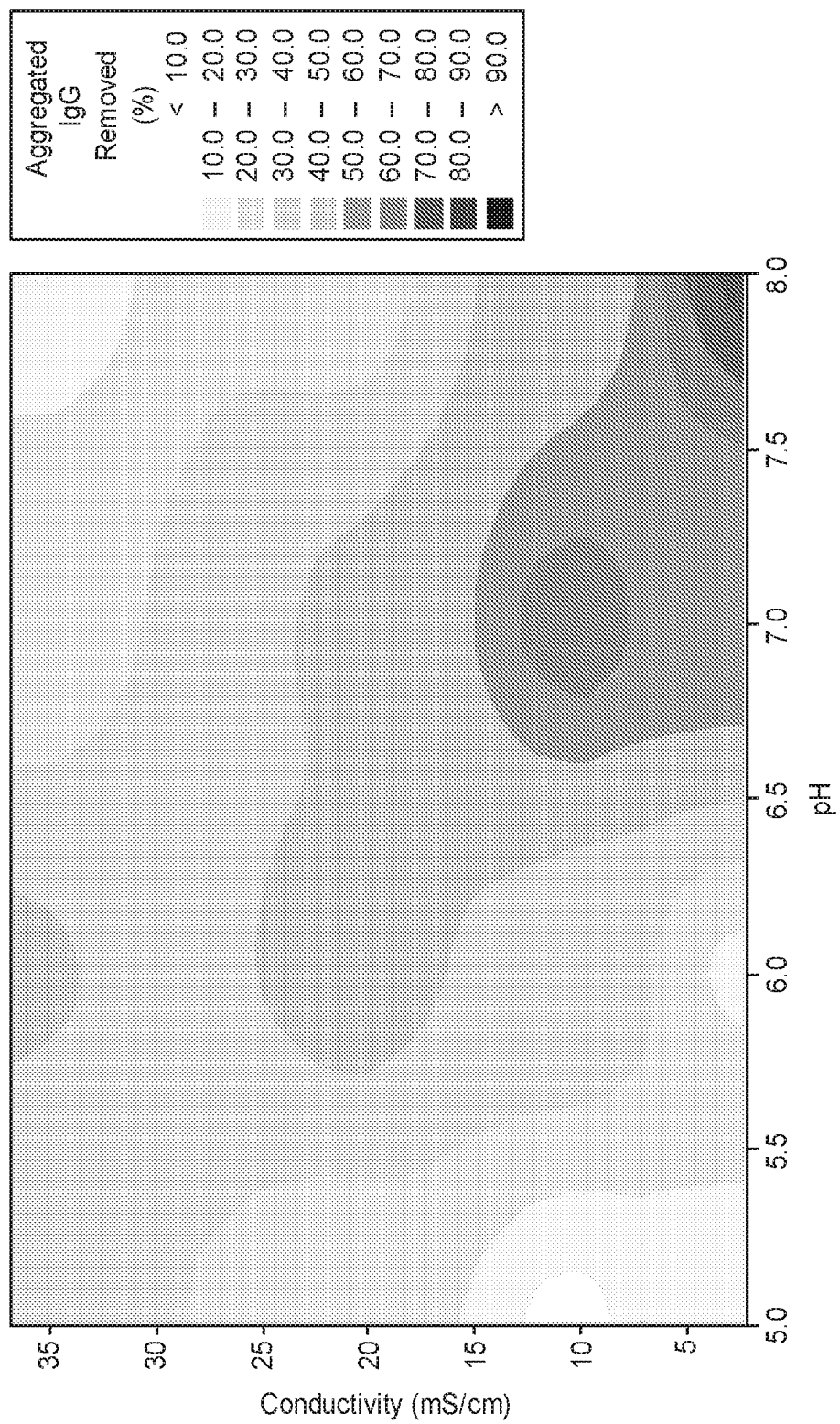

FIGS. 1A-1E depict contour plots indicating optimal regions of operation (shown in dark colors) for removal of aggregated IgG. These copolymer filter elements show an advantage over homopolymer filter elements by the expansion of the conductivity and pH operating range for aggregate removal when increasing the amount of second monomer containing a different spacer moiety. These copolymer filter elements allow efficient aggregate removal in conductivity and pH ranges unavailable with homopolymer filter elements.

In certain embodiments, the relatively high binding capacity functionalized substrates for binding to target biomaterials (e.g., aggregated proteins relative to monomeric proteins), can be prepared by using certain monomers having a multi-atom spacer group between the monomer's ethylenically unsaturated group and acidic group or salt thereof. The at least two different monomers include compounds in which at least one acidic group or salt thereof is separated or spaced from at least one ethylenically unsaturated group by a linking chain of at least six catenated atoms. When free radically polymerized, such monomers provide copolymers bearing acidic groups or salts thereof that are separated or spaced from the resulting polymer chain or copolymer backbone by the linking chain of at least six (6) catenated atoms.

Monomers

A copolymer of the present disclosure includes a hydrocarbon backbone, a first plurality of pendant groups attached to the hydrocarbon backbone, a second plurality of pendant groups attached to the hydrocarbon backbone; wherein the first plurality of pendant groups are different than the second plurality of pendant groups. The copolymers include a mole ratio of the first plurality of pendant groups to the second plurality of pendant groups in a range of 95:5 to 5:95, or in a range of 90:10 to 10:90, or in a range of 85:15 to 15:85, or in a range of 80:20 to 20:80, or in a range of 75:25 to 25:75, or, for example, at a ratio of 50:50.

Monomers suitable for use in preparing such copolymers and articles (e.g., filter media) of the present disclosure include those that comprise (or consist of): (a) at least one ethylenically unsaturated group; (b) at least one acidic group or salt thereof; and (c) a spacer group that directly links the at least one ethylenically unsaturated group and the at least one acidic group or salt thereof by a chain of at least 6 catenated atoms. The copolymers can be made from two different monomers of this class that are different and copolymerized in amounts such that the mole ratio of the two monomers (i.e., the first monomer to the second monomer) is in a range of 95:5 to 5:95. In certain embodiments, mole ratio of the two monomers (i.e., the first monomer to the second monomer) is in a range of 90:10 to 10:90, or in a range of 85:15 to 15:85, or in a range of 80:20 to 20:80, or in a range of 75:25 to 25:75, or, for example, at a ratio of 50:50.

The monomers can be in a neutral state but can also be negatively charged under some pH conditions.

The ethylenically unsaturated group (as defined above) of the monomer(s) can be represented by the formula —CY=CH$_2$, wherein Y is hydrogen, alkyl, cycloalkyl, or aryl. In certain embodiments, ethylenically unsaturated groups include ethenyl, 1-alkylethenyl, and combinations thereof (that is, Y is preferably hydrogen or alkyl; more preferably, Y is hydrogen or $C_1$ to $C_4$ alkyl; and even more preferably, Y is hydrogen or methyl).

The monomer(s) can include a single ethylenically unsaturated group or multiple ethylenically unsaturated groups (for example, two or three or up to as many as 6), which can be the same or different in nature (preferably, the same). The monomer(s) preferably have only one ethylenically unsaturated group.

Suitable acidic groups of the monomers include those that exhibit at least a degree of acidity (which can range from relatively weak to relatively strong), as well as salts thereof. Such acidic groups or salts thereof include those commonly utilized as ion exchange or metal chelate type ligands.

In certain embodiments, the at least one acidic group or salt thereof is a heteroatom-containing group. Useful acidic groups include heterohydrocarbyl groups and other heteroatom-containing groups. For example, useful acidic groups can include one or more heteroatoms selected from oxygen, sulfur, phosphorus, boron, and the like, and combinations thereof. Useful salts of acidic groups include those having counter ions selected from alkali metal (for example, sodium or potassium), alkaline earth metal (for example, magnesium or calcium), ammonium, and tetraalkylammonium ions, and the like, and combinations thereof.

The monomer(s) can include a single acidic group or multiple acidic groups (for example, two or three or up to as many as 6), or salts thereof, which can be the same or different in nature (preferably, the same). In certain embodiments, the acidic group(s) are selected from carboxy, phosphono, phosphato, sulfono, sulfato, boronato, and combinations thereof. In certain embodiments, the acidic group(s) include carboxy, phosphono, sulfono, and combinations thereof. In certain embodiments, the acidic group is a carboxy group.

The spacer group of the monomer(s) can be directly linked to at least one ethylenically unsaturated group and at least one acidic group or salt thereof by a chain of at least 6 catenated atoms. Thus, the chain can include 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more catenated atoms (for example, including up to as many as 40 or 50). In certain embodiments, the chain includes at least 7 catenated atoms (more preferably, at least 8, and even more preferably, at least 9, at least 10, at least 11, or at least 12 catenated atoms)

and/or includes no more than 30 catenated atoms (more preferably, no more than 25, even more preferably, no more than 20, and even more preferably, no more than 16 catenated atoms).

Although not wishing to be bound by theory, the length of the chain may contribute to adoption of helical or partially helical conformations by the polymer backbone (formed through monomer polymerization). When the chain is relatively short (for example, less than 6 catenated atoms), ionic repulsion between acidic groups may force the polymer backbone into a random coil type conformation. As chain length increases, adoption of helical conformations may become possible and may be maximized at chain lengths of 8 to 14 catenated atoms. A helical conformation of substrate-grafted polymer may facilitate presentation of the acidic group(s), or salt(s) thereof, for interaction with a target biomaterial (e.g., aggregated proteins, particularly aggregated monoclonal antibodies).

In certain embodiments, spacer groups include at least one hydrogen bonding moiety, which is defined above as a moiety including at least one hydrogen bond donor and at least one hydrogen bond acceptor (both of which are heteroatom-containing). Thus, preferred spacer groups include heteroatom-containing hydrocarbon groups (more preferably, catenated heteroatom-containing hydrocarbon groups). More preferred spacer groups include at least two hydrogen bonding moieties or include at least one hydrogen bonding moiety and at least one hydrogen bond acceptor that is distinct from (not part of) the hydrogen bonding moiety.

In certain embodiments, hydrogen bonding moieties include those that include at least two hydrogen bond donors (for example, donors such as imino, thio, or hydroxy), at least two hydrogen bond acceptors (for example, acceptors in the form of carbonyl, carbonyloxy, or ether oxygen), or both. For example, an iminocarbonylimino moiety (having two N—H donors and at least two acceptors in the form of two lone electron pairs on carbonyl) can sometimes be preferred over a single iminocarbonyl moiety. In certain embodiments, the spacer groups include those that include at least one iminocarbonylimino moiety (more preferably, in combination with at least one acceptor such as carbonyloxy), at least two iminocarbonyl moieties, or a combination thereof.

The hydrogen bond donor and hydrogen bond acceptor of the hydrogen bonding moiety can be adjacent (directly bonded) to each other or can be non-adjacent (preferably, adjacent or separated by a chain of no more than 4 catenated atoms; more preferably, adjacent). The heteroatoms of the hydrogen bond donor and/or hydrogen bond acceptor can be located in the chain of catenated atoms of the spacer group or, alternatively, can be located in chain substituents.

Although hydrogen bond donors can also function as hydrogen bond acceptors (through a lone electron pair of the donor's heteroatom), the hydrogen bonding moiety preferably includes distinct donor and acceptor moieties. This can facilitate intramolecular (intermonomer) hydrogen bond formation. Although not wishing to be bound by theory, such intramolecular hydrogen bonds between adjacent monomer or near neighbor repeat units in the polymer molecule may contribute to at least a degree of spacer group stiffening, which may facilitate presentation of the acidic group(s) or salt(s) thereof for interaction with a target biomaterial (e.g., aggregated proteins, particularly aggregated monoclonal antibodies).

Surprisingly, the acidic groups or salts thereof of such copolymers can be especially effective in interacting with aggregated proteins, relative to monomeric proteins. Aggregated protein binding capacities can be surprisingly further enhanced by including at least one hydrogen bonding moiety in the linking chain of the monomer.

In certain embodiments, hydrogen bonding moieties include carbonylimino, thiocarbonylimino, iminocarbonylimino, iminothiocarbonylimino, oxycarbonylimino, oxythiocarbonylimino, and the like, and combinations thereof. In certain embodiments, hydrogen bonding moieties include carbonylimino, iminocarbonylimino, oxycarbonylimino, and combinations thereof (more preferably, carbonylimino, iminocarbonylimino, and combinations thereof). In certain embodiments, spacer groups include those that are divalent, trivalent, or tetravalent (more preferably, divalent or trivalent; and even more preferably, divalent).

A class of useful monomers includes those represented by the following general Formula I:

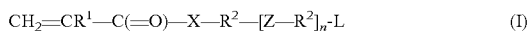

wherein:
$R^1$ is selected from hydrogen, alkyl, cycloalkyl, aryl, and combinations thereof;
each $R^2$ is independently selected from hydrocarbylene, heterohydrocarbylene, and combinations thereof;
X is —O— or —NR$^3$—, where $R^3$ is selected from hydrogen, hydrocarbyl, heterohydrocarbyl, and combinations thereof;
Z is heterohydrocarbylene including at least one hydrogen bond donor, at least one hydrogen bond acceptor, or a combination thereof;
n is an integer of 0 or 1; and
L is a functional group including at least one acidic group or salt thereof.

In certain embodiments of Formula I, $R^1$ is hydrogen or alkyl (more preferably, hydrogen or $C_1$ to $C_4$ alkyl; and even more preferably, hydrogen or methyl).

In certain embodiments, each $R^2$ is independently hydrocarbylene or heterohydrocarbylene. In certain embodiments, each $R^2$ is independently aralkylene (i.e., an alkylene substituted with an aryl), heteroaralkylene, hydroxy-substituted alkylene, or a hydroxy-substituted aralkylene. In certain embodiments, each $R^2$ is independently hydrocarbylene. In certain embodiments, each $R^2$ is independently alkylene).

In certain embodiments, X is —O— or —NR$^3$—, where $R^3$ is hydrogen.

In certain embodiments, Z is heterohydrocarbylene including at least one moiety selected from carbonyl, carbonylimino, carbonyloxy, ether oxygen, thiocarbonylimino, iminocarbonylimino, iminothiocarbonylimino, oxycarbonylimino, oxythiocarbonylimino, and combinations thereof (more preferably, selected from carbonyl, carbonylimino, carbonyloxy, ether oxygen, iminocarbonylimino, oxycarbonylimino, and combinations thereof; even more preferably, selected from carbonylimino, carbonyloxy, ether oxygen, iminocarbonylimino, and combinations thereof; and even more preferably, selected from carbonylimino, iminocarbonylimino, and combinations thereof).

In certain embodiments, n is an integer of 1.
In certain embodiments, L is a functional group including at least one acidic group or salt thereof selected from carboxy, phosphono, phosphato, sulfono, sulfato, boronato, and combinations thereof (more preferably, selected from carboxy, phosphono, sulfono, and combinations thereof).

Such monomers can be prepared by known synthetic methods or by analogy to known synthetic methods. For example, amino group-containing carboxylic, sulfonic, or phosphonic acids can be reacted with ethylenically unsaturated compounds that include at least one group that is reactive with an amino group. Similarly, acidic group-containing compounds that also contain a hydroxy group can be reacted with ethylenically unsaturated compounds that include at least one group that is reactive with a hydroxy group, optionally in the presence of a catalyst.

Preferred monomers are (meth)acryloyl-functional. As used herein, the term "(meth)acryloyl-functional" refers to acryloyl-functional and/or methacryloyl-functional; similarly, the term "(meth)acrylate" refers to an acrylate and/or a methacrylate. In such monomers, the carbonyl group is part of the spacer group.

Representative examples of useful monomers include those derived from the reaction of an alkenyl azlactone of general Formula II:

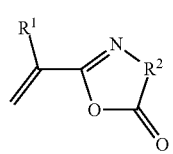
(II)

or an ethylenically unsaturated isocyanate of general Formula III:

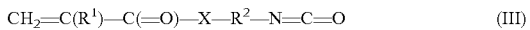

with an acidic group-containing compound (or salt thereof) of general Formula IV:

to produce monomer of general Formula I (wherein $R^1$, X, $R^2$, and L in Formulas II, III, and/or IV are as defined above for Formula I).

In certain embodiments, filter media used in processes of the present disclosure can be made by subjecting a mixture of monomers of general Formula I, for example, to radiation (e.g., electron beam radiation) in the presence of a suitable substrate. A first monomer from the mixture of monomers is attached to the surface of the substrate creating a radical that reacts with a second monomer to form another radical that reacts with a third monomer, etc. In this way, a polymer can be grafted to the substrate surface.

In an alternative, although not necessarily preferred, method for the preparation of filter media as described herein, a porous substrate can be grafted, in a first step, with a monomer of general Formula II or general Formula III, or a mixture thereof. The grafted substrate can then, in a second step, be reacted with a first acidic group-containing compound of general Formula IV or mixture of two or more such compounds. Alternatively, in this second step, a portion of the grafted product of the first step can be reacted with a first acidic group-containing compound and the remaining portion of the grafted product can be reacted with a second acidic group-containing compound. The first step can be carried out using any of the common processes known for grafting of monomers to substrates (e.g., by using UV, gamma, and/or e-beam irradiation), with the precaution that solvents that are not reactive with the monomers of Formulas II and III are used. In the second step, a solvent that does not react with the azlactone group or isocyanate group of the grafted polymer, but that does dissolve the acidic group-containing compound of Formula IV is chosen. Such precautions are taken to minimize competing hydrolysis or solvolysis of the very reactive azlactone and isocyanate groups. Optionally, the acidic group-containing compound may be neutralized (converted to the salt form) prior to or subsequent to reaction.

Representative examples of useful alkenyl azlactones of Formula II include 4,4-dimethyl-2-vinyl-4H-oxazol-5-one (vinyldimethylazlactone, VDM), 2-isopropenyl-4H-oxazol-5-one, 4,4-dimethyl-2-isopropenyl-4H-oxazol-5-one, 2-vinyl-4,5-dihydro-[1,3]oxazin-6-one, 4,4-dimethyl-2-vinyl-4,5-dihydro-[1,3]oxazin-6-one, 4,5-dimethyl-2-vinyl-4,5-dihydro-[1,3]oxazin-6-one, and the like, and combinations thereof.

Representative examples of ethylenically unsaturated isocyanates of general Formula III include 2-isocyanatoethyl (meth)acrylate (IEM or IEA), 3-isocyanatopropyl (meth)acrylate, 4-isocyanatocyclohexyl (meth)acrylate, and the like, and combinations thereof.

Representative examples of useful compounds of general Formula IV include amino group-containing carboxylic, sulfonic, boronic, and phosphonic acids and combinations thereof, or salts thereof. Useful amino carboxylic acids include α-amino acids (L-, D-, or DL-α-amino acids) such as glycine, alanine, valine, proline, serine, phenylalanine, histidine, tryptophan, asparagine, glutamine, N-benzylglycine, N-phenylglycine, sarcosine, and the like; β-aminoacids such as β-alanine, homoleucine, homoglutamine, homophenylalanine, and the like; other α,ω-aminoacids such as γ-aminobutyric acid, 6-aminohexanoic acid, 11-aminoundecanoic acid, peptides (such as diglycine, triglycine, tetraglycine, as well as other peptides containing a mixture of different aminoacids), and the like; and combinations thereof. Useful amino sulfonic acids include aminomethanesulfonic acid, 2-aminoethanesulfonic acid (taurine), 3-amino-1-propanesulfonic acid, 6-amino-1-hexanesulfonic acid, and the like, and combinations thereof. Useful aminoboronic acids include m-aminophenylboronic acid, p-aminophenylboronic acid, and the like, and combinations thereof. Useful aminophosphonic acids include 1-aminomethylphosphonic acid, 2-aminoethylphosphonic acid, 3-aminopropylphosphonic acid, and the like, and combinations thereof.

Useful compounds containing more than one acidic group include aspartic acid, glutamic acid, α-aminoadipic acid, iminodiacetic acid, $N_\alpha,N_\alpha$-bis(carboxymethyl)lysine, cysteic acid, N-phosphonomethylglycine, and the like, and combinations thereof.

Representative examples of other useful acidic group-containing compounds include compounds including a hydroxy group and an acidic group. Specific examples include glycolic acid, lactic acid, 6-hydroxyhexanoic acid, citric acid, 2-hydroxyethylsulfonic acid, 2-hydroxyethylphosphonic acid, and the like, and combinations thereof.

Many of the above-described acidic group-containing compounds are commercially available. Still other useful acidic group-containing compounds can be prepared by common synthetic procedures. For example, various diamines or aminoalcohols can be reacted with one equivalent of a cyclic anhydride to produce an intermediate acidic group-containing compound including a carboxyl group and an amino or hydroxy group.

Useful monomers can also be prepared by the reaction of acidic group-containing compounds with ethylenically unsaturated acyl halides (for example, (meth)acryloyl chloride). In addition, useful monomers can be prepared by reaction of hydroxy- or amine-containing (meth)acrylate or (meth)acrylamide monomers with a cyclic anhydride to produce carboxyl group-containing monomers.

In certain embodiments, useful monomers may be prepared from the reaction of alkenyl azlactones with aminocarboxylic acids, monomers prepared from the reaction of alkenyl azlactones with aminosulfonic acids, monomers prepared from the reaction of ethylenically unsaturated isocyanates with aminocarboxylic acids, monomers prepared from the reaction of ethylenically unsaturated isocyanates with aminosulfonic acids, or combinations thereof.

In certain embodiments, useful monomers are the following (which are shown as acids, but which can also be used as salts thereof:

VDM-4-aminobutyric acid (VDM-GABA):

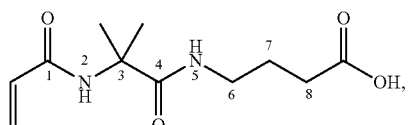

VDM-Phenylalanine:

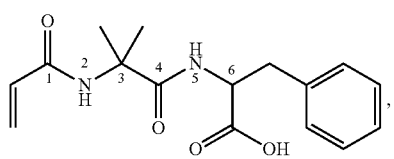

IEM-4-aminobutyric acid (IEM-GABA):

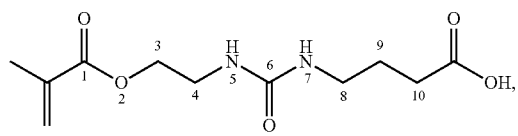

IEM-Phenylalanine:

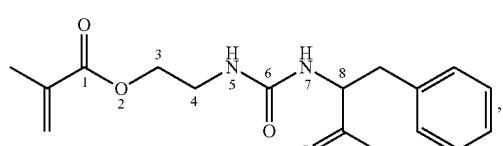

VDM-4-aminomethyl-cyclohexanecarboxylic acid:

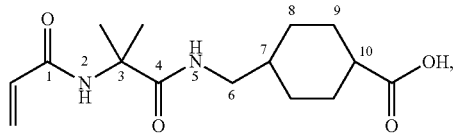

IEM-Glycine:

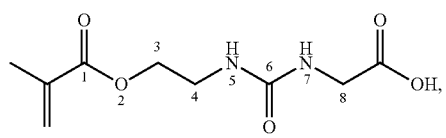

IEM-Taurine:

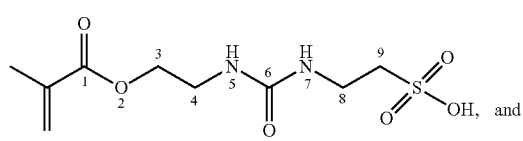

and

VDM-Taurine:

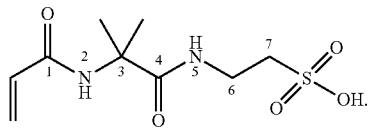

In certain embodiments, the copolymer is prepared from the following two monomers:

Monomer 1: VDM-4-aminobutyric acid (VDM-GABA)

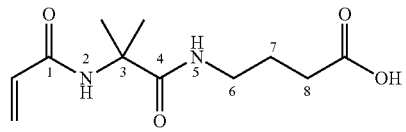

Monomer 2: VDM-Phenylalanine

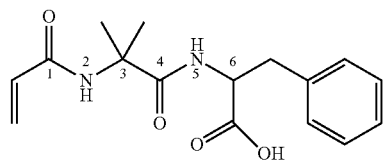

In certain embodiments, the copolymer is prepared from the following two monomers:

Monomer 1: IEM-4-aminobutyric acid (IEM-GABA)

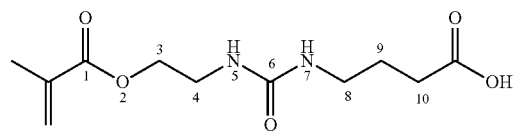

Monomer 2: IEM-Phenylalanine

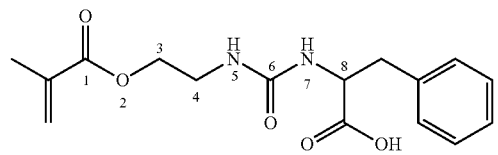

In certain embodiments, the copolymer is prepared from the following two monomers:

Monomer 1: VDM-4-aminobutyric acid (VDM-GABA)

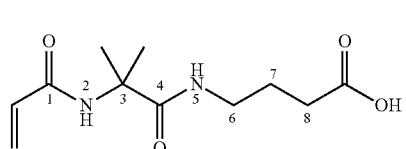

Monomer 2: VDM-4-aminomethyl-cyclohexanecarboxylic acid

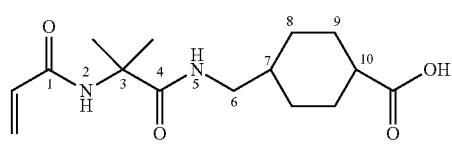

In certain embodiments, the copolymer is prepared from the following two monomers:

Monomer 1: IEM-Glycine

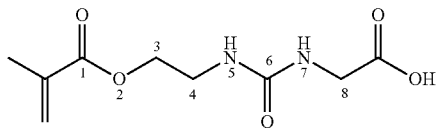

Monomer 2: IEM-Phenylalanine

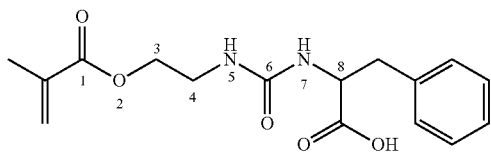

In certain embodiments, the copolymer is prepared from the following two monomers:

Monomer 1: IEM-Glycine

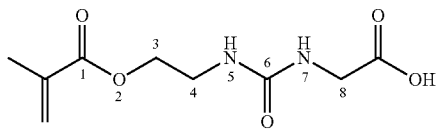

Monomer 2: VDM-Phenylalanine

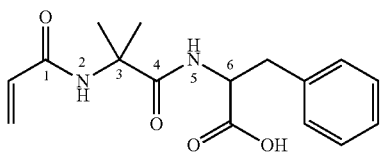

In certain embodiments, the copolymer is prepared from the following two monomers:

Monomer 1: IEM-Taurine

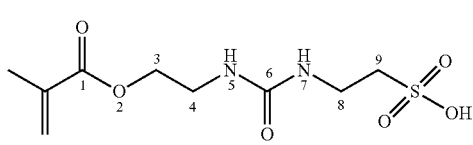

Monomer 2: IEM-Phenylalanine

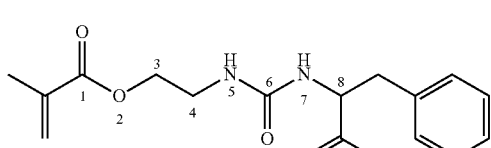

In certain embodiments, the copolymer is prepared from the following two monomers:

Monomer 1: VDM-Taurine

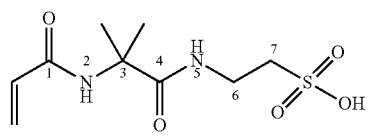

Monomer 2: VDM-Phenylalanine

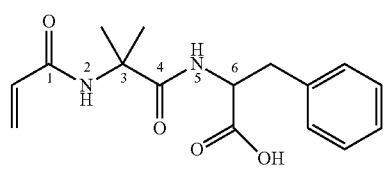

At least two different monomers of the above-described monomers can be copolymerized. Such monomers are referred to as, for example, first and second monomers.

A skilled artisan will recognize, however, that these monomers can be copolymerized with other monomers (hereinafter, termed "modifying comonomers"; for example, modifying comonomers having shorter spacer groups or modifying comonomers including other types of ligands or even modifying comonomers that are ligand-free) in order to adjust binding capacity and/or to achieve special properties, provided that the type and degree of binding capacity desired for a particular application can be achieved.

For example, the monomer(s) optionally can be copolymerized with one or more hydrophilic modifying comonomer(s) including at least one alkenyl group (preferably, a (meth)acryloyl group) and a hydrophilic group (including, for example, a poly(oxyalkylene) group, hydroxyl group, amino group, or amido group) in order to impart a degree of hydrophilicity to the porous substrate. Suitable hydrophilic modifying comonomers include acrylamide, dimethylacrylamide, hydroxyethyl(meth)acrylate, hydroxypropyl(meth)acrylate, polyethyleneglycolmono(meth)acrylate, 2-hydroxyethylacrylamide, N-vinylpyrrolidone, and the like, and combinations thereof.

Optionally, the monomer(s) can be copolymerized with one or more modifying (meth)acryloyl comonomer(s) containing at least two free radically polymerizable groups. Such multifunctional (meth)acryloyl comonomer(s) (including multifunctional (meth)acrylate(s) and (meth)acrylamide(s)) can be incorporated in a blend of polymerizable monomer(s) generally in only relatively small amounts (for example, from 0.1 to 5 percent by weight, based upon the total weight of monomer(s) and comonomer(s)) to impart a degree of branching and/or relatively light crosslinking to a resulting copolymer. Higher amounts can be used for certain applications, but it should be understood that the use of higher amounts may reduce binding capacity for a target biomaterial (e.g., aggregated proteins).

Useful modifying multifunctional (meth)acryloyl comonomers include di(meth)acrylates, tri(meth)acrylates, tetra(meth)acrylates, multifunctional (meth)acrylamides, and the like, and combinations thereof. Such multifunctional (meth)acryloyl comonomers include ethyleneglycol di(meth)acrylate, 1,6-hexanediol di(meth)acrylate, poly(ethylene glycol) di(meth)acrylates, polybutadiene di(meth)acrylate, polyurethane di(meth)acrylates, propoxylated glycerin tri(meth)acrylate, methylenebisacrylamide, ethylenebisacrylamide, hexamethylenebisacrylamide, diacryloylpiperazine, and the like, and combinations thereof Article Preparation Polymerization of the monomer(s) can be carried out by using known techniques. For example, the polymerization can be initiated with either a thermal initiator or a photoinitiator (preferably, a photoinitiator). A wide variety of conventional free radical initiators can be used to generate the initial radical. Examples of suitable thermal initiators include peroxides such as benzoyl peroxide, dibenzoyl peroxide, dilauryl peroxide, cyclohexane peroxide, methyl ethyl ketone peroxide, hydroperoxides (for example, tert-butyl hydroperoxide and cumene hydroperoxide), dicyclohexyl peroxydicarbonate, t-butyl perbenzoate; and the like; and combinations thereof. Examples of commercially available thermal initiators include initiators available from DuPont Specialty Chemical (Wilmington, Del.) under the VAZO trade designation including VAZO 67 (2,2'-azo-bis(2-methylbutyronitrile)), VAZO 64 (2,2'-azo-bis(isobutyronitrile)), and VAZO 52 (2,2'-azo-bis(2,2-dimethylvaleronitrile)), as well as that available under the trade designation LUCIDOL 70 (benzoylperoxide) from Elf Atochem North America (Philadelphia, Pa.).

Useful photoinitiators include benzoin ethers such as benzoin methyl ether and benzoin isopropyl ether; substituted acetophenones such as 2,2-dimethoxyacetophenone available as IRGACURE 651 photoinitiator (Ciba Specialty Chemicals), 2,2 dimethoxy-2-phenyl-1-phenylethanone available as ESACURE KB-1 photoinitiator (Sartomer Co., West Chester, Pa.), 1-[4-(2-hydroxyethoxy)phenyl]-2-hydroxy-2-methyl-1-propan-1-one available as IRGACURE 2959 (Ciba Specialty Chemicals), and dimethoxyhydroxyacetophenone; substituted α-ketols such as 2-methyl-2-hydroxy propiophenone; aromatic sulfonyl chlorides such as 2-naphthalene-sulfonyl chloride; photoactive oximes such as 1-phenyl-1,2-propanedione-2-(O-ethoxy-carbonyl)oxime; and the like; and combinations thereof. Particularly preferred among these are the substituted acetophenones (especially 1-[4-(2-hydroxyethoxy)phenyl]-2-hydroxy-2-methyl-1-propan-1-one, IRGACURE 2959, due to its water solubility). A useful polymerizable photoinitiator is a 1:1 adduct of 2-vinyl-4,4-dimethylazlactone and IRGACURE 2959, which can be prepared essentially as described in Example 1 of U.S. Pat. No. 5,506,279 (Babu et al.).

Other useful photoinitiators include hydrogen-abstracting (Type II) photoinitiators such as benzophenone, 4-(3-sulfopropyloxy)benzophenone sodium salt, Michler's ketone, benzil, anthraquinone, 5,12-naphthacenequinone, aceanthracenequinone, benz(A)anthracene-7,12-dione, 1,4-chrysenequinone, 6,13-pentacenequinone, 5,7,12,14-pentacenetetrone, 9-fluorenone, anthrone, xanthone, thioxanthone, 2-(3-sulfopropyloxy)thioxanthen-9-one, acridone, dibenzosuberone, acetophenone, chromone, and the like, and combinations thereof.

The initiator can be used in an amount effective to initiate free radical polymerization of the monomer(s). Such amount will vary depending upon, for example, the type of initiator and polymerization conditions utilized. The initiator generally can be used in amounts ranging from 0.01 part by weight to 5 parts by weight, based upon 100 parts total monomer.

The polymerization solvent can be essentially any solvent that can substantially dissolve (or, in the case of emulsion or suspension polymerizations, disperse or suspend) the monomer(s) (and comonomer(s), if used). In many embodiments, the solvent can be water or a water/water-miscible organic solvent mixture. The ratio of water to organic solvent can vary widely, depending upon monomer solubility. With some monomers, the ratio typically can be greater than 1:1 (volume/volume) water to organic solvent (preferably, greater than 5:1; more preferably, greater than 7:1). With other monomers, a higher proportion of organic solvent (even up to 100 percent) can be preferred (with some alcohols especially).

Any such water-miscible organic solvent preferably has no groups that would retard polymerization. In some embodiments, the water-miscible solvents can be protic group-containing organic liquids such as the lower alcohols having 1 to 4 carbon atoms, lower glycols having 2 to 6 carbon atoms, and lower glycol ethers having 3 to 6 carbon atoms and 1 to 2 ether linkages. In some embodiments, higher glycols such as poly(ethylene glycol) can be used. Specific examples include methanol, ethanol, isopropanol, n-butanol, t-butyl alcohol, ethylene glycol, methoxyethanol, ethoxyethanol, propoxyethanol, butoxyethanol, methyl carbitol, ethyl carbitol, and the like, and combinations thereof.

In other embodiments, non-protic water-miscible organic solvents can be used. Such solvents include aliphatic esters (for example, methoxyethyl acetate, ethoxyethyl acetate, propoxyethyl acetate, butoxyethyl acetate, and triethyl phosphate), ketones (for example, acetone, methyl ethyl ketone, and methyl propyl ketone), and sulfoxides (for example, dimethyl sulfoxide).

The monomer concentration in the polymerization solvent can vary, depending upon a number of factors including, but not limited to, the nature of the monomer or monomers, the extent of polymerization desired, the reactivity of the monomer(s), and the solvent used. Typically, the monomer concentration can range from 0.1 weight percent (wt %) to 60 wt % (preferably, from 1 wt % to 40 wt %; more preferably, from 5 wt % to 30 wt %), based upon the total weight of monomer and solvent.

An aqueous monomer mixture optionally can be formulated with relatively higher levels of multifunctional (crosslinking) monomers or modifying comonomers (for example, from 5 wt % to 90 wt %, based upon the total weight of monomer(s) and comonomer(s)) and polymerized as a suspension or dispersion in a nonpolar, immiscible organic solvent, optionally in the presence of added porogen(s), to produce crosslinked, porous particles including the instant monomer(s). Such methods are well known and are described, for example, in U.S. Pat. No. 7,098,253 (Rasmussen et al.), U.S. Pat. No. 7,674,835 (Rasmussen et al.), U.S. Pat. No. 7,647,836 (Rasmussen et al.), and U.S. Pat. No. 7,683,100 (Rasmussen et al.).

The porous substrate can be in essentially any form such as particles, fibers, films, webs, membranes, sponges, or sheets. Suitable porous substrates can be organic, inorganic, or a combination thereof (preferably, organic; more preferably, polymeric). Suitable porous substrates include porous particles, porous membranes, porous nonwoven webs, porous woven webs, porous sponges, porous fibers, and the like, and combinations thereof. Preferred porous substrates include porous membranes (more preferably, porous polymeric membranes; even more preferably, porous polyamide membranes) and combinations thereof.

For example, the porous substrate can be formed from any suitable thermoplastic polymeric material. Suitable polymeric materials include polyolefins, poly(isoprenes), poly(butadienes), fluorinated polymers, chlorinated polymers, polyamides, polyimides, polyethers, poly(ether sulfones), poly(sulfones), poly(vinyl acetates), polyesters such as poly(lactic acid), copolymers of vinyl acetate such as poly(ethylene)-co-poly(vinyl alcohol), poly(phosphazenes), poly (vinyl esters), poly(vinyl ethers), poly(vinyl alcohols), poly (carbonates), and the like, and combinations thereof.

In some embodiments, the thermoplastic polymer can be surface treated, such as by plasma discharge or by use of a primer, to provide suitable functionality to the surface of the porous substrate. Surface treatment can provide functional groups such as hydroxy groups that can improve wetting by the monomer solution. One such useful plasma treatment is described in U.S. Pat. No. 7,125,603 (David et al.).

Suitable polyolefins include poly(ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene), poly(ethylene-co-1-butene-co-1-hexene), and the like, and combinations thereof.

Suitable fluorinated polymers include poly(vinyl fluoride), poly(vinylidene fluoride), copolymers of vinylidene fluoride (such as poly(vinylidene fluoride-co-hexafluoropropylene)), copolymers of chlorotrifluoroethylene (such as poly(ethylene-co-chlorotrifluoroethylene)), and the like, and combinations thereof.

Suitable polyamides include poly(iminoadipolyiminohexamethylene), poly(iminoadipolyiminodecamethylene), polycaprolactam, and the like, and combinations thereof. Suitable polyimides include poly(pyromellitimide), and the like, and combinations thereof.

Suitable poly(ether sulfones) include poly(diphenylether sulfone), poly(diphenylsulfone-co-diphenylene oxide sulfone), and the like, and combinations thereof.

Suitable copolymers of vinyl acetate include poly(ethylene-co-vinyl acetate), such copolymers in which at least some of the acetate groups have been hydrolyzed to afford various poly(vinyl alcohols), and the like, and combinations thereof.

A preferred porous substrate is a microporous membrane such as a thermally induced phase separation (TIPS) membrane. TIPS membranes are often prepared by forming a solution of a thermoplastic material and a second material above the melting point of the thermoplastic material. Upon cooling, the thermoplastic material crystallizes and phase separates from the second material. The crystallized material is often stretched. The second material is optionally removed either before or after stretching Microporous membranes are further described in U.S. Pat. No. 4,539,256 (Shipman); U.S. Pat. No. 4,726,989 (Mrozinski); U.S. Pat. No. 4,867,881 (Kinzer); U.S. Pat. No. 5,120,594 (Mrozinski); U.S. Pat. No. 5,260,360 (Mrozinski); and U.S. Pat. No. 5,962,544 (Waller, Jr.). Some exemplary TIPS membranes include poly(vinylidene fluoride) (PVDF), polyolefins such as poly(ethylene) or poly(propylene), vinyl-containing polymers or copolymers such as ethylene-vinyl alcohol copolymers and butadiene-containing polymers or copolymers, and acrylate-containing polymers or copolymers. For some applications, a TIPS membrane including PVDF can be particularly desirable. TIPS membranes including PVDF are further described in U.S. Pat. No. 7,338,692 (Smith et al.).

In many embodiments, the porous substrate can have an average pore size that is typically greater than 0.2 micrometer in order to minimize size exclusion separations, minimize diffusion constraints, and maximize surface area and separation based on binding of a target biomaterial (e.g., aggregated proteins). Generally, the pore size can be in the range of 0.1 to 10 micrometers (preferably, 0.5 to 3 micrometers; and more preferably, 0.8 to 2 micrometers when used for binding of proteins (particularly aggregated proteins)). The efficiency of binding other target biomaterials can confer different optimal ranges.

In an exemplary embodiment, the porous substrate can include a nylon microporous film or sheet (for example, a microporous membrane), such as those described in U.S. Pat. No. 6,056,529 (Meyering et al.), U.S. Pat. No. 6,267,916 (Meyering et al.), U.S. Pat. No. 6,413,070 (Meyering et al.), U.S. Pat. No. 6,776,940 (Meyering et al.), U.S. Pat. No. 3,876,738 (Marinaccio et al.), U.S. Pat. No. 3,928,517 (Knight et al.), U.S. Pat. No. 4,707,265 (Barnes, Jr. et al.), and U.S. Pat. No. 5,458,782 (Hou et al.).

In other embodiments, the porous substrate can be a nonwoven web, which can include nonwoven webs manufactured by any of the commonly known processes for producing nonwoven webs. As used herein, the term "nonwoven web" refers to a fabric that has a structure of individual fibers or filaments that are randomly and/or unidirectionally interlaid in a mat-like fashion.

For example, the fibrous nonwoven web can be made by wet laid, carded, air laid, spunlaced, spunbonding, or meltblowing techniques, or combinations thereof. Spunbonded fibers are typically small diameter fibers that are formed by extruding molten thermoplastic polymer as filaments from a plurality of fine, usually circular capillaries of a spinneret, with the diameter of the extruded fibers being rapidly reduced. Meltblown fibers are typically formed by extruding molten thermoplastic material through a plurality of fine, usually circular, die capillaries as molten threads or filaments into a high velocity, usually heated gas (for example, air) stream, which attenuates the filaments of molten thermoplastic material to reduce their diameter. Thereafter, the meltblown fibers are carried by the high velocity gas stream and are deposited on a collecting surface to form a web of randomly-dispersed, meltblown fibers. Any of the nonwoven webs can be made from a single type of fiber or from two or more fibers that differ in the type of thermoplastic polymer and/or thickness.

Further details of manufacturing methods of useful nonwoven webs have been described by Wente in "Superfine Thermoplastic Fibers," 48 Indus. Eng. Chem. 1342 (1956) and by Wente et al. in "Manufacture Of Superfine Organic Fibers," Naval Research Laboratories Report No. 4364 (1954).

Following polymerization, washing, and drying, typical total weight gains by the porous substrate generally can be in the range of 0.5 percent (%) to 30% (preferably, in the range of 2% to 10%). Polymerization of the monomer(s) in the presence of a porous substrate can produce a polymer-bearing porous substrate. The copolymer is grafted (covalently bonded) to the surface of the porous substrate. If desired, the polymerization can be carried out separately and the resulting polymer then grafted (covalently bonded) to the porous substrate, but this is generally less preferred.

In an exemplary method, the monomer(s) can be free radically polymerized and grafted to the surface of a porous substrate in the presence of a Type II photoinitiator, as described in Patent Application No. US2015/0136698 (3M Innovative Properties Co.). Alternatively, the monomer(s) can be free radically polymerized and grafted to a porous substrate including a crosslinked copolymer layer, the copolymer including photoinitiator-containing monomer units, as described in International Publication No. WO 2014/052215 (Rasmussen et al.). In addition, the monomer(s) can be free radically polymerized and grafted to a porous substrate including a crosslinked polymer primer layer, as described in U.S. Patent Application Publication No. 2012/0252091 A1 (Rasmussen et al.). In yet another exemplary method, the monomer(s) can be free radically polymerized and grafted to a porous particle, as described in U.S. Patent Application Publication No. 2011/0100916 A1 (Shannon et al.).

In certain embodiments, acidic groups or salts thereof of the copolymer are covalently bonded to the porous substrate at a density of at least 0.02 millimole per gram (mmole/gram) of filter media, or at least 0.03 mmole/gram of filter media, or at least 0.04 mmole/gram of filter media, or at least 0.05 mmole/gram of filter media. In certain embodiments, acidic groups or salts thereof of the copolymer are covalently bonded to the porous substrate at a density of up to 0.6 mmole/gram of filter media, or up to 0.5 mmole/gram of filter media, or up to 0.4 mmole/gram of filter media, up to 0.35 mmole/gram, or up to 0.3 mmole/gram, of filter media.

The grafted copolymer (which is a functional copolymer due to the presence of the acidic groups, or salts thereof, of the monomer(s)) can alter the original nature of the porous substrate. The resulting copolymer-bearing porous substrates (functionalized porous substrates) can retain many of the advantages of the original porous substrate (for example, mechanical and thermal stability, porosity, and so forth) but can also exhibit enhanced binding capacity for biomaterials such as proteins (particularly aggregated proteins), and the like. Porous substrates bearing the functional copolymer can be particularly useful as filter media for the selective binding and/or removal of target biomaterials or biological species (including relatively neutral or charged biomaterials such as basic carbohydrates, enzymes, proteins (particularly aggregated proteins), and the like from biological samples. Articles including the copolymer-bearing porous substrates can further include conventional components such as housings, holders, adapters, and the like, and combinations thereof.

If desired, efficiency of binding and capture of biomaterials (e.g., aggregated proteins) can be improved by using a plurality of stacked or layered, functionalized porous substrates (for example, functionalized porous membranes) as a filter element. Thus, a filter element can include one or more layers of functionalized porous substrate. The individual layers of the filter element can be the same or different. The layers can vary in porosity, degree of grafting, and so forth. The filter element can further include an upstream prefilter layer and/or a downstream support layer. The individual layers can be planar or pleated, as desired.

Examples of suitable prefilter and support layer materials include any suitable porous membranes of polypropylene, polyester, polyamide, resin-bonded or binder-free fibers (for example, glass fibers), and other synthetics (woven and nonwoven fleece structures); sintered materials such as polyolefins, metals, and ceramics; yarns; special filter papers (for example, mixtures of fibers, cellulose, polyolefins, and binders); polymer membranes; and the like; and combinations thereof.

Useful articles for biomaterial capture or filtration applications include a filter cartridge including one or more of the above-described filter elements, a filter assembly including one or more of the above-described filter elements and a filter housing, and the like. Other useful articles can be in the form of an array of sample containers (e.g., a 96-well plate) with each container including a filter element having a contacting surface (e.g., an upstream or upper surface).

Methods of Use

In certain aspects of the disclosure, a process for capture or removal of a target biomaterial is provided that uses articles of the present disclosure that include filter elements having a contacting surface (e.g., an upstream or upper surface). Such articles can be in the form of an array of sample containers (e.g., a 96-well plate) with each container including a filter element having a contacting surface (e.g., an upstream or upper surface). The process includes: providing a filter element or an array of sample containers of the present disclosure; and allowing a biological solution including a target biomaterial to contact the contacting surface (e.g., upstream or upper surface) of the filter element under conditions effective for binding of the target biomaterial.

Target biomaterials may include proteins. A wide variety of biological solutions containing a protein may be utilized in the processes of the present disclosure. The solution, which contains a protein, may include, for example, fermentation broth or cell culture or murine ascites fluid. The protein can be any protein, or fragment thereof, known in the art. The protein may be derived from natural sources or from recombinant sources. The protein may have a native sequence or a non-natural sequence. In some embodiments, the protein is an enzyme. In some embodiments, the protein is a hormone. In some embodiments, the protein is an antibody. In a particular embodiment, the protein is a monoclonal antibody, or a fragment thereof. Fragments of antibodies include F(ab), F(ab'), F(ab')$_2$, Fv, and single-chain antibodies. In some cases, the protein may be a human monoclonal antibody. In other cases, the protein is an immunoglobulin G (IgG) antibody. In still other cases, the protein is a fusion protein such as an Fc-fusion protein.

In certain processes of the present disclosure, the target biomaterial includes aggregated proteins (in particular, antibodies). Thus, in another aspect of the disclosure, a process is provided that results in the separation of aggregated proteins (in particular, antibodies) from monomeric proteins (in particular, antibodies). The process involves allowing an initial biological solution that includes aggregated proteins (in particular, antibodies) (the target biomaterial) and monomeric proteins (in particular, antibodies), to contact the contacting surface (e.g., upstream or upper surface) of the filter element under conditions effective to separate the aggregated proteins from the monomeric proteins such that a final biological solution (i.e., the product obtained by contacting the initial biological solution with the filter element) includes purified monomeric proteins.

The process of separation of aggregated proteins from monomeric proteins in a biological solution results from binding aggregated proteins to the filter media while permitting passage of monomeric proteins. In early stages of separation with low challenge loads, monomeric proteins may be bound to the filter media; however, as the challenge load increases, preferential binding of the aggregated proteins displaces monomeric proteins. Thus, although the process may involve binding of monomeric proteins to the filter media at low challenge loads, the process ultimately results in separating the aggregated proteins from the monomeric proteins such that a final biological solution includes purified monomeric proteins.

In certain embodiments of the process, allowing the biological solution to contact the contacting surface (e.g., upstream or upper surface) of the filter element occurs by passing the biological solution across the filter media or by allowing the biological solution to flow through the filter media, or both. In certain embodiments, allowing the biological solution to contact the contacting surface (e.g., upstream or upper surface) involves allowing the biological solution to flow through filter media.

In certain embodiments, the process involves purifying the monomeric proteins without the need for an eluting step. That is, this process does not bind the monomeric proteins and wash through the aggregated proteins; rather, it is binding the aggregated proteins and allowing the monomeric proteins to pass through. This is advantageous at least because it avoids dilution of the monomeric proteins, which prevents the need to later concentrate the eluted monomeric proteins, thereby providing processing efficiency and decreasing processing time. This is also advantageous because it allows for the capture and disposal of aggregated proteins bound to the filter media, which is desirable when the filter media is enclosed within a disposable filter article. Furthermore, buffer exchanges and pH adjustments may be unnecessary.

In certain embodiments, the process involves recovering, in a final solution, at least 40%, or at least 45%, or at least 50%, or at least 55%, or at least 60%, or at least 65%, or at least 70%, or at least 75%, or at least 80%, or at least 85%, or at least 90%, or at least 95%, of the monomeric proteins present in the initial biological solution (i.e., the biological solution before being subjected to a process as described herein).

In certain embodiments, the process involves removing at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, of the aggregated proteins from the initial biological solution.

The process involves allowing the biological solution to contact the contacting surface (e.g., upstream or upper surface) of the filter element under conditions effective to separate the aggregated proteins from the monomeric proteins to provide the desired results.

In certain embodiments, such conditions include a pH of the biological solution of below 9, or below 8.5, or below 8, or below 7.5, or below 7, or below 6.5. In certain embodiments, such conditions include a pH of the biological solution of at least 4, or at least 4.5, or at least 5.

In certain embodiments, such conditions include a conductivity of the biological solution of at least 1 millisiemens per centimeter (mS/cm), or at least 2 mS/cm, or at least 3 mS/cm, or at least 4 mS/cm, or at least 5 mS/cm, or at least 6 mS/cm, or at least 7 mS/cm, or at least 8 mS/cm, or at least 9 mS/cm, or at least 10 mS/cm. In certain embodiments, such conditions include a conductivity of the biological solution of no greater than 110 mS/cm, or no greater than 100 mS/cm, or no greater than 50 mS/cm, or no greater than 40 mS/cm, or no greater than 30 mS/cm.

In certain embodiments, such conductivity of the biological solution is provided by a buffer that includes an inorganic salt, organic salt, or a combination thereof. In certain embodiments, such buffer salt includes a chloride (e.g., NaCl), a phosphate, a citrate, a sulfate, an acetate, or a combination thereof.

In certain embodiments, such conditions include a challenge load of at least 1 gram per liter (g/L) of filter media, or at least 10 g/L of filter media, or at least 25 g/L of filter media, or at least 50 g/L of filter media, or at least 75 g/L of filter media, or at least 100 g/L, or at least 500 g/L, or at least 1000 g/L, or at least 2000 g/L, of filter media. In this context, "challenge load" means the amount of proteins (aggregated and monomeric) per volume of filter media in grams per liter. The upper limit of the challenge load is determined by a number of things, including the selectivity for aggregated proteins over monomeric proteins, the actual amount of aggregated proteins in the initial biological solution, the total protein concentration in the initial biological solution, etc. Desirably, the challenge load is in the kilogram to multi-kilogram range and as high a challenge load as possible.

In certain embodiments, assessment of optimal conditions for the process is conveniently conducted using an array of sample containers, wherein each container includes filter elements of the present disclosure. A particularly useful array of containers is, for example, a 96-well filter plate in which each well includes filter elements of the disclosure. Each well of an individual plate may include the same filter element, that is, the filter elements may be functionalized with the same copolymer composition. Alternatively, two or more different filter elements, i.e., functionalized with different copolymer compositions, may be disposed within the wells of a single plate. Each well may include a single layer of a filter element, or alternatively may contain more than one layer of filter elements. In the latter case, the multiple layers of filter elements may be functionalized with the same copolymer, or with different copolymers. Protein solutions may then be prepared utilizing a variety of buffer salts, buffer pH values, buffer conductivities, and/or protein concentrations. These initial solutions may then be applied into the wells of the plate so as to contact the contacting surface (e.g., upstream or upper surface) of the filter elements. Following a predetermined contact time, the protein solution may be passed through the filter elements, such as by centrifugation or by vacuum filtration, and may be collected in the wells of a collection plate. The filtrate (final solution) thus collected may be analyzed for concentration of monomeric protein and aggregated protein, such as by HPLC analysis, and compared with that of the initial solution. In this manner, optimal conditions (in terms of buffer, pH, conductivity, etc.) for removal of aggregated protein with minimal loss of monomeric protein can be assessed within the context of a single, high throughput experiment. Such techniques are well known to one of skill in the art.

Embodiments

Embodiment 1 is an article comprising:

a) a porous substrate; and b) a copolymer covalently attached to the porous substrate, the copolymer comprising a hydrocarbon backbone and a plurality of pendant groups attached to the hydrocarbon backbone, wherein:

1) each of a first plurality of pendant groups comprises:

(a) at least one acidic group or salt thereof; and (b) a spacer group that directly links the at least one acidic group or salt thereof to the hydrocarbon backbone by a chain of at least 6 catenated atoms; and 2) each of a second plurality of pendant groups comprises:

(a) at least one acidic group or salt thereof; and (b) a spacer group that directly links the at least one acidic group or salt thereof to the hydrocarbon backbone by a chain of at least 6 catenated atoms; and wherein the first plurality of pendant groups are different than the second plurality of pendant groups; and wherein a mole ratio of the first plurality of pendant groups to the second plurality of pendant groups is in a range of 95:5 to 5:95.

Embodiment 2 is an article comprising:
a) a porous substrate; and
b) a copolymer covalently attached to the porous substrate, the copolymer comprising a reaction product of a monomer composition comprising:
1) a first monomer comprising (in some embodiments, consisting of):
  (a) at least one ethylenically unsaturated group (in some embodiments, a terminal ethylenically unsaturated group);
  (b) at least one acidic group or salt thereof; and
  (c) a spacer group that directly links the at least one ethylenically unsaturated group and the at least acidic group or salt thereof by a chain of at least 6 catenated atoms; and
2) a second monomer comprising (in some embodiments, consisting of):
  (a) at least one ethylenically unsaturated group (in some embodiments, a terminal ethylenically unsaturated group);
  (b) at least one acidic group or salt thereof; and
  (c) a spacer group that directly links the at least one ethylenically unsaturated group and the at least one acidic group or salt thereof by a chain of at least 6 catenated atoms;
wherein the second monomer is different than the first monomer; and
wherein a mole ratio of the first monomer to the second monomer is in a range of 95:5 to 5:95.

Embodiment 3 is the article of embodiment 1 or 2 wherein the at least one acidic group or salt thereof of the copolymer covalently bonded to the porous substrate is present at a density of at least 0.01 mmole/gram of filter media, or at least 0.02 mmole/gram of filter media, or at least 0.03 mmole/gram of filter media, or at least 0.04 mmole/gram of filter media, or at least 0.05 mmole/gram of filter media.

Embodiment 4 is the article of any one of embodiments 1 through 3 wherein the at least one acidic group or salt thereof of the copolymer covalently bonded to the porous substrate is present at a density of up to 0.6 mmole/gram of filter media, or up to 0.5 mmole/gram of filter media, or up to 0.4 mmole/gram of filter media, up to 0.35 mmole/gram, or up to 0.3 mmole/gram, of filter media.

Embodiment 5 is the article of any one of embodiments 1 through 4 wherein the porous substrate is a porous membrane.

Embodiment 6 is the article of any one of embodiments 1 through 5 wherein the porous substrate is polymeric.

Embodiment 7 is the article of any one of embodiments 2 through 6, as dependent on embodiment 2, wherein the at least one ethylenically unsaturated group of the first monomer is selected from an ethenyl group, a 1-alkylethenyl group, and a combination thereof.

Embodiment 8 is the article of embodiment 7 wherein the first monomer is a (meth)acryloyl monomer.

Embodiment 9 is the article of any one of embodiments 2 through 8, as dependent on embodiment 2, wherein the at least one ethylenically unsaturated group of the second monomer is selected from an ethenyl group, a 1-alkylethenyl group, and a combination thereof.

Embodiment 10 is the article of embodiment 9 wherein the second monomer is a (meth)acryloyl monomer.

Embodiment 11 is the article of any one of embodiments 1 through 10 wherein the at least one acidic group or salt thereof in the first and/or second plurality of pendant groups of the copolymer or in the first and/or second monomer is selected from a carboxy group, a phosphono group, a phosphato group, a sulfono group, a sulfato group, a boronato group, and a combination thereof.

Embodiment 12 is the article of embodiment 11 wherein the at least one acidic group or salt thereof is selected from a carboxy group, a phosphono group, a sulfono group, and a combination thereof.

Embodiment 13 is the article of embodiment 12 wherein the at least one acidic group or salt thereof is a carboxy group.

Embodiment 14 is the article of any one of embodiments 1 through 13 wherein the spacer group in the first and/or second plurality of pendant groups of the copolymer or in the first and/or second monomer is a catenated heteroatom-containing hydrocarbon group.

Embodiment 15 is the article of any one of embodiments 1 through 14 wherein the spacer group in the first and/or second plurality of pendant groups of the copolymer or in the first and/or second monomer comprises at least one hydrogen bonding moiety.

Embodiment 16 is the article of embodiment 15 wherein the hydrogen bonding moiety is selected from a carbonylimino moiety, a thiocarbonylimino moiety, an iminocarbonylimino group, an iminothiocarbonylimino moiety, an oxycarbonylimino moiety, an oxythiocarbonylimino moiety, and a combination thereof.

Embodiment 17 is the article of embodiment 16 wherein the hydrogen bonding moiety is selected from a carbonylimino moiety, an iminocarbonylimino group, an oxycarbonylimino moiety, and a combination thereof.

Embodiment 18 is the article of any one of embodiments 1 through 17 wherein the chain of the spacer group in the first and/or second plurality of pendant groups of the copolymer or in the first and/or second monomer has at least 7 catenated atoms.

Embodiment 19 is the article of embodiment 18 wherein the chain of the spacer group in the first and/or second plurality of pendant groups of the copolymer or in the first and/or second monomer has at least 8 catenated atoms.

Embodiment 20 is the article of any one of embodiments 1 through 19 wherein the chain of the spacer group in the first and/or second plurality of pendant groups of the copolymer or in the first and/or second monomer has no more than 50 catenated atoms.

Embodiment 21 is the article of embodiment 19 or 20 wherein the chain of the spacer group has from 9 to 16 catenated atoms.

Embodiment 22 is the article of any one of embodiments 2 through 21, as dependent on embodiment 2, wherein the first monomer is one of a class represented by the following general formula:

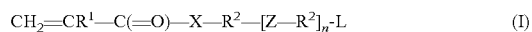

$$CH_2=CR^1-C(=O)-X-R^2-[Z-R^2]_n-L \qquad (I)$$

wherein:
$R^1$ is selected from hydrogen, an alkyl group, a cycloalkyl group, an aryl group, and a combination thereof;
each $R^2$ is independently selected from a hydrocarbylene group, a heterohydrocarbylene group, and a combination thereof;
X is —O— or —$NR^3$—, where $R^3$ is selected from hydrogen, a hydrocarbyl group, a heterohydrocarbyl group, and a combination thereof;
Z is a heterohydrocarbylene group comprising at least one hydrogen bond donor, at least one hydrogen bond acceptor, or a combination thereof;
n is an integer of 0 or 1; and
L is a functional group comprising at least one acidic group or salt thereof.

Embodiment 23 is the article of embodiment 22 wherein $R^1$ is selected from hydrogen, methyl, and a combination thereof.

Embodiment 24 is the article of any one of embodiments 2 through 23, as dependent on embodiment 2, wherein the second monomer is one of a class represented by the following general formula:

$$CH_2=CR^1—C(=O)—X—R^2—[Z—R^2]_n-L \quad (I)$$

wherein:
- $R^1$ is selected from hydrogen, an alkyl group, a cycloalkyl group, an aryl group, and a combination thereof;
- each $R^2$ is independently selected from a hydrocarbylene group, a heterohydrocarbylene group, and a combination thereof;
- X is —O— or —NR³—, where $R^3$ is selected from hydrogen, a hydrocarbyl group, a heterohydrocarbyl group, and a combination thereof;
- Z is a heterohydrocarbylene group comprising at least one hydrogen bond donor, at least one hydrogen bond acceptor, or a combination thereof;
- n is an integer of 0 or 1; and
- L is a functional group comprising at least one acidic group or salt thereof.

Embodiment 25 is the article of embodiment 24 wherein $R^1$ is selected from hydrogen, methyl, and a combination thereof.

Embodiment 26 is the article of any one of embodiments 22 through 25 wherein the at least one monomer is selected from:

VDM-4-aminobutyric acid (VDM-GABA):

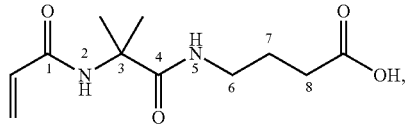

VDM-Phenylalanine:

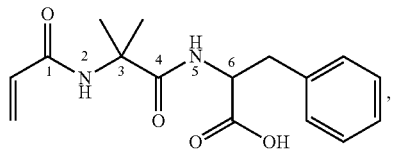

IEM-4-aminobutyric acid (IEM-GABA):

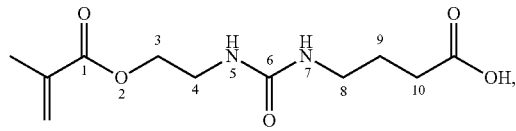

IEM-Phenylalanine:

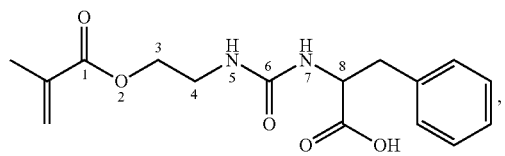

VDM-4-aminomethyl-cyclohexanecarboxylic acid:

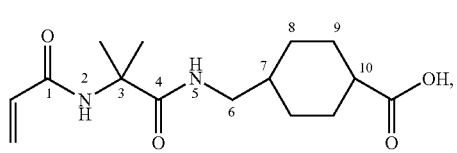

IEM-Glycine:

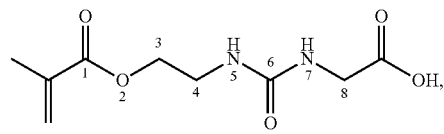

IEM-Taurine:

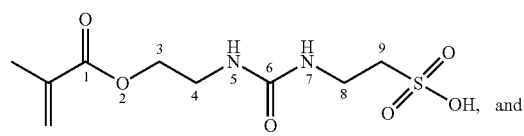

VDM-Taurine:

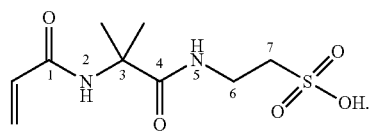

Embodiment 27 is the article of embodiment 26 wherein the copolymer is prepared from monomers:

Monomer 1: VDM-4-aminobutyric acid (VDM-GABA)

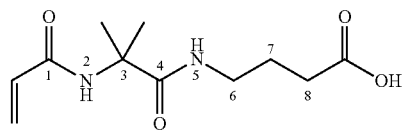

Monomer 2: VDM-Phenylalanine

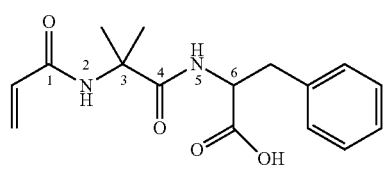

Embodiment 28 is the article of embodiment 26 wherein the copolymer is prepared from monomers:

Monomer 1: IEM-4-aminobutyric acid (IEM-GABA)

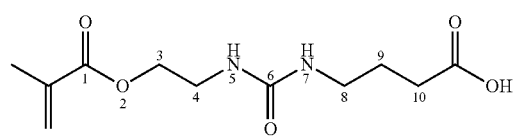

Monomer 2: IEM-Phenylalanine

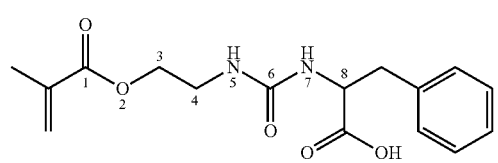

Embodiment 29 is the article of embodiment 26 wherein the copolymer is prepared from monomers:

Monomer 1: VDM-4-aminobutyric acid (VDM-GABA)

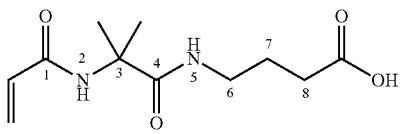

Monomer 2: VDM-4-aminomethyl-cyclohexanecarboxylic acid

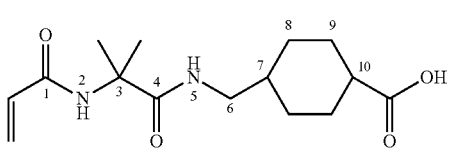

Embodiment 30 is the article of embodiment 26 wherein the copolymer is prepared from monomers:

Monomer 1: IEM-Glycine

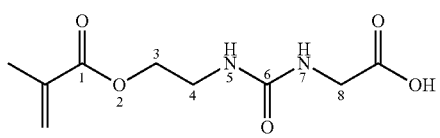

Monomer 2: IEM-Phenylalanine

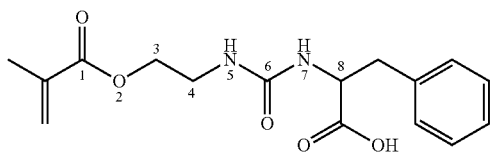

Embodiment 31 is the article of embodiment 26 wherein the copolymer is prepared from monomers:

Monomer 1: IEM-Glycine

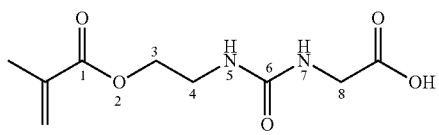

Monomer 2: VDM-Phenylalanine

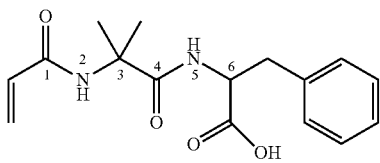

Embodiment 32 is the article of embodiment 26 wherein the copolymer is prepared from monomers:

Monomer 1: IEM-Taurine

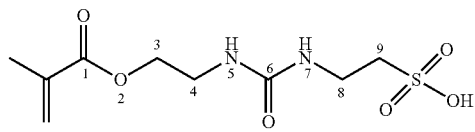

Monomer 2: IEM-Phenylalanine

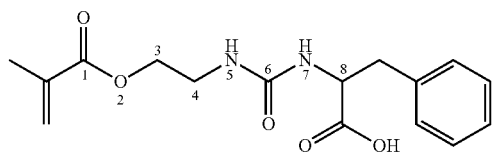

Embodiment 33 is the article of embodiment 26 wherein the copolymer is prepared from monomers:

Monomer 1: VDM-Taurine

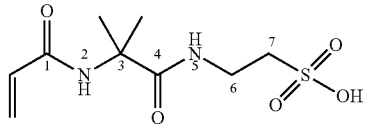

Monomer 2: VDM-Phenylalanine

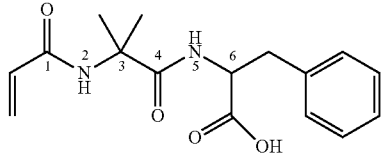

Embodiment 34 is the article of any one of embodiments 1 through 33 wherein a mole ratio of the first plurality of pendant groups to the second plurality of pendant groups or a mole ratio of the first monomer to the second monomer is in a range of 90:10 to 10:90.

Embodiment 35 is the article of any one of embodiments 2 through 34, as dependent on embodiment 2, wherein the reaction product of a monomer composition further comprises a hydrophilic modifying comonomer comprising at least one alkenyl group and at least one hydrophilic group.

Embodiment 36 is the article of embodiment 35 wherein the hydrophilic modifying comonomer is selected from acrylamide, dimethylacrylamide, hydroxyethyl(meth)acrylate, hydroxypropyl(meth)acrylate, polyethyleneglycolmono(meth)acrylate, 2-hydroxyethylacrylamide, N-vinylpyrrolidone, and a combination thereof.

Embodiment 37 is the article of any one of embodiments 2 through 36, as dependent on embodiment 2, wherein the reaction product of a monomer composition further comprises a modifying multifunctional (meth)acryloyl comonomer comprising at least two free radically polymerizable groups.

Embodiment 38 is the article of embodiment 37 wherein the multifunctional (meth)acryloyl comonomer is selected from a di(meth)acrylate, a tri(meth)acrylate, a tetra(meth)acrylate, a multifunctional (meth)acrylamide, and a combination thereof.

Embodiment 39 is the article of embodiment 38 wherein the modifying multifunctional (meth)acryloyl comonomer is selected from ethyleneglycol di(meth)acrylate, 1,6-hexanediol di(meth)acrylate, poly(ethylene glycol) di(meth)acrylates, polybutadiene di(meth)acrylate, polyurethane di(meth)acrylates, propoxylated glycerin tri(meth)acrylate, methylenebisacrylamide, ethylenebisacrylamide, hexamethylenebisacrylamide, diacryloylpiperazine, and a combination thereof.

Embodiment 40 is the article of any one of embodiments 1 through 39 which is a filter element having a contacting surface (e.g., an upstream or upper surface).

Embodiment 41 is an array of sample containers, wherein each container includes the filter element of embodiment 40.

Embodiment 42 is a process for capture or removal of a target biomaterial comprising:
  providing a filter element of embodiment 40 or an array of embodiment 41; and
  allowing a biological solution comprising a target biomaterial to contact the contacting surface (e.g., upstream or upper surface) of the filter element under conditions effective for binding of the target biomaterial.

Embodiment 43 is the process of embodiment 42 wherein the target biomaterial comprises a protein.

Embodiment 44 is the process of embodiment 43 wherein the protein is an antibody, enzyme, or hormone.

Embodiment 45 is the process of embodiment 44 wherein the protein is an antibody.

Embodiment 46 is the process of embodiment 45 wherein the antibody is a monomeric antibody and the biological solution comprises monomeric and aggregated antibodies, and further wherein the biological solution contacts the contacting surface (e.g., upstream or upper surface) of the filter element under conditions effective for binding the aggregated antibodies and passage of the monomeric antibodies.

Embodiment 47 is a process for separating aggregated proteins from monomeric proteins in a biological solution, the process comprising:
  providing at least one filter element having a contacting surface (e.g., an upstream or upper surface), wherein the filter element comprises filter media comprising:
    a) a porous substrate; and
    b) a copolymer covalently attached to the porous substrate, the copolymer comprising a hydrocarbon backbone and a plurality of pendant groups attached to the hydrocarbon backbone, wherein:
      1) each of a first plurality of pendant groups comprises:
        (a) at least one acidic group or salt thereof; and
        (b) a spacer group that directly links the at least one acidic group or salt thereof to the hydrocarbon backbone by a chain of at least 6 catenated atoms; and
      2) each of a second plurality of pendant groups comprises:
        (a) at least one acidic group or salt thereof; and
        (b) a spacer group that directly links the at least one acidic group or salt thereof to the hydrocarbon backbone by a chain of at least 6 catenated atoms; and
      wherein the first plurality of pendant groups are different than the second plurality of pendant groups; and
      wherein a mole ratio of the first plurality of pendant groups to the second plurality of pendant groups is in a range of 95:5 to 5:95; and
  allowing an initial biological solution to contact the contacting solution (e.g., upstream or upper surface) of the filter element under conditions effective to separate the aggregated proteins from the monomeric proteins such that that a final biological solution includes purified monomeric proteins.

Embodiment 48 is a process for separating aggregated proteins from monomeric proteins in a biological solution, the process comprising:
  providing at least one filter element having a contacting surface (e.g., an upstream or upper surface), wherein the filter element comprises filter media comprising:
    a) a porous substrate; and
    b) a copolymer covalently attached to the porous substrate, the copolymer comprising a reaction product of a monomer composition comprising:
      1) a first monomer comprising (in some embodiments, consisting of):
        (a) at least one ethylenically unsaturated group (in some embodiments, a terminal ethylenically unsaturated group);
        (b) at least one acidic group or salt thereof; and
        (c) a spacer group that directly links the at least one ethylenically unsaturated group and the at least one acidic group or salt thereof by a chain of at least 6 catenated atoms; and
      2) a second monomer comprising (in some embodiments, consisting of):
        (a) at least one ethylenically unsaturated group (in some embodiments, a terminal ethylenically unsaturated group);
        (b) at least one acidic group or salt thereof; and
        (c) a spacer group that directly links the at least one ethylenically unsaturated group and the at least one acidic group or salt thereof by a chain of at least 6 catenated atoms;
      wherein the second monomer is different than the first monomer; and
      wherein a mole ratio of the first monomer to the second monomer is in a range of 95:5 to 5:95; and
  allowing an initial biological solution to contact the contacting surface (e.g., upstream or upper surface) of the filter element under conditions effective to separate the aggregated proteins from the monomeric proteins such that a final biological solution includes purified monomeric proteins.

Embodiment 49 is the process of embodiment 47 or 48 further comprising recovering the monomeric proteins without eluting.

Embodiment 50 is the process of any one of embodiments 47 through 49 wherein the conditions are effective to recover, in a final solution, at least 40%, or at least 45%, or at least 50%, or at least 55%, or at least 60%, or at least 65%, or at least 70%, or at least 75%, or at least 80%, or at least 85%, or at least 90%, or at least 95%, of the monomeric proteins present in the initial biological solution.

Embodiment 51 is the process of any one of embodiments 47 through 50 wherein the conditions are effective to remove at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, of the aggregated proteins from the initial biological solution.

Embodiment 52 is the process of any one of embodiments 47 through 51 wherein the proteins comprise antibodies, enzymes, or hormones.

Embodiment 53 is the process of embodiment 52 wherein the proteins comprise antibodies.

Embodiment 54 is the process of embodiment 53 wherein the antibodies comprise monoclonal antibodies.

Embodiment 55 is the process of any one of embodiments 47 through 54 wherein the conditions comprise a pH of the biological solution of below 9, or below 8.5, or below 8, or below 7.5, or below 7, or below 6.5.

Embodiment 56 is the process of any one of embodiments 47 through 55 wherein the conditions comprise a pH of the biological solution of at least 4, or at least 4.5, or at least 5.

Embodiment 57 is the process of any one of embodiments 47 through 56 wherein the conditions comprise a conductivity of the biological solution of at least 1 mS/cm, or at least 2 mS/cm, or at least 3 mS/cm, or at least 4 mS/cm, or at least 5 mS/cm, or at least 6 mS/cm, or at least 7 mS/cm, or at least 8 mS/cm, or at least 9 mS/cm, or at least 10 mS/cm.

Embodiment 58 is the process of embodiment 57 wherein the conductivity of the biological solution is provided by a buffer comprising an inorganic salt, organic salt, or a combination thereof.

Embodiment 59 is the process of embodiment 58 wherein the buffer salt comprises a chloride (e.g., NaCl), a phosphate, a citrate, a sulfate, an acetate, or a combination thereof.

Embodiment 60 is the process of any one of embodiments 47 through 59 wherein the conditions comprise a conductivity of the biological solution of no greater than 110 mS/cm, or no greater than 100 mS/cm, or no greater than 50 mS/cm, or no greater than 40 mS/cm, or no greater than 30 mS/cm.

Embodiment 61 is the process of any one of embodiments 47 through 60 wherein the conditions comprise a challenge load of at least 1 g/L of filter media, or at least 10 g/L of filter media, or at least 25 g/L of filter media, or at least 50 g/L of filter media, or at least 75 g/L of filter media, or at least 100 g/L, or at least 500 g/L, or at least 1000 g/L, or at least 2000 g/L, of filter media.

EXAMPLES

Objects and advantages of this disclosure are further illustrated by the following examples, but the particular materials and amounts thereof recited in these examples, as well as other conditions and details, should not be construed to unduly limit this disclosure. These examples are merely for illustrative purposes only and are not meant to be limiting on the scope of the appended claims.

Materials:

TABLE 1

| Materials | |
|---|---|
| Description (abbreviation) | Source |
| Sodium phosphate (monobasic and dibasic) | J T Baker, Phillipsburg, NJ |
| Tris(hydroxymethyl)-aminomethane (Tris) | Alfa Aesar, Ward Hill, MA |
| Sodium citrate | Alfa Aesar, Ward Hill, MA |
| Citric acid | Alfa Aesar, Ward Hill, MA |
| Vinyldimethylazlactone (VDM) | SNPE, Inc., Princeton, NJ |
| 2-Isocyanatoethyl methacrylate (IEM) | Showa Denko KK, Kanagawa, Japan |
| 4-(3-Sulfopropyloxy)benzophenone, sodium salt (S-BP) | Described in Japanese Patent No. 47040913 (Teijin Ltd.) |

IgG Antibody Solution Preparation:

Monoclonal antibody IgG (33.2 mg/mL, 3-4% aggregate content, pI>8, pH 5.3, 3.0 mS/cm) was diluted either 10-fold or 40-fold with a 20 mM buffer solution of citrate (pH 5 and 6), sodium phosphate (pH 7), or Tris (pH 8). The resulting buffer solutions were adjusted with sodium chloride to have conductivities ranging between 1.5-105 mS/cm. The conductivity and pH measurements of the IgG-containing buffer solutions were determined using an Accumet Excel XL50 conductivity meter (Fisher Scientific, Hampton, N H) and a VWR sympHony™ benchtop pH meter (VWR, Radnor, Pa.), respectively. In Table 2, the buffer, pH and conductivity for each of the IgG-containing buffer solutions (IgG Solution Numbers 1-20) are recorded.

TABLE 2

| IgG-containing solutions used for examples | | | |
|---|---|---|---|
| IgG Solution Number | Buffer (20 mM) | pH | Conductivity (mS/cm) |
| 1 | Citrate | 5 | 3.4 |
| 2 | Citrate | 5 | 10.5 |
| 3 | Citrate | 5 | 22.1 |
| 4 | Citrate | 5 | 35.0 |
| 5 | Citrate | 5 | 99.7 |
| 6 | Citrate | 6 | 2.8 |
| 7 | Citrate | 6 | 9.9 |
| 8 | Citrate | 6 | 20.5 |
| 9 | Citrate | 6 | 36.8 |
| 10 | Citrate | 6 | 98.3 |
| 11 | Phosphate | 7 | 3.0 |
| 12 | Phosphate | 7 | 10.2 |
| 13 | Phosphate | 7 | 20.4 |
| 14 | Phosphate | 7 | 36.2 |
| 15 | Phosphate | 7 | 101.4 |
| 16 | Tris | 8 | 2.1 |
| 17 | Tris | 8 | 9.6 |
| 18 | Tris | 8 | 21.1 |
| 19 | Tris | 8 | 35.5 |
| 20 | Tris | 8 | 97.5 |

Monomer Preparation

Monomer Example A

4-[[2-Methyl-2-(Prop-2-Enoylamino)Propanoyl]Amino]Butanoic Acid, Sodium Salt (VDM-GABA, Sodium Salt)

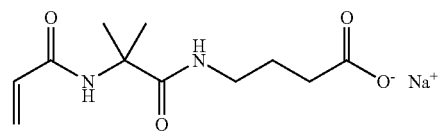 [SMILES: C=CC(=O)NC(C)(C)C(=O)NCCCC(=O)[O-] ; [Na+]]

4-Aminobutanoic acid (2.06 g, 0.02 mol) was added to a 100 mL round bottom flask. An aqueous solution of sodium hydroxide (1.0 N, 20 mL) was added to the flask and the resulting mixture was stirred until the solids dissolved. The flask was then placed in an ice-water bath and stirred for 15 minutes. VDM (2.78 g, 0.02 mol) was added by syringe and the reaction was stirred for 30 minutes with the flask continuously maintained in the ice-water bath. The cooling bath was then removed and the reaction was allowed to warm to room temperature over a period of 30 minutes. The pH of the reaction was adjusted to about 7 by the addition of a few drops of a concentrated hydrochloric acid solution. ¹H-NMR of an aliquot confirmed the formation of 4-[[2-methyl-2-(prop-2-enoylamino)propanoyl]amino]butanoic acid, sodium salt. ¹H-NMR (D₂O, 500 MHz) δ 1.34 (s, 6H), 1.59 (p, 2H), 2.04 (t, 2H), 3.05 (t, 2H), 5.62 (d, 1H), 6.0-6.2 (m, 2H).

Monomer Example B

4-[2-(2-Methylprop-2-enoyloxy)ethylcarbamoylamino]butanoic Acid, Sodium Salt (IEM-GABA, Sodium Salt)

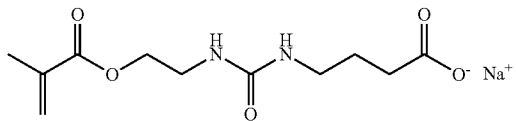 [SMILES: C=C(C)C(=O)OCCNC(=O)NCCCC(=O)[O-] ; [Na+]]

4-Aminobutanoic acid (2.06 g, 0.02 mol) was added to a 100 mL round bottom flask. An aqueous solution of sodium hydroxide (1.0 N, 20 mL) was added to the flask and the resulting mixture was stirred until the solids dissolved. The flask was then placed in an ice-water bath and stirred for 15 minutes. IEM (3.1 g, 0.02 mol) was added by syringe and the reaction was stirred for 30 minutes with the flask continuously maintained in the ice-water bath. The cooling bath was then removed and the reaction was allowed to warm to room temperature over a period of 30 minutes. A colorless precipitate was filtered from the reaction mixture. The pH of the filtrate was adjusted to about 7 by the addition of a few drops of a concentrated hydrochloric acid solution. ¹H-NMR of an aliquot of the filtrate confirmed the formation of 4-[2-(2-methylprop-2-enoyloxy)ethylcarbamoylamino]butanoic acid, sodium salt. ¹H-NMR (D₂O, 500 MHz) δ 1.57 (t, 2H), 1.78 (s, 3H), 2.05 (t, 2H), 2.95 (m, 2H), 3.31 (m, 2H), 4.08 (m, 2H), 5.58 (s 1H), 5.99 (s, 1H).

Monomer Example C

2-[[2-Methyl-2-(prop-2-enoylamino)propanoyl]amino]-3-phenylpropanoic Acid, Sodium Salt (VDM-Phenylalanine, Sodium Salt)

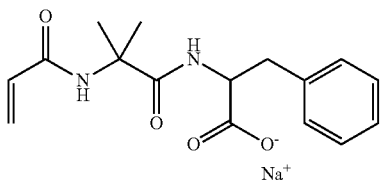 [SMILES: C=CC(=O)NC(C)(C)C(=O)NC(Cc1ccccc1)C(=O)[O-] ; [Na+]]

L-Phenylalanine (3.3 g, 0.02 mol) was added to a 100 mL round bottom flask. An aqueous solution of sodium hydroxide (1.0 N, 20 mL) was added to the flask and the resulting mixture was stirred until the solids dissolved. The flask was then placed in an ice-water bath and stirred for 15 minutes. VDM (2.78 g, 0.02 mol) was added by syringe and the reaction was stirred for 30 minutes with the flask continuously maintained in the ice-water bath. The cooling bath was then removed and the reaction was allowed to warm to room temperature over a period of 30 minutes. The pH of the reaction was adjusted to about 7 by the addition of a few drops of a concentrated hydrochloric acid solution. ¹H-NMR of an aliquot confirmed the formation of 2-[[2-methyl-2-(prop-2-enoylamino)propanoyl]amino]-3-phenylpropanoic acid, sodium salt. ¹H-NMR (D₂O, 500 MHz) δ 1.26 (s, 6H), 2.89 (m, 1H), 2.95 (m, 1H), 4.30 (m, 1H), 5.62 (d, 1H), 6.00-6.10 (m, 2H), 7.07-7.20 (m, 5H).

Monomer Example D

2-[2-(2-Methylprop-2-enoyloxy)ethylcarbamoylamino]-3-phenylpropanoic Acid, Sodium Salt (IEM-Phenylalanine, Sodium Salt)

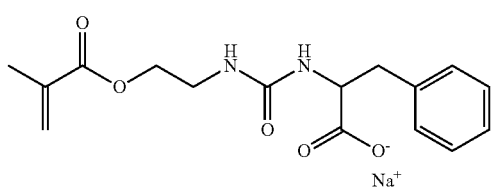 [SMILES: C=C(C)C(=O)OCCNC(=O)NC(Cc1ccccc1)C(=O)[O-] ; [Na+]]

L-Phenylalanine (3.3 g, 0.02 mol) was charged to a 100 mL round bottom flask. An aqueous solution of sodium hydroxide (1.0 N, 20 mL) was added to the flask and the resulting mixture was stirred until the solids dissolved. The flask was then placed in an ice-water bath and stirred for 15 minutes. IEM (3.1 g, 0.02 mol) was added by syringe and the reaction was stirred for 30 minutes with the flask continuously maintained in the ice-water bath. The cooling bath was then removed and the reaction was allowed to warm to room temperature over a period of 30 minutes. A colorless precipitate was filtered from the reaction mixture. The pH of the reaction was adjusted to about 7 by the addition of a few drops of a concentrated hydrochloric acid solution. ¹H-NMR of an aliquot of the filtrate ¹H-NMR of an aliquot confirmed the formation of 2-[2-(2-methylprop-2-enoyloxy)ethylcarbamoylamino]-3-phenylpropanoic acid, sodium salt. ¹H-NMR (D₂O, 500 MHz) δ 1.74 (br. s, 3H), 2.73 (m, 1H), 2.99 (m, 1H), 3.13 (m, 1H), 3.26 (m 1H), 3.90 (m, 2H), 4.17 (m, 1H), 5.54 (m, 1H), 5.95 (m, 1H), 7.09 and 7.15 (m, 5H).

Monomer Example E

2-[2-(2-Methylprop-2-enoyloxy)ethylcarbamoylamino]ethanoic Acid, Sodium Salt (IEM-Glycine, Sodium Salt)

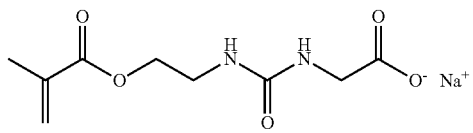 [SMILES: C=C(C)C(=O)OCCNC(=O)NCC(=O)[O-] ; [Na+]]

Glycine (1.5 g, 0.02 mol) was charged to a 100 mL round bottom flask. An aqueous solution of sodium hydroxide (1.0 N, 20 mL) was added to the flask and the resulting mixture was stirred until the solids dissolved. The flask was then placed in an ice-water bath and stirred for 15 minutes. IEM (3.1 g, 0.02 mol) was added by syringe and the reaction was stirred for 30 minutes with the flask continuously maintained in the ice-water bath. The cooling bath was then removed and the reaction was allowed to warm to room temperature over a period of 30 minutes. A colorless precipitate was filtered from the reaction mixture. The pH of the reaction was adjusted to about 7 by the addition of a few drops of a concentrated hydrochloric acid solution. ¹H-NMR of an aliquot of the filtrate confirmed the formation of 2-[2-(2-methylprop-2-enoyloxy)ethylcarbamoylamino]ethanoic acid, sodium salt. ¹H-NMR (D$_2$O, 500 MHz) δ 1.79 (s, 3H), 3.33 (m, 2H), 3.54 (s, 2H), 4.09 (m, 2H), 5.59 (s, 1H), 5.99 (s, 1H).

Monomer Example F

4-[[[2-Methyl-2-(prop-2-enoylamino)propanoyl]amino]methyl]cyclohexanecarboxylic Acid, Sodium Salt (VDM-4-Aminomethyl-Cyclohexanecarboxylic Acid, Sodium Salt)

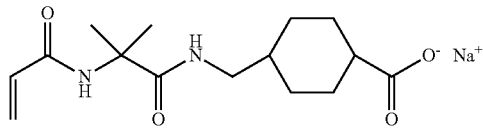 [SMILES: C=CC(=O)NC(C)(C)C(=O)NCC1CCC(C(=O)[O-])CC1 ; [Na+]]

Trans-4-Aminomethyl-cyclohexanecarboxylic acid (2.00 g, 0.013 mol) was added to a 100 mL round bottom flask. An aqueous solution of sodium hydroxide (1.0 N, 13 mL) was added to the flask and the resulting mixture was stirred until the solids dissolved. The flask was then placed in an ice-water bath and stirred for 15 minutes. 2-Vinyl-4,4-dimethylazlactone (VDM) (1.77 g, 1.7 mL, 0.013 mol) was added by syringe and the reaction was stirred for 30 minutes with the flask continuously maintained in the ice-water bath. The cooling bath was then removed and the reaction was allowed to warm to room temperature over a period of 30 minutes. The pH of the reaction was adjusted to about 7 by the addition of a few drops of a concentrated hydrochloric acid solution. ¹H-NMR of an aliquot confirmed the formation of 4-[[[2-methyl-2-(prop-2-enoylamino)propanoyl]amino]methyl]cyclohexanecarboxylic acid, sodium salt. ¹H-NMR (D$_2$O, 500 MHz) δ 0.89 (q, 2H), 1.27 (q, 2H), 1.42 (s, 6H), 1.43 (m, 1H), 1.69 (d, 2H), 1.82 (d, 2H), 2.03 (m, 1H), 2.98 (d, 2H), 5.72 (m, 1H), 6.14 (m, 1H), 6.23 (m, 1H).

Monomer Example G

2-[2-(2-Methylprop-2-enoyloxy)ethylcarbamoylamino]ethanesulfonic Acid, Sodium Salt (IEM-Taurine, Sodium Salt)

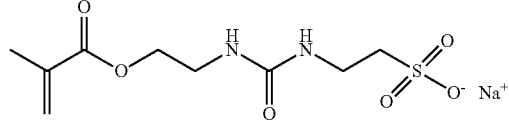 [SMILES: C=C(C)C(=O)OCCNC(=O)NCCS(=O)(=O)[O-] ; [Na+]]

Taurine (2.50 g, 0.02 mol) was added to a 100 mL round bottom flask. An aqueous solution of sodium hydroxide solution (1.0 N, 20 mL) was added to the flask and the resulting mixture was stirred until the solids dissolved. The flask was then placed in an ice-water bath and stirred for 15 minutes. IEM (3.1 g, 0.02 mol) was added by syringe and the reaction was stirred for 30 minutes with the flask continuously maintained in the ice-water bath. The cooling bath was then removed and the reaction was allowed to warm to room temperature over a period of 30 minutes. A colorless precipitate was filtered from the reaction mixture. The pH of the reaction was adjusted to about 7 by the addition of a few drops of a concentrated hydrochloric acid solution. ¹H-NMR of an aliquot of the filtrate confirmed the formation of 2-[2-(2-methylprop-2-enoyloxy)ethylcarbamoylamino]ethanesulfonic acid, sodium salt. ¹H-NMR (D$_2$O, 500 MHz) δ 1.75 (s, 3H), 2.88 (t, 2H), 3.28 (t, 2H) 3.32 (t, 2H), 4.06 (t, 2H), 5.56 (m, 1H), 5.97 (s, 1H).

Monomer Example H

2-[[2-Methyl-2-(prop-2-enoylamino)propanoyl]amino]ethanesulfonic Acid, Sodium Salt (VDM-Taurine, Sodium Salt)

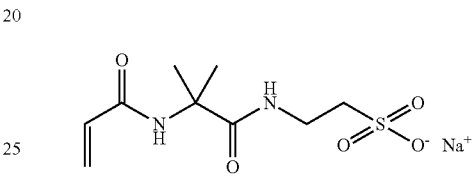

Taurine (2.50 g, 0.02 mol) was added to a 100 mL round bottom flask. An aqueous solution of sodium hydroxide solution (1.0 N, 20 mL) was added to the flask and the resulting mixture was stirred until the solids dissolved. The flask was then placed in an ice-water bath and stirred for 15 minutes. VDM (2.78 g, 0.02 mol) was added by syringe and the reaction was stirred for 30 minutes with the flask continuously maintained in the ice-water bath. The cooling bath was then removed and the reaction was allowed to warm to room temperature over a period of 30 minutes. The pH of the reaction was adjusted to about 7 by the addition of a few drops of a concentrated hydrochloric acid solution. ¹H-NMR of an aliquot confirmed the formation of 2-[[2-methyl-2-(prop-2-enoylamino)propanoyl]amino]ethanesulfonic acid, sodium salt. ¹H-NMR (D$_2$O, 500 MHz) δ 1.35 (s, 6H), 2.94 (t, 2H), 3.45 (t, 2H) 5.64 (m, 1H), 6.10 (m, 2H).

Example 1

A coating solution was prepared by mixing a solution of 4-[[2-methyl-2-(prop-2-enoylamino)propanoyl]amino]butanoic acid, sodium salt (monomer Example A) (3.75 mL of a 0.25M solution in deionized water) with 4-[[[2-methyl-2-(prop-2-enoylamino)propanoyl]amino]methyl]cyclohexanecarboxylic acid, sodium salt (monomer Example F) (1.25 mL of a 0.25M solution in deionized water), and the initiator 4-(3-sulfopropyloxy)benzophenone, sodium salt (S—BP) (31.2 μL of a 0.05 g/mL solution in deionized water). A nylon membrane substrate (9 cm×12 cm; nylon 66 membrane, single reinforced layer nylon three-zone membrane, nominal pore size 1.8 μm, #080ZN, obtained from 3M Purification, Inc., Meriden, Conn.) was placed on a sheet of clear polyester film (about 0.25 mm thick), and the coating solution was pipetted onto the top surface of the substrate. The coating solution was allowed to soak into the substrate for about 1 minute, and then a second sheet of clear polyester film (about 0.25 mm thick) was placed over the top surface of the substrate. A 2.28 kg cylindrical weight was rolled over the top of the resulting three-layer sandwich (polyester film-membrane substrate-polyester film) to squeeze out excess coating solution. Ultraviolet (UV)-initiated grafting was conducted by irradiating the sandwich using a UV stand (Classic Manufacturing, Inc., Oakdale, Minn.) equipped with 18 bulbs (Sylvania RG2 40W F40/350BL/ECO, 10 above and 8 below the substrate, 1.17 meters (46 inches) long, spaced 5.1 cm (2 inches) on center), with an irradiation time of 15 minutes. The polyester sheets were removed, and the remaining functionalized substrate was placed in a 250 mL polyethylene bottle. The bottle was filled with 0.9 percent (wt %) saline, sealed, and shaken for 30 minutes to wash off any residual monomer or ungrafted polymer. The saline was decanted, and the functionalized substrate was washed for another 30 minutes with fresh saline solution and then washed for 30 minutes with deionized water and allowed to dry. The finished filter element had a graft density of 0.18 mmol/gram. Graft density was determined by the measuring the mass gain after conversion of the substrate to the finished filter element.

Example 2

A coating solution was prepared by mixing a solution of 4-[[2-methyl-2-(prop-2-enoylamino)propanoyl]amino]butanoic acid, sodium salt (monomer Example A) (2.5 mL of a 0.25M solution in deionized water) with 4-[[[2-methyl-2-(prop-2-enoylamino)propanoyl]amino]methyl]cyclohexanecarboxylic acid, sodium salt (monomer Example F) (2.5 mL of a 0.25M solution in deionized water), and S—BP (31.2 μL of a 0.05 g/mL solution in deionized water). The procedure described in Example 1 was followed to provide a finished filter element with a graft density of 0.19 mmol/gram.

Example 3

A coating solution was prepared by mixing a solution of 4-[[2-methyl-2-(prop-2-enoylamino)propanoyl]amino]butanoic acid, sodium salt (monomer Example A) (1.25 mL of a 0.25M solution in deionized water) with 4-[[[2-methyl-2-(prop-2-enoylamino)propanoyl]amino]methyl]cyclohexanecarboxylic acid, sodium salt (monomer Example F) (3.75 mL of a 0.25M solution in deionized water), and S—BP (31.2 μL of a 0.05 g/mL solution in deionized water). The procedure described in Example 1 was followed to provide a finished filter element with a graft density of 0.20 mmol/gram.

Example 4

A coating solution was prepared by mixing a solution of 4-[[2-methyl-2-(prop-2-enoylamino)propanoyl]amino]butanoic acid, sodium salt (monomer Example A) (3.75 mL of a 0.25M solution in deionized water) with 2-[[2-methyl-2-(prop-2-enoylamino)propanoyl]amino]-3-phenylpropanoic acid, sodium salt (monomer Example C) (1.25 mL of a 0.25M solution in deionized water), and S—BP (31.2 μL of a 0.05 g/mL solution in deionized water). The procedure described in Example 1 was followed to provide a finished filter element with a graft density of 0.20 mmol/gram.

Example 5

A coating solution was prepared by mixing a solution of 4-[[2-methyl-2-(prop-2-enoylamino)propanoyl]amino]butanoic acid, sodium salt (monomer Example A) (2.5 mL of a 0.25M solution in deionized water) with 2-[[2-methyl-2-(prop-2-enoylamino)propanoyl]amino]-3-phenylpropanoic acid, sodium salt (monomer Example C) (2.5 mL of a 0.25M solution in deionized water), and S—BP (31.2 μL of a 0.05 g/mL solution in deionized water). The procedure described in Example 1 was followed to provide a finished filter element with a graft density of 0.18 mmol/gram.

Example 6

A coating solution was prepared by mixing a solution of 4-[[2-methyl-2-(prop-2-enoylamino)propanoyl]amino]butanoic acid, sodium salt (monomer Example A) (4.5 mL of a 0.25M solution in deionized water) with 2-[[2-methyl-2-(prop-2-enoylamino)propanoyl]amino]-3-phenylpropanoic acid, sodium salt (monomer Example C) (0.5 mL of a 0.25M solution in deionized water), and S—BP (31.2 μL of a 0.05 g/mL solution in deionized water). The procedure described in Example 1 was followed to provide a finished filter element with a graft density of 0.18 mmol/gram.

Example 7

A coating solution was prepared by mixing a solution of 2-[2-(2-methylprop-2-enoyloxy)ethylcarbamoylamino]ethanoic acid, sodium salt (monomer Example E) (1.25 mL of a 0.25M solution in deionized water) with 2-[2-(2-methylprop-2-enoyloxy)ethylcarbamoylamino]-3-phenylpropanoic acid, sodium salt (monomer Example D) (3.75 mL of a 0.25M solution in deionized water), and S—BP (31.2 μL of a 0.05 g/mL solution in deionized water). The procedure described in Example 1 was followed to provide a finished filter element with a graft density of 0.28 mmol/gram.

Example 8

A coating solution was prepared by mixing a solution of 2-[2-(2-methylprop-2-enoyloxy)ethylcarbamoylamino]ethanoic acid, sodium salt (monomer Example E) (2.5 mL of a 0.25M solution in deionized water) with 2-[2-(2-methylprop-2-enoyloxy)ethylcarbamoylamino]-3-phenylpropanoic acid, sodium salt (monomer Example D) (2.5 mL of a 0.25M solution in deionized water), and S—BP (31.2 μL of a 0.05 g/mL solution in deionized water). The procedure described in Example 1 was followed to provide a finished filter element with a graft density of 0.32 mmol/gram.

Example 9

A coating solution was prepared by mixing a solution of 2-[2-(2-methylprop-2-enoyloxy)ethylcarbamoylamino]butanoic acid, sodium salt (monomer Example B) (3.75 mL of a 0.25M solution in deionized water) with 2-[2-(2-methylprop-2-enoyloxy)ethylcarbamoylamino]-3-phenylpropanoic acid, sodium salt (monomer Example D) (1.25 mL of a 0.25M solution in deionized water), and S—BP (31.2 μL of a 0.05 g/mL solution in deionized water). The procedure described in Example 1 was followed to provide a finished filter element with a graft density of 0.29 mmol/gram.

Example 10

A coating solution was prepared by mixing a solution of 2-[2-(2-methylprop-2-enoyloxy)ethylcarbamoylamino]butanoic acid, sodium salt (monomer Example B) (2.5 mL of a 0.25M solution in deionized water) with 2-[2-(2-methylprop-2-enoyloxy)ethylcarbamoylamino]-3-phenylpropanoic acid, sodium salt (monomer Example D) (2.5 mL of a 0.25M solution in deionized water), and S—BP (31.2 µL of a 0.05 g/mL solution in deionized water). The procedure described in Example 1 was followed to provide a finished filter element with a graft density of 0.33 mmol/gram.

Example 11

A coating solution was prepared by mixing a solution of 2-[2-(2-methylprop-2-enoyloxy)ethylcarbamoylamino] ethanoic acid, sodium salt (monomer Example E) (2.5 mL of a 0.25M solution in deionized water) with 2-[[2-methyl-2-(prop-2-enoylamino)propanoyl]amino]-3-phenylpropanoic acid, sodium salt (monomer Example C) (2.5 mL of a 0.25M solution in deionized water), and S—BP (31.2 µL of a 0.05 g/mL solution in deionized water). The procedure described in Example 1 was followed to provide a finished filter element with a graft density of 0.14 mmol/gram.

Example 12

A coating solution was prepared by mixing a solution of 4-[[2-methyl-2-(prop-2-enoylamino)propanoyl]amino]butanoic acid, sodium salt (monomer Example A) (2.5 mL of a 0.20M solution in deionized water) with 4-[[[2-methyl-2-(prop-2-enoylamino)propanoyl]amino]methyl]cyclohexanecarboxylic acid, sodium salt (monomer Example F) (2.5 mL of a 0.20M solution in deionized water), and S—BP (31.2 µL of a 0.05 g/mL solution in deionized water). The procedure described in Example 1 was followed to provide a finished filter element with a graft density of 0.12 mmol/gram.

Example 13

A coating solution was prepared by mixing a solution of 2-[2-(2-methylprop-2-enoyloxy)ethylcarbamoylamino]ethanesulfonic acid, sodium salt (monomer Example H) (2.5 mL of a 0.25M solution in deionized water) with 2-[[2-methyl-2-(prop-2-enoylamino)propanoyl]amino]-3-phenylpropanoic acid, sodium salt (monomer Example C) (2.5 mL of a 0.25M solution in deionized water), and S—BP (31.2 µL of a 0.05 g/mL solution in deionized water). The procedure described in Example 1 was followed to provide a finished filter element with a graft density of 0.18 mmol/gram.

Example 14

A coating solution was prepared by mixing a solution of 2-[2-(2-methylprop-2-enoyloxy)ethylcarbamoylamino]ethanesulfonic acid, sodium salt (monomer Example G) (2.5 mL of a 0.25M solution in deionized water) 2-[2-(2-methylprop-2-enoyloxy)ethylcarbamoylamino]-3-phenylpropanoic acid, sodium salt (monomer Example D) (2.5 mL of a 0.25M solution in deionized water), and S—BP (31.2 µL of a 0.05 g/mL solution in deionized water). The procedure described in Example 1 was followed to provide a finished filter element with a graft density of 0.40 mmol/gram.

Comparative Example a

The procedure for preparing a finished filter element described in Example 1 was followed with the exception that the coating solution contained only a single monomer (instead of two monomers). The coating solution was prepared by mixing a solution of 4-[[2-methyl-2-(prop-2-enoylamino)propanoyl]amino]butanoic acid, sodium salt (Monomer Example A) (1.53 grams of a 21.65% w/w solution in deionized water, 1.25 mmol) with S—BP (31.3 µL of a 0.05 g/mL solution in deionized water). This mixture was diluted to a total of 5 grams with deionized water to produce a final monomer concentration of 0.25M and initiator concentration of 0.031%. The resulting finished filter element had a graft density of 0.17 mmol/gram.

Comparative Example B

The procedure for preparing a finished filter element described in Example 1 was followed with the exception that the coating solution contained only a single monomer (instead of two monomers). The coating solution was prepared by mixing a solution of 4-[[[2-methyl-2-(prop-2-enoylamino)propanoyl]amino]methyl]cyclohexanecarboxylic acid, sodium salt (Monomer Example F) (1.67 grams of a 23.85% w/w solution in deionized water, 1.25 mmol) with S—BP (31.3 µL of a 0.05 g/mL solution in deionized water). This mixture was diluted to a total of 5 grams with deionized water to produce a final monomer concentration of 0.25M and initiator concentration of 0.031%. The resulting finished filter element had a graft density of 0.19 mmol/gram.

Comparative Example C

The procedure for preparing a finished filter element described in Example 1 was followed with the exception that the coating solution contained only a single monomer (instead of two monomers). The coating solution was prepared by mixing a solution of 2-[2-(2-methylprop-2-enoyloxy) ethylcarbamoylamino]-3-phenylpropanoic acid, sodium salt (Monomer Example D) (1.71 grams of a 25% w/w solution in deionized water, 1.25 mmol) with S—BP (31.2 µL of a 0.05 g/mL solution in deionized water). This mixture was diluted to a total of 5 grams with deionized water to produce a final monomer concentration of 0.25M and initiator concentration of 0.031%. The resulting finished filter element had a graft density of 0.42 mmol/gram.

Comparative Example D

The procedure for preparing a finished filter element described in Example 1 was followed with the exception that the coating solution contained only a single monomer (instead of two monomers). The coating solution was prepared by mixing a solution of 2-[[2-methyl-2-(prop-2-enoylamino) propanoyl]amino]-3-phenylpropanoic acid, sodium salt (monomer Example C) (1.65 grams of a 24.8% w/w solution in deionized water, 1.25 mmol) with S—BP (31.2 µL of a 0.05 g/mL solution in deionized water). This mixture was diluted to a total of 5 grams with deionized water to produce a final monomer concentration of 0.25M and initiator concentration of 0.031%. The resulting finished filter element had a graft density of 0.18 mmol/gram.

Comparative Example E

The procedure for preparing a finished filter element described in Example 1 was followed with the exception that the coating solution contained only a single monomer (instead of two monomers). The coating solution was prepared by mixing a solution of 2-[2-(2-methylprop-2-enoyloxy) ethylcarbamoylamino]ethanoic acid, sodium salt (monomer Example E) (1.62 grams of a 19.5% w/w solution in deionized water, 1.25 mmol) with S—BP (62.5 µL of a 0.05 g/mL solution in deionized water). This mixture was diluted to a total of 5 grams with deionized water to produce a final monomer concentration of 0.25M and initiator concentration of 0.0625%. The resulting finished filter element had a graft density of 0.25 mmol/gram.

Example 15. Process for Separating Aggregated IgG from Monomeric IgG

The finished filter elements of Examples 1-14 and Comparative Examples A-E were cut into 7.5 mm diameter disks. Two disks were inserted into each well of a 96-well EMPORE Filter Plate (Model 6065, 3M Corporation, St. Paul, Minn.) in which the original solid phase extraction material had been previously removed. The filter element disks were held in place with a plastic O-ring. The total working filter volume of each well was about 8.6 Each well was equilibrated with 1 mL of a non-IgG-containing buffer solution that had the same buffer composition as in the IgG-containing solution to be tested in the well. The equilibration solutions were removed from the wells using centrifugation (Allegra 25R centrifuge, Beckman Coulter, Brea, Calif.). The wells of the plate were then individually loaded (by pipet) with 1 mL of a single IgG-containing buffer solution selected from Table 2. The plate was sequentially centrifuged at 100, 200, 300, 600, 1200, and 3000 rcf (relative centrifugal force) or until the individual samples completely flowed through the filter elements. Each centrifugation step was conducted for about 5 minutes. The concentration of IgG in the IgG-containing buffer solution was either 3.32 mg/mL or 0.83 mg/mL, representing a challenge load of either 386 g/L or 96.5 g/L. Challenge load is defined as the amount of IgG per given volume of filtration media (grams per liter, g/L). Separate collection plates were used for the equilibration solutions and IgG sample solutions. Filtered solutions were analyzed by size exclusion chromatography (SEC) using a Shimadzu Prominence HPLC (Shimadzu Scientific Instruments, Columbia, Md.) with a TSKgel G3000SWx1 column (Tosoh Bioscience LLC, Griesheim, Germany) (analysis conditions: injection volume of 20 µL; flow rate of 1 ml/min; mobile phase: 100 mM sodium phosphate, 300 mM NaCl, pH 6.9; detection at 280 nanometers).

In Tables 3-21 the results are presented for the process of Example 15 using the filter elements (from Examples 1-14 and Comparative Examples A-E) and the IgG solutions (Numbers 1-20 described in Table 2). Monomer yield and aggregate removal were determined by comparison of peak areas of the starting and filtered solutions and the results are reported as the average of two replicates.

The percent of monomeric IgG present in the IgG solution before performing the separation process of Example 15 (Initial IgG solution) was determined using the SEC chromatography method described above. The peak area of the monomeric component (Peak A) of the sample was compared to the sum of the sample peak areas (Total Peak Area) according to Equation 1.

The percent of aggregated IgG present in the IgG solution before performing the separation process of Example 15 (Initial IgG solution) was determined using the SEC chromatography method described above. The peak area of the aggregate component (Peak B) of the sample was compared to the sum of the sample peak areas (Total Peak Area) according to Equation 2.

The ratio of the percent of monomeric IgG to the percent of aggregated IgG in the initial IgG solution (i.e. prior to performing the separation process of Example 15) was calculated according to Equation 3 and is reported as the "Initial Composition Ratio".

The percent removal of aggregated IgG was determined using the SEC chromatography method described above and measuring the peak area for the aggregated component before performing the separation process (Peak B) and after performing the separation process of Example 15 (Peak C). The "% Aggregated IgG Removed" was calculated according to Equation 4.

The percent yield of monomeric IgG was determined using the SEC chromatography method described above and measuring the peak area for the monomeric component before performing the separation process (Peak A) and after performing the separation process of Example 15 (Peak D). The "% Monomeric IgG Yield" was calculated according to Equation 5.

The calculation for Monomeric IgG Recovered following the separation process of Example 15 was determined according to Equation 6 and is reported as "Final Monomeric IgG Recovered (%)".

The calculation for Aggregated IgG Recovered following the separation process of Example 15 was determined according to Equation 7 and is reported as "Final Aggregated IgG Recovered (%)".

The ratio of the percent of monomeric IgG to the percent of aggregated IgG in the final IgG solution (i.e. after performing the separation process of Example 15) was calculated according to Equation 8 and is reported as the "Final Composition Ratio".

The "Ratio of the Final Composition Ratio to the Initial Composition Ratio" was calculated according to Equation 9.

The calculated values for Equations 1-9 are reported in Tables 3-21.

$$\text{Initial Monomeric } IgG\ (\%) = \left(\frac{\text{Peak Area } A}{\text{Total Peak Area}}\right) \times 100 \qquad \text{Equation 1}$$

$$\text{Initial Aggregated } IgG\ (\%) = \left(\frac{\text{Peak Area } B}{\text{Total Peak Area}}\right) \times 100 \qquad \text{Equation 2}$$

$$\text{Initial Composition Ratio} = \left(\frac{\text{Initial Monomeric } IgG\ (\%)}{\text{Initial Aggregated } IgG\ (\%)}\right) \qquad \text{Equation 3}$$

$$\text{Aggregated } IgG \text{ Removed } (\%) = 100 - \left(\left(\frac{\text{Peak Area } C}{\text{Peak Area } B}\right) \times 100\right) \qquad \text{Equation 4}$$

$$\text{Monomeric } IgG \text{ Yield } (\%) = \left(\frac{\text{Peak Area } D}{\text{Peak Area } A}\right) \times 100 \qquad \text{Equation 5}$$

$$\text{Final Monomeric } IgG \text{ Recovered } (\%) = \left(\frac{\text{Initial Monomeric } IgG\ (\%) \times \text{Monomeric } IgG \text{ Yield } (\%)}{100}\right) \qquad \text{Equation 6}$$

$$\text{Final Aggregated } IgG \text{ Recovered } (\%) = \text{Initial Aggregated } IgG\ (\%) \times \left(\frac{100 - \text{Aggregated } IgG \text{ Removed } (\%)}{100}\right) \qquad \text{Equation 7}$$

$$\text{Final Composition Ratio} = \left(\frac{\text{Final Monomeric } IgG \text{ Recovered } (\%)}{\text{Final Aggregated } IgG \text{ Recovered } (\%)}\right) \qquad \text{Equation 8}$$

$$\text{Ratio of Final Composition Ratio to Initial Composition Ratio} = \left(\frac{\text{Final Composition Ratio}}{\text{Initial Composition Ratio}}\right) \qquad \text{Equation 9}$$

TABLE 3

| | | | Filter Element of Example 1 | | | | | | |
|---|---|---|---|---|---|---|---|---|---|
| | | | | 386 g/L Challenge Load | | | | | |
| | | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 97.5 | 2.5 | 39.0 | 84.3 | 86.5 | 84.3 | 0.4 | 210.7 | 5.40 |
| 2 | 97.6 | 2.4 | 40.7 | 88.9 | 86.1 | 84.0 | 0.3 | 280.0 | 6.88 |
| 3 | 96.9 | 3.1 | 31.3 | 82.4 | 88.9 | 86.1 | 0.5 | 172.2 | 5.50 |
| 4 | 97.1 | 2.9 | 33.5 | 24.9 | 97.7 | 94.9 | 2.2 | 43.1 | 1.29 |
| 6 | 97.0 | 3.0 | 32.3 | 79.9 | 81.4 | 79.0 | 0.6 | 131.7 | 4.08 |
| 7 | 96.8 | 3.2 | 30.3 | 53.7 | 92.1 | 89.2 | 1.5 | 59.5 | 1.96 |
| 8 | 99.0 | 1.0 | 99.0 | 3.2 | 97.7 | 96.7 | 1.0 | 96.7 | 0.98 |
| 9 | 97.3 | 2.7 | 36.0 | 9.0 | 98.9 | 96.2 | 2.5 | 38.5 | 1.07 |
| 11 | 96.1 | 3.9 | 24.6 | 83.2 | 83.8 | 80.5 | 0.7 | 115.0 | 4.67 |
| 12 | 96.3 | 3.7 | 26.0 | 9.2 | 101.0 | 97.3 | 3.4 | 28.6 | 1.10 |
| 13 | 96.4 | 3.6 | 26.8 | 6.6 | 100.0 | 96.4 | 3.4 | 28.4 | 1.06 |
| 14 | 96.4 | 3.6 | 26.8 | 6.0 | 100.2 | 96.6 | 3.4 | 28.4 | 1.06 |
| 16 | 96.3 | 3.7 | 26.0 | 39.4 | 95.8 | 92.3 | 2.2 | 42.0 | 1.62 |
| 17 | 96.2 | 3.8 | 25.3 | 5.1 | 100.3 | 96.5 | 3.6 | 26.8 | 1.06 |
| 18 | 96.2 | 3.8 | 25.3 | 4.2 | 100.2 | 96.4 | 3.6 | 26.8 | 1.06 |
| 19 | 96.4 | 3.6 | 26.8 | 4.8 | 100 | 96.4 | 3.4 | 28.4 | 1.06 |

TABLE 4

| | | | Filter Element of Example 2 | | | | | | |
|---|---|---|---|---|---|---|---|---|---|
| | | | | 386 g/L Challenge Load | | | | | |
| | | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 97.5 | 2.5 | 39.0 | 53.6 | 93.6 | 91.3 | 1.2 | 76.1 | 1.95 |
| 2 | 97.6 | 2.4 | 40.7 | 74.5 | 86.7 | 84.6 | 0.6 | 141.0 | 3.46 |
| 3 | 96.9 | 3.1 | 31.3 | 76.8 | 89.6 | 86.8 | 0.7 | 124.0 | 3.96 |
| 4 | 97.1 | 2.9 | 33.5 | 62.6 | 94.0 | 91.3 | 1.1 | 83.0 | 2.48 |
| 6 | 97.0 | 3.0 | 32.3 | 73.2 | 80.5 | 78.1 | 0.8 | 97.6 | 3.02 |
| 7 | 96.8 | 3.2 | 30.3 | 87.9 | 86.0 | 83.2 | 0.4 | 208.0 | 6.86 |
| 8 | 99.0 | 1.0 | 99.0 | 4.5 | 98.0 | 97.0 | 1.0 | 97.0 | 0.98 |
| 9 | 97.3 | 2.7 | 36.0 | 6.6 | 100.0 | 97.3 | 2.5 | 38.9 | 1.08 |
| 11 | 96.1 | 3.9 | 24.6 | 86.9 | 76.0 | 73.0 | 0.5 | 146.0 | 5.93 |
| 12 | 96.3 | 3.7 | 26.0 | 10.8 | 99.5 | 95.8 | 3.3 | 29.0 | 1.11 |
| 13 | 96.4 | 3.6 | 26.8 | 5.9 | 99.3 | 95.7 | 3.4 | 28.1 | 1.05 |
| 14 | 96.4 | 3.6 | 26.8 | 3.9 | 99.3 | 95.7 | 3.5 | 27.3 | 1.02 |
| 16 | 96.3 | 3.7 | 26.0 | 47.4 | 96.0 | 92.4 | 1.9 | 48.6 | 1.87 |
| 17 | 96.2 | 3.8 | 25.3 | 5.4 | 99.4 | 95.6 | 3.6 | 26.5 | 1.05 |
| 18 | 96.2 | 3.8 | 25.3 | 2.9 | 99.2 | 95.4 | 3.7 | 25.8 | 1.02 |
| 19 | 96.4 | 3.6 | 26.8 | 1.6 | 99.7 | 96.1 | 3.5 | 27.4 | 1.02 |

TABLE 5

Filter Element of Example 3

386 g/L Challenge Load

| | | | | Filtration Performance | | Final | Final | | |
| --- | --- | --- | --- | --- | --- | --- | --- | --- | --- |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 97.5 | 2.5 | 39.0 | 14.9 | 96.9 | 94.5 | 2.1 | 45.0 | 1.15 |
| 2 | 97.6 | 2.4 | 40.7 | 29.6 | 93.8 | 91.5 | 1.7 | 53.8 | 1.32 |
| 3 | 96.9 | 3.1 | 31.3 | 34.8 | 93.5 | 90.6 | 2.0 | 45.3 | 1.45 |
| 4 | 97.1 | 2.9 | 33.5 | 36.2 | 95.0 | 92.2 | 1.9 | 48.5 | 1.45 |
| 6 | 97.0 | 3.0 | 32.3 | 67.2 | 79.2 | 76.8 | 1.0 | 76.8 | 2.28 |
| 7 | 96.8 | 3.2 | 30.3 | 88.8 | 81.1 | 78.5 | 0.4 | 196.3 | 6.48 |
| 8 | 99.0 | 1.0 | 99.0 | 8.7 | 96.9 | 95.9 | 0.9 | 106.5 | 1.08 |
| 9 | 97.3 | 2.7 | 36.0 | 8.1 | 99.4 | 96.7 | 2.5 | 38.7 | 1.08 |
| 11 | 96.1 | 3.9 | 24.6 | 86.4 | 78.4 | 75.3 | 0.5 | 150.6 | 6.12 |
| 12 | 96.3 | 3.7 | 26.0 | 12.4 | 100.2 | 96.5 | 3.2 | 30.2 | 1.16 |
| 13 | 96.4 | 3.6 | 26.8 | 5.1 | 100.2 | 96.6 | 3.4 | 28.4 | 1.06 |
| 14 | 96.4 | 3.6 | 26.8 | 2.7 | 100.2 | 96.6 | 3.5 | 27.6 | 1.03 |
| 16 | 96.3 | 3.7 | 26.0 | 62.1 | 94.5 | 91.0 | 1.4 | 65.0 | 2.50 |
| 17 | 96.2 | 3.8 | 25.3 | 4.0 | 101.4 | 97.5 | 3.6 | 27.1 | 1.07 |
| 18 | 96.2 | 3.8 | 25.3 | 3.2 | 100.8 | 97.0 | 3.7 | 26.2 | 1.04 |
| 19 | 96.4 | 3.6 | 26.8 | 1.8 | 100.8 | 97.2 | 3.5 | 27.8 | 1.04 |

TABLE 6

Filter Element of Example 4

386 g/L Challenge Load

| | | | | Filtration Performance | | Final | Final | | |
| --- | --- | --- | --- | --- | --- | --- | --- | --- | --- |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 97.3 | 2.7 | 36.0 | 83.8 | 79.6 | 77.5 | 0.4 | 193.7 | 5.38 |
| 2 | 97.3 | 2.7 | 36.0 | 63.7 | 81.9 | 79.7 | 1.0 | 79.7 | 2.21 |
| 3 | 97.2 | 2.8 | 34.7 | 88.5 | 87.1 | 84.7 | 0.3 | 282.3 | 8.14 |
| 4 | 97.4 | 2.6 | 37.5 | 55.7 | 94.6 | 92.1 | 1.2 | 76.8 | 2.05 |
| 5 | 97.5 | 2.5 | 39.0 | 14.4 | 96.1 | 93.7 | 2.1 | 44.6 | 1.14 |
| 6 | 97.3 | 2.7 | 36.0 | 71.1 | 75.9 | 73.9 | 0.8 | 92.4 | 2.57 |
| 7 | 97.2 | 2.8 | 34.7 | 90.2 | 81.6 | 79.3 | 0.3 | 264.3 | 7.62 |
| 8 | 97.4 | 2.6 | 37.5 | 26.8 | 97.6 | 95.1 | 1.9 | 50.1 | 1.34 |
| 9 | 97.5 | 2.5 | 39.0 | 16.1 | 97.4 | 95.0 | 2.1 | 45.2 | 1.16 |
| 10 | 97.5 | 2.5 | 39.0 | 8.0 | 98.2 | 95.7 | 2.3 | 41.6 | 1.07 |
| 11 | 97.1 | 2.9 | 33.5 | 74.5 | 82.8 | 80.4 | 0.7 | 114.9 | 3.43 |
| 12 | 97.2 | 2.8 | 34.7 | 11.0 | 99.6 | 96.8 | 2.5 | 38.7 | 1.12 |
| 13 | 97.2 | 2.8 | 34.7 | 1.8 | 99.3 | 96.5 | 2.7 | 35.7 | 1.03 |
| 14 | 97.1 | 2.9 | 33.5 | 5.6 | 98.6 | 95.7 | 2.7 | 35.4 | 1.06 |
| 15 | 97.5 | 2.5 | 39.0 | 4.3 | 98.3 | 95.8 | 2.4 | 39.9 | 1.02 |
| 16 | 97.3 | 2.7 | 36.0 | 66.4 | 82.5 | 80.3 | 0.9 | 89.2 | 2.48 |
| 17 | 97.1 | 2.9 | 33.5 | 8.2 | 98.3 | 95.4 | 2.7 | 35.3 | 1.05 |
| 18 | 97.2 | 2.8 | 34.7 | 5.0 | 98.7 | 95.9 | 2.7 | 35.5 | 1.02 |
| 19 | 97.2 | 2.8 | 34.7 | 3.5 | 98.7 | 95.9 | 2.7 | 35.5 | 1.02 |
| 20 | 97.6 | 2.4 | 40.7 | 11.2 | 91.3 | 89.1 | 2.1 | 42.4 | 1.04 |

TABLE 7

Filter Element of Example 5

| | | | | 96.5 g/L Challenge Load | | | | | |
|---|---|---|---|---|---|---|---|---|---|
| | | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 97.3 | 2.7 | 36.0 | 46.7 | 92.2 | 89.7 | 1.4 | 64.1 | 1.78 |
| 2 | 97.3 | 2.7 | 36.0 | 73.0 | 83.4 | 81.1 | 0.7 | 115.8 | 3.22 |
| 3 | 97.2 | 2.8 | 34.7 | 72.6 | 84.0 | 81.6 | 0.8 | 102.0 | 2.94 |
| 4 | 97.4 | 2.6 | 37.5 | 77.6 | 86.4 | 84.2 | 0.6 | 140.3 | 3.74 |
| 5 | 97.5 | 2.5 | 39.0 | 30.5 | 97.6 | 95.2 | 1.7 | 56.0 | 1.43 |
| 6 | 97.3 | 2.7 | 36.0 | 75.4 | 77.4 | 75.3 | 0.7 | 107.6 | 2.99 |
| 7 | 97.2 | 2.8 | 34.7 | 92.8 | 82.2 | 79.9 | 0.2 | 399.5 | 11.51 |
| 8 | 97.4 | 2.6 | 37.5 | 59.9 | 95.3 | 92.8 | 1.0 | 92.8 | 2.47 |
| 9 | 97.5 | 2.5 | 39.0 | 30.4 | 98.1 | 95.6 | 1.7 | 56.2 | 1.44 |
| 10 | 97.5 | 2.5 | 39.0 | 11.4 | 98.4 | 95.9 | 2.2 | 43.6 | 1.11 |
| 11 | 97.1 | 2.9 | 33.5 | 96.6 | 77.7 | 75.4 | 0.1 | 754.0 | 22.51 |
| 12 | 97.2 | 2.8 | 34.7 | 36.1 | 87.4 | 85.0 | 1.8 | 47.2 | 1.36 |
| 13 | 97.2 | 2.8 | 34.7 | 15.1 | 98.9 | 96.1 | 2.4 | 40.0 | 1.15 |
| 14 | 97.1 | 2.9 | 33.5 | 13.7 | 98.3 | 95.4 | 2.5 | 38.2 | 1.14 |
| 15 | 97.5 | 2.5 | 39.0 | 18.2 | 96.7 | 94.3 | 2.0 | 47.1 | 1.21 |
| 16 | 97.3 | 2.7 | 36.0 | 89.4 | 79.3 | 77.2 | 0.3 | 257.3 | 7.15 |
| 17 | 97.1 | 2.9 | 33.5 | 13.5 | 98.8 | 95.9 | 2.5 | 38.4 | 1.15 |
| 18 | 97.2 | 2.8 | 34.7 | 4.0 | 99.5 | 96.7 | 2.7 | 35.8 | 1.03 |
| 19 | 97.2 | 2.8 | 34.7 | 6.7 | 98.7 | 95.9 | 2.6 | 36.9 | 1.06 |

TABLE 8

Filter Element of Example 6

| | | | | 386 g/L Challenge Load | | | | | |
|---|---|---|---|---|---|---|---|---|---|
| | | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 97.1 | 2.9 | 33.5 | 88.8 | 81.9 | 79.5 | 0.3 | 265.0 | 7.91 |
| 2 | 97.1 | 2.9 | 33.5 | 89.8 | 84.7 | 82.2 | 0.3 | 274.0 | 8.18 |
| 3 | 97.0 | 3.0 | 32.3 | 60.7 | 91.8 | 89.0 | 1.2 | 74.2 | 2.30 |
| 4 | 97.2 | 2.8 | 34.7 | 25.0 | 97.5 | 94.8 | 2.1 | 45.1 | 1.30 |
| 5 | 97.2 | 2.8 | 34.7 | 5.3 | 98.2 | 95.5 | 2.7 | 35.4 | 1.02 |
| 6 | 97.0 | 3.0 | 32.3 | 80.5 | 81.1 | 78.7 | 0.6 | 131.2 | 4.06 |
| 7 | 96.9 | 3.1 | 31.3 | 68.4 | 93.9 | 91.0 | 1.0 | 91.0 | 2.91 |
| 8 | 97.0 | 3.0 | 32.3 | 13.8 | 98.5 | 95.5 | 2.6 | 36.7 | 1.14 |
| 9 | 97.2 | 2.8 | 34.7 | 5.7 | 98.5 | 95.7 | 2.6 | 36.8 | 1.06 |
| 10 | 97.3 | 2.7 | 36.0 | 4.0 | 98.8 | 96.1 | 2.6 | 37.0 | 1.03 |
| 11 | 96.8 | 3.2 | 30.3 | 76.8 | 82.5 | 79.9 | 0.7 | 114.1 | 3.76 |
| 12 | 96.8 | 3.2 | 30.3 | 10.4 | 98.4 | 95.3 | 2.9 | 32.9 | 1.09 |
| 13 | 96.9 | 3.1 | 31.3 | 5.6 | 99.2 | 96.1 | 2.9 | 33.1 | 1.06 |
| 14 | 96.9 | 3.1 | 31.3 | 4.0 | 99.3 | 96.2 | 3.0 | 32.1 | 1.02 |
| 15 | 97.2 | 2.8 | 34.7 | 3.8 | 99.4 | 96.6 | 2.7 | 35.8 | 1.03 |
| 16 | 96.8 | 3.2 | 30.3 | 53.5 | 57.9 | 56.0 | 1.5 | 37.3 | 1.23 |
| 17 | 96.8 | 3.2 | 30.3 | 4.5 | 99.4 | 96.2 | 3.1 | 31.0 | 1.02 |
| 18 | 96.8 | 3.2 | 30.3 | 43.6 | 60.2 | 58.3 | 1.8 | 32.4 | 1.07 |
| 19 | 96.8 | 3.2 | 30.3 | 2.7 | 99.8 | 96.6 | 3.1 | 31.2 | 1.03 |
| 20 | 97.3 | 2.7 | 36.0 | 0.3 | 100 | 97.3 | 2.7 | 36.0 | 1.00 |

TABLE 9

Filter Element of Example 7

386 g/L Challenge Load

| IgG Solution Number | Initial Monomeric IgG (%) | Initial Aggregated IgG (%) | Initial Composition Ratio | Filtration Performance | | Final Monomeric IgG Recovered (%) | Final Aggregated IgG Recovered (%) | Final Composition Ratio | Ratio of Final Composition Ratio to Initial Composition Ratio |
|---|---|---|---|---|---|---|---|---|---|
| | | | | Aggregated IgG Removed (%) | Monomeric IgG Yield (%) | | | | |
| 1 | 96.4 | 3.6 | 26.8 | 55.2 | 86.5 | 83.4 | 1.6 | 52.1 | 1.94 |
| 2 | 97.1 | 2.9 | 33.5 | 69.8 | 82.4 | 80.0 | 0.9 | 88.9 | 2.65 |
| 3 | 96.7 | 3.3 | 29.3 | 82.4 | 85.5 | 82.7 | 0.6 | 137.8 | 4.70 |
| 4 | 96.9 | 3.1 | 31.3 | 68.0 | 94.0 | 91.1 | 1.0 | 91.1 | 2.91 |
| 6 | 96.8 | 3.2 | 30.3 | 65.6 | 75.3 | 72.9 | 1.1 | 66.3 | 2.19 |
| 7 | 96.5 | 3.5 | 27.6 | 87.0 | 85.2 | 82.2 | 0.5 | 164.4 | 5.96 |
| 8 | 95.3 | 4.7 | 20.3 | 21.6 | 98.6 | 94.0 | 3.7 | 25.4 | 1.26 |
| 9 | 97.3 | 2.7 | 36.0 | 8.8 | 99.1 | 96.4 | 2.5 | 38.6 | 1.07 |
| 11 | 95.6 | 4.4 | 21.7 | 90.5 | 79.5 | 76.0 | 0.4 | 190.0 | 8.75 |
| 12 | 94.9 | 5.1 | 18.6 | 12.1 | 99.2 | 94.1 | 4.5 | 20.9 | 1.12 |
| 13 | 97.1 | 2.9 | 33.5 | 1.9 | 99.5 | 96.6 | 2.8 | 34.5 | 1.03 |
| 14 | 96.5 | 3.5 | 27.6 | 1.1 | 99.7 | 96.2 | 3.5 | 27.5 | 1.00 |
| 16 | 94.7 | 5.3 | 17.9 | 80.4 | 83.9 | 79.5 | 1.0 | 79.5 | 4.44 |
| 17 | 94.6 | 5.4 | 17.5 | 3.8 | 99.0 | 93.7 | 5.2 | 18.0 | 1.03 |
| 18 | 94.7 | 5.3 | 17.9 | 1.6 | 99.6 | 94.3 | 5.2 | 18.1 | 1.01 |
| 19 | 96.1 | 3.9 | 24.6 | 2.0 | 99.4 | 95.5 | 3.8 | 25.1 | 1.02 |

TABLE 10

Filter Element of Example 8

386 g/L Challenge Load

| IgG Solution Number | Initial Monomeric IgG (%) | Initial Aggregated IgG (%) | Initial Composition Ratio | Filtration Performance | | Final Monomeric IgG Recovered (%) | Final Aggregated IgG Recovered (%) | Final Composition Ratio | Ratio of Final Composition Ratio to Initial Composition Ratio |
|---|---|---|---|---|---|---|---|---|---|
| | | | | Aggregated IgG Removed (%) | Monomeric IgG Yield (%) | | | | |
| 1 | 96.4 | 3.6 | 26.8 | 30.5 | 92.5 | 89.2 | 2.5 | 35.6 | 1.33 |
| 2 | 97.1 | 2.9 | 33.5 | 56.5 | 87.3 | 84.8 | 1.3 | 65.2 | 1.95 |
| 3 | 96.7 | 3.3 | 29.3 | 66.0 | 83.8 | 81.0 | 1.1 | 73.6 | 2.51 |
| 4 | 96.9 | 3.1 | 31.3 | 72.0 | 85.6 | 82.9 | 0.9 | 92.1 | 2.94 |
| 6 | 96.8 | 3.2 | 30.3 | 57.7 | 84.0 | 81.3 | 1.4 | 58.1 | 1.92 |
| 7 | 96.5 | 3.5 | 27.6 | 78.1 | 78.2 | 75.5 | 0.8 | 94.4 | 3.42 |
| 8 | 95.3 | 4.7 | 20.3 | 58.0 | 94.2 | 89.8 | 2.0 | 44.9 | 2.21 |
| 9 | 97.3 | 2.7 | 36.0 | 33.9 | 97.4 | 94.8 | 1.8 | 52.7 | 1.46 |
| 11 | 95.6 | 4.4 | 21.7 | 85.9 | 72.8 | 69.6 | 0.6 | 116.0 | 5.35 |
| 12 | 94.9 | 5.1 | 18.6 | 26.8 | 97.8 | 92.8 | 3.7 | 25.1 | 1.35 |
| 13 | 97.1 | 2.9 | 33.5 | 8.6 | 99.3 | 96.4 | 2.7 | 35.7 | 1.06 |
| 14 | 96.5 | 3.5 | 27.6 | 5.0 | 99.6 | 96.1 | 3.3 | 29.1 | 1.05 |
| 16 | 94.7 | 5.3 | 17.9 | 82.9 | 79.5 | 75.3 | 0.9 | 83.7 | 4.68 |
| 17 | 94.6 | 5.4 | 17.5 | 8.0 | 98.8 | 93.5 | 5.0 | 18.7 | 1.07 |
| 18 | 94.7 | 5.3 | 17.9 | 3.5 | 99.2 | 93.9 | 5.1 | 18.4 | 1.03 |
| 19 | 96.1 | 3.9 | 24.6 | 2.1 | 99.2 | 95.3 | 3.8 | 25.1 | 1.02 |

TABLE 11

Filter Element of Example 9

| | | | 386 g/L Challenge Load | | | | | |
| --- | --- | --- | --- | --- | --- | --- | --- | --- |
| | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 96.4 | 3.6 | 26.8 | 57.9 | 88.0 | 84.8 | 1.5 | 56.5 | 2.11 |
| 2 | 97.1 | 2.9 | 33.5 | 70.0 | 86.4 | 83.9 | 0.9 | 93.2 | 2.78 |
| 3 | 96.7 | 3.3 | 29.3 | 70.1 | 87.3 | 84.4 | 1.0 | 84.4 | 2.88 |
| 4 | 96.9 | 3.1 | 31.3 | 68.3 | 90.2 | 87.4 | 1.0 | 87.4 | 2.79 |
| 6 | 96.8 | 3.2 | 30.3 | 70.6 | 71.8 | 69.5 | 0.9 | 77.2 | 2.55 |
| 7 | 96.5 | 3.5 | 27.6 | 82.7 | 82.2 | 79.3 | 0.6 | 132.2 | 4.79 |
| 8 | 95.3 | 4.7 | 20.3 | 27.6 | 97.6 | 93.0 | 3.4 | 27.3 | 1.35 |
| 9 | 97.3 | 2.7 | 36.0 | 14.3 | 98.6 | 95.9 | 2.3 | 41.7 | 1.16 |
| 11 | 95.6 | 4.4 | 21.7 | 90.1 | 76.0 | 72.7 | 0.4 | 181.7 | 8.37 |
| 12 | 94.9 | 5.1 | 18.6 | 11.1 | 98.4 | 93.4 | 4.5 | 20.8 | 1.12 |
| 13 | 97.1 | 2.9 | 33.5 | 3.0 | 99.0 | 96.1 | 2.8 | 34.3 | 1.02 |
| 14 | 96.5 | 3.5 | 27.6 | 1.8 | 99.3 | 95.8 | 3.4 | 28.2 | 1.02 |
| 16 | 94.7 | 5.3 | 17.9 | 78.1 | 81.8 | 77.5 | 1.2 | 64.6 | 3.59 |
| 17 | 94.6 | 5.4 | 17.5 | 3.3 | 99.1 | 93.7 | 5.2 | 18.0 | 1.02 |
| 18 | 94.7 | 5.3 | 17.9 | 2.2 | 99.8 | 94.5 | 5.2 | 18.2 | 1.02 |
| 19 | 96.1 | 3.9 | 24.6 | 2.0 | 99.8 | 95.9 | 3.8 | 25.2 | 1.02 |

TABLE 12

Filter Element of Example 10

| | | | 386 g/L Challenge Load | | | | | |
| --- | --- | --- | --- | --- | --- | --- | --- | --- |
| | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 96.4 | 3.6 | 26.8 | 36.5 | 91.9 | 88.6 | 2.3 | 38.5 | 1.44 |
| 2 | 97.3 | 2.7 | 36.0 | 56.2 | 89.5 | 87.1 | 1.2 | 72.6 | 2.02 |
| 3 | 96.7 | 3.3 | 29.3 | 59.1 | 86.2 | 83.4 | 1.3 | 64.2 | 2.19 |
| 4 | 96.9 | 3.1 | 31.3 | 64.1 | 84.8 | 82.2 | 1.1 | 74.7 | 2.39 |
| 6 | 96.9 | 3.1 | 31.3 | 65.0 | 77.4 | 75.0 | 1.1 | 68.2 | 2.18 |
| 7 | 96.5 | 3.5 | 27.6 | 80.8 | 70.2 | 67.7 | 0.7 | 96.7 | 3.50 |
| 8 | 95.2 | 4.8 | 19.8 | 66.9 | 91.3 | 86.9 | 1.6 | 54.3 | 2.74 |
| 9 | 97.3 | 2.7 | 36.0 | 42.5 | 97.1 | 94.5 | 1.6 | 59.1 | 1.64 |
| 11 | 95.7 | 4.3 | 22.3 | 84.9 | 69.5 | 66.5 | 0.6 | 110.8 | 4.97 |
| 12 | 94.9 | 5.1 | 18.6 | 23.0 | 98.0 | 93.0 | 3.9 | 23.8 | 1.28 |
| 13 | 97.2 | 2.8 | 34.7 | 7.3 | 99.5 | 96.7 | 2.6 | 37.2 | 1.07 |
| 14 | 96.5 | 3.5 | 27.6 | 4.9 | 99.7 | 96.2 | 3.3 | 29.2 | 1.06 |
| 16 | 94.7 | 5.3 | 17.9 | 82.7 | 73.7 | 69.8 | 0.9 | 77.5 | 4.33 |
| 17 | 94.6 | 5.4 | 17.5 | 7.1 | 98.8 | 93.5 | 5.0 | 18.7 | 1.07 |
| 18 | 94.7 | 5.3 | 17.9 | 3.1 | 99.8 | 94.5 | 5.1 | 18.5 | 1.03 |
| 19 | 96.1 | 3.9 | 24.6 | 4.0 | 99.8 | 95.9 | 3.7 | 25.9 | 1.05 |

TABLE 13

Filter Element of Example 11

386 g/L Challenge Load

| IgG Solution Number | Initial Monomeric IgG (%) | Initial Aggregated IgG (%) | Initial Composition Ratio | Filtration Performance | | Final Monomeric IgG Recovered (%) | Final Aggregated IgG Recovered (%) | Final Composition Ratio | Ratio of Final Composition Ratio to Initial Composition Ratio |
|---|---|---|---|---|---|---|---|---|---|
| | | | | Aggregated IgG Removed (%) | Monomeric IgG Yield (%) | | | | |
| 1 | 96.4 | 3.6 | 26.8 | 39.6 | 92.9 | 89.6 | 2.2 | 40.7 | 1.52 |
| 2 | 97.2 | 2.8 | 34.7 | 60.6 | 94.2 | 91.6 | 1.1 | 83.3 | 2.40 |
| 3 | 96.7 | 3.3 | 29.3 | 68.1 | 95.5 | 92.3 | 1.1 | 83.9 | 2.86 |
| 4 | 96.9 | 3.1 | 31.3 | 53.0 | 97.4 | 94.4 | 1.5 | 62.9 | 2.01 |
| 6 | 96.8 | 3.2 | 30.3 | 49.7 | 87.9 | 85.1 | 1.6 | 53.2 | 1.75 |
| 7 | 96.5 | 3.5 | 27.6 | 74.1 | 93.2 | 89.9 | 0.9 | 99.9 | 3.62 |
| 8 | 95.2 | 4.8 | 19.8 | 23.1 | 99.2 | 94.4 | 3.7 | 25.5 | 1.29 |
| 9 | 97.3 | 2.7 | 36.0 | 17.9 | 99.8 | 97.1 | 2.2 | 44.1 | 1.22 |
| 11 | 95.6 | 4.4 | 21.7 | 74.2 | 91.5 | 87.5 | 1.1 | 79.5 | 3.66 |
| 12 | 94.8 | 5.2 | 18.2 | 23.1 | 98.0 | 92.9 | 4.0 | 23.2 | 1.27 |
| 13 | 97.2 | 2.8 | 34.7 | 8.0 | 99.4 | 96.6 | 2.6 | 37.2 | 1.07 |
| 14 | 97.1 | 2.9 | 33.5 | 4.1 | 99.5 | 96.6 | 2.8 | 34.5 | 1.03 |
| 16 | 94.7 | 5.3 | 17.9 | 69.3 | 90.6 | 85.8 | 1.6 | 53.6 | 2.99 |
| 17 | 94.6 | 5.4 | 17.5 | 7.9 | 99.2 | 93.8 | 5.0 | 18.8 | 1.07 |
| 18 | 94.7 | 5.3 | 17.9 | 3.3 | 99.4 | 94.1 | 5.1 | 18.5 | 1.03 |
| 19 | 96.1 | 3.9 | 24.6 | 3.5 | 99.3 | 95.4 | 3.8 | 25.1 | 1.02 |

TABLE 14

Filter Element of Example 12

386 g/L Challenge Load

| IgG Solution Number | Initial Monomeric IgG (%) | Initial Aggregated IgG (%) | Initial Composition Ratio | Filtration Performance | | Final Monomeric IgG Recovered (%) | Final Aggregated IgG Recovered (%) | Final Composition Ratio | Ratio of Final Composition Ratio to Initial Composition Ratio |
|---|---|---|---|---|---|---|---|---|---|
| | | | | Aggregated IgG Removed (%) | Monomeric IgG Yield (%) | | | | |
| 1 | 96.4 | 3.6 | 26.8 | 48.0 | 95.7 | 92.3 | 1.9 | 48.6 | 1.81 |
| 2 | 97.2 | 2.8 | 34.7 | 61.1 | 95.9 | 93.2 | 1.1 | 84.7 | 2.44 |
| 3 | 96.7 | 3.3 | 29.3 | 59.0 | 95.5 | 92.3 | 1.4 | 65.9 | 2.25 |
| 4 | 96.9 | 3.1 | 31.3 | 39.6 | 98.4 | 95.3 | 1.9 | 50.2 | 1.60 |
| 6 | 96.8 | 3.2 | 30.3 | 70.2 | 81.4 | 78.8 | 1.0 | 78.8 | 2.60 |
| 7 | 96.5 | 3.5 | 27.6 | 71.7 | 93.0 | 89.7 | 1.0 | 89.7 | 3.25 |
| 8 | 95.2 | 4.8 | 19.8 | 6.2 | 99.4 | 94.6 | 4.5 | 21.0 | 1.06 |
| 9 | 97.3 | 2.7 | 36.0 | 3.9 | 99.3 | 96.6 | 2.6 | 37.2 | 1.03 |
| 11 | 95.6 | 4.4 | 21.7 | 80.5 | 90.3 | 86.3 | 0.9 | 95.9 | 4.42 |
| 12 | 94.8 | 5.2 | 18.2 | 7.3 | 99.1 | 93.9 | 4.8 | 19.6 | 1.08 |
| 13 | 97.2 | 2.8 | 34.7 | 4.7 | 99.0 | 96.2 | 2.7 | 35.6 | 1.03 |
| 14 | 97.1 | 2.9 | 33.5 | 3.2 | 99.2 | 96.3 | 2.8 | 34.3 | 1.02 |
| 16 | 94.7 | 5.3 | 17.9 | 67.9 | 89.4 | 84.7 | 1.7 | 49.8 | 2.78 |
| 17 | 94.6 | 5.4 | 17.5 | 3.1 | 99.5 | 94.1 | 5.2 | 18.1 | 1.03 |
| 18 | 94.7 | 5.3 | 17.9 | 2.6 | 99.5 | 94.2 | 5.2 | 18.1 | 1.01 |
| 19 | 96.1 | 3.9 | 24.6 | 5.2 | 99.2 | 95.3 | 3.7 | 25.8 | 1.05 |

TABLE 15

Filter Element of Example 13

| | | | | 387 g/L Challenge Load | | | | | |
|---|---|---|---|---|---|---|---|---|---|
| | | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 97.7 | 2.3 | 42.5 | 44.2 | 95.3 | 93.1 | 1.3 | 71.6 | 1.68 |
| 3 | 97.6 | 2.4 | 40.7 | 74.3 | 97.0 | 94.7 | 0.6 | 157.8 | 3.88 |
| 4 | 97.5 | 2.5 | 39.0 | 70.9 | 99.3 | 96.8 | 0.7 | 138.3 | 3.55 |
| 6 | 97.5 | 2.5 | 39.0 | 49.2 | 87.3 | 85.1 | 1.3 | 65.5 | 1.68 |
| 7 | 97.5 | 2.5 | 39.0 | 81.3 | 94.2 | 91.8 | 0.5 | 183.6 | 4.71 |
| 8 | 97.6 | 2.4 | 40.7 | 48.8 | 100.6 | 98.2 | 1.2 | 81.8 | 2.01 |
| 9 | 97.5 | 2.5 | 39.0 | 33.1 | 100.1 | 97.6 | 1.7 | 57.4 | 1.47 |
| 11 | 96.1 | 3.9 | 24.6 | 87.0 | 84.6 | 81.3 | 0.5 | 162.6 | 6.61 |
| 12 | 96.9 | 3.1 | 31.3 | 34.5 | 100.3 | 97.2 | 2.0 | 48.6 | 1.55 |
| 14 | 97.3 | 2.7 | 36.0 | 0.2 | 102.1 | 99.3 | 2.7 | 36..8 | 1.02 |
| 16 | 97.2 | 2.8 | 34.7 | 87.8 | 87.2 | 84.8 | 0.3 | 282.7 | 8.15 |
| 17 | 97.1 | 2.9 | 33.5 | 5.4 | 100.1 | 97.2 | 2.7 | 36.0 | 1.07 |
| 18 | 97.1 | 2.9 | 33.5 | 4.1 | 100.3 | 97.4 | 2.8 | 34.8 | 1.04 |

TABLE 16

Filter Element of Example 14

| | | | | 386 g/L Challenge Load | | | | | |
|---|---|---|---|---|---|---|---|---|---|
| | | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 97.7 | 2.3 | 42.5 | 70.5 | 86.3 | 84.3 | 0.7 | 120.4 | 2.83 |
| 3 | 97.6 | 2.4 | 40.7 | 81.6 | 81.5 | 79.5 | 0.4 | 198.7 | 4.88 |
| 4 | 97.5 | 2.5 | 39.0 | 73.2 | 97.3 | 94.9 | 0.7 | 135.6 | 3.48 |
| 6 | 97.5 | 2.5 | 39.0 | 65.7 | 72.4 | 70.6 | 0.9 | 78.4 | 2.01 |
| 7 | 97.5 | 2.5 | 39.0 | 85.2 | 77.9 | 76.0 | 0.4 | 190.0 | 4.87 |
| 8 | 97.6 | 2.4 | 40.7 | 54.2 | 99.0 | 96.6 | 1.1 | 87.8 | 2.16 |
| 9 | 97.5 | 2.5 | 39.0 | 20.3 | 99.9 | 97.4 | 2.0 | 48.7 | 1.25 |
| 11 | 96.1 | 3.9 | 24.6 | 87.8 | 72.9 | 70.1 | 0.5 | 140.2 | 5.70 |
| 12 | 96.9 | 3.1 | 31.3 | 23.8 | 100.2 | 97.1 | 2.4 | 40.5 | 1.29 |
| 14 | 97.3 | 2.7 | 36.0 | -4.7 | 102.1 | 99.3 | 2.8 | 35.5 | 0.99 |
| 16 | 97.2 | 2.8 | 34.7 | 77.6 | 85.3 | 82.9 | 0.6 | 138.2 | 3.98 |
| 17 | 97.1 | 2.9 | 33.5 | 2.3 | 100.1 | 97.2 | 2.8 | 34.7 | 1.04 |
| 18 | 97.1 | 2.9 | 33.5 | 3.4 | 100.2 | 97.3 | 2.8 | 34.8 | 1.04 |

TABLE 17

| | | | Filter Element of Comparative Example A | | | | | |
|---|---|---|---|---|---|---|---|---|
| | | | 387 g/L Challenge Load | | | | | |
| | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
|---|---|---|---|---|---|---|---|---|---|
| 1 | 97.5 | 2.5 | 39.0 | 93.9 | 85.6 | 83.5 | 0.2 | 417.5 | 10.70 |
| 2 | 97.6 | 2.4 | 40.7 | 93.7 | 86.0 | 83.9 | 0.2 | 419.5 | 10.30 |
| 3 | 96.9 | 3.1 | 31.3 | 46.6 | 95.9 | 92.9 | 1.7 | 54.6 | 1.74 |
| 4 | 97.1 | 2.9 | 33.5 | 17.0 | 98.7 | 95.8 | 2.4 | 39.9 | 1.19 |
| 6 | 97.0 | 3.0 | 32.3 | 74.1 | 87.2 | 84.6 | 0.8 | 105.7 | 3.27 |
| 7 | 96.8 | 3.2 | 30.3 | 50.1 | 96.2 | 93.1 | 1.6 | 58.2 | 1.92 |
| 8 | 99.0 | 1.0 | 99.0 | 2.7 | 98.6 | 97.6 | 1.0 | 97.6 | 0.98 |
| 9 | 97.3 | 2.7 | 36.0 | 7.9 | 99.9 | 97.2 | 2.5 | 38.9 | 1.08 |
| 11 | 96.1 | 3.9 | 24.6 | 71.2 | 88.4 | 85.0 | 1.1 | 77.3 | 3.14 |
| 12 | 96.3 | 3.7 | 26.0 | 14.3 | 99.9 | 96.2 | 3.2 | 30.1 | 1.16 |
| 13 | 96.4 | 3.6 | 26.8 | 11.1 | 99.2 | 95.6 | 3.2 | 29.9 | 1.12 |
| 14 | 96.4 | 3.6 | 26.8 | 7.9 | 99.3 | 95.7 | 3.3 | 29.0 | 1.08 |
| 16 | 96.3 | 3.7 | 26.0 | 52.1 | 95.3 | 91.8 | 1.8 | 51.0 | 1.96 |
| 17 | 96.2 | 3.8 | 25.3 | 8.2 | 99.7 | 95.9 | 3.5 | 27.4 | 1.08 |
| 18 | 96.2 | 3.8 | 25.3 | 9.9 | 98.7 | 94.9 | 3.4 | 27.9 | 1.10 |
| 19 | 96.4 | 3.6 | 26.8 | 6.8 | 98.9 | 95.3 | 3.4 | 28.0 | 1.04 |

TABLE 18

| | | | Filter Element of Comparative Example B | | | | | |
|---|---|---|---|---|---|---|---|---|
| | | | 96.5 g/L Challenge Load | | | | | |
| | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
|---|---|---|---|---|---|---|---|---|---|
| 1 | 97.1 | 2.9 | 33.5 | 18.8 | 90.4 | 87.8 | 2.4 | 36.6 | 1.09 |
| 2 | 97.0 | 3.0 | 32.3 | 23.0 | 92.1 | 89.3 | 2.3 | 38.8 | 1.20 |
| 3 | 96.5 | 3.5 | 27.6 | 29.5 | 90.6 | 87.4 | 2.5 | 35.0 | 1.27 |
| 4 | 96.8 | 3.2 | 30.3 | 31.5 | 91.4 | 88.5 | 2.2 | 40.2 | 1.33 |
| 6 | 96.6 | 3.4 | 28.4 | 55.7 | 79.7 | 77.0 | 1.5 | 51.3 | 1.81 |
| 7 | 96.4 | 3.6 | 26.8 | 80.0 | 76.3 | 73.6 | 0.7 | 105.1 | 3.92 |
| 8 | 98.1 | 1.9 | 51.6 | 23.6 | 95.7 | 93.9 | 1.5 | 62.6 | 1.21 |
| 9 | 96.9 | 3.1 | 31.3 | 7.8 | 97.9 | 94.9 | 2.9 | 32.7 | 1.04 |
| 11 | 95.7 | 4.3 | 22.3 | 48.6 | 88.4 | 84.6 | 2.2 | 38.4 | 1.72 |
| 12 | 96.3 | 3.7 | 26.0 | 9.3 | 99.7 | 96.0 | 3.4 | 28.2 | 1.08 |
| 13 | 95.9 | 4.1 | 23.4 | 8.3 | 98.5 | 94.5 | 3.8 | 24.9 | 1.06 |
| 14 | 96.0 | 4.0 | 24.0 | 7.1 | 99.5 | 95.5 | 3.7 | 25.8 | 1.07 |
| 17 | 95.8 | 4.2 | 22.8 | 6.5 | 98.6 | 94.5 | 3.9 | 24.2 | 1.06 |
| 18 | 95.7 | 4.3 | 22.3 | 4.9 | 98.0 | 93.8 | 4.1 | 22.9 | 1.03 |
| 19 | 95.9 | 4.1 | 23.4 | 6.9 | 98.8 | 94.7 | 3.8 | 24.9 | 1.06 |

TABLE 19

Filter Element of Comparative Example C

| | | | | 386 g/L Challenge Load | | | | | |
|---|---|---|---|---|---|---|---|---|---|
| | | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 96.4 | 3.6 | 26.8 | 10.7 | 92.7 | 89.4 | 3.2 | 27.9 | 1.04 |
| 2 | 97.1 | 2.9 | 33.5 | 8.0 | 92.5 | 89.8 | 2.7 | 33.3 | 0.99 |
| 3 | 96.7 | 3.3 | 29.3 | 14.5 | 93.8 | 90.7 | 2.8 | 32.4 | 1.10 |
| 4 | 96.9 | 3.1 | 31.3 | 19.2 | 93.3 | 90.4 | 2.5 | 36.2 | 1.15 |
| 6 | 96.8 | 3.2 | 30.3 | 22.1 | 93.1 | 90.1 | 2.5 | 36.0 | 1.19 |
| 7 | 96.5 | 3.5 | 27.6 | 48.5 | 83.9 | 81.0 | 1.8 | 45.0 | 1.63 |
| 8 | 95.3 | 4.7 | 20.3 | 66.7 | 76.6 | 73.0 | 1.6 | 45.6 | 2.25 |
| 9 | 97.3 | 2.7 | 36.0 | 71.4 | 80.1 | 77.9 | 0.8 | 97.4 | 2.71 |
| 11 | 95.6 | 4.4 | 21.7 | 71.9 | 63.0 | 60.2 | 1.2 | 50.2 | 2.31 |
| 12 | 94.9 | 5.1 | 18.6 | 75.0 | 86.3 | 81.9 | 1.3 | 63.0 | 3.39 |
| 13 | 97.1 | 2.9 | 33.5 | 36.3 | 95.4 | 92.6 | 1.8 | 51.4 | 1.53 |
| 14 | 96.5 | 3.5 | 27.6 | 17.7 | 98.7 | 95.2 | 2.9 | 32.8 | 1.19 |
| 16 | 94.7 | 5.3 | 17.9 | 81.8 | 68.5 | 64.9 | 1.0 | 64.9 | 3.62 |
| 17 | 94.6 | 5.4 | 17.5 | 22.6 | 97.1 | 91.9 | 4.2 | 21.9 | 1.25 |
| 18 | 94.7 | 5.3 | 17.9 | 7.6 | 99.5 | 94.2 | 4.9 | 19.2 | 1.07 |
| 19 | 96.1 | 3.9 | 24.6 | 6.5 | 99.9 | 96.0 | 3.6 | 26.7 | 1.08 |

TABLE 20

Filter Element of Comparative Example D

| | | | | 386 g/L Challenge Load | | | | | |
|---|---|---|---|---|---|---|---|---|---|
| | | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 97.5 | 2.5 | 39.0 | 10.8 | 91.9 | 89.6 | 2.2 | 40.7 | 1.04 |
| 2 | 97.6 | 2.4 | 40.7 | 5.9 | 93.3 | 91.1 | 2.3 | 39.6 | 0.97 |
| 3 | 97.4 | 2.6 | 37.5 | 21.1 | 94.2 | 91.8 | 2.1 | 43.7 | 1.17 |
| 4 | 97.3 | 2.7 | 36.0 | 33.3 | 95.1 | 92.5 | 1.8 | 51.4 | 1.42 |
| 5 | 97.4 | 2.6 | 37.5 | 29.9 | 97.2 | 94.7 | 1.8 | 52.6 | 1.40 |
| 6 | 97.2 | 2.8 | 34.7 | 17.2 | 92.2 | 89.6 | 2.3 | 38.9 | 1.12 |
| 7 | 97.0 | 3.0 | 32.3 | 38.3 | 91.0 | 88.3 | 1.9 | 46.5 | 1.44 |
| 8 | 97.0 | 3.0 | 32.3 | 46.8 | 93.9 | 91.1 | 1.6 | 56.9 | 1.76 |
| 9 | 97.1 | 2.9 | 33.5 | 43.0 | 96.4 | 93.6 | 1.7 | 55.0 | 1.64 |
| 10 | 97.4 | 2.6 | 37.5 | 21.2 | 98.4 | 95.8 | 2.0 | 47.9 | 1.28 |
| 11 | 96.8 | 3.2 | 30.3 | 57.4 | 87.2 | 84.4 | 1.4 | 60.3 | 1.99 |
| 12 | 96.6 | 3.4 | 28.4 | 69.0 | 93.3 | 90.1 | 1.1 | 81.9 | 2.88 |
| 13 | 96.8 | 3.2 | 30.3 | 41.5 | 97.9 | 94.8 | 1.9 | 49.9 | 1.65 |
| 14 | 96.9 | 3.1 | 31.3 | 21.9 | 98.5 | 95.4 | 2.4 | 39.8 | 1.27 |
| 15 | 97.3 | 2.7 | 36.0 | 10.3 | 98.9 | 96.2 | 2.4 | 40.1 | 1.11 |
| 16 | 96.7 | 3.3 | 29.3 | 86.4 | 81.4 | 78.7 | 0.4 | 196.7 | 6.71 |
| 17 | 96.7 | 3.3 | 29.3 | 43.3 | 97.4 | 94.2 | 1.9 | 49.6 | 1.69 |
| 18 | 96.7 | 3.3 | 29.3 | 21.0 | 98.8 | 95.5 | 2.6 | 36.7 | 1.25 |
| 19 | 96.7 | 3.3 | 29.3 | 10.0 | 99.2 | 95.9 | 3.0 | 32.0 | 1.09 |
| 20 | 97.2 | 2.8 | 34.7 | 5.5 | 98.9 | 96.1 | 2.6 | 37.0 | 1.07 |

TABLE 21

Filter Element of Comparative Example E

| | | | | 386 g/L Challenge Load | | | | | |
|---|---|---|---|---|---|---|---|---|---|
| | | | | Filtration Performance | | Final | Final | | |
| IgG Solution Number | Initial Monomeric IgG (%) | Initial Aggregated IgG (%) | Initial Composition Ratio | Aggregated IgG Removed (%) | Monomeric IgG Yield (%) | Monomeric IgG Recovered (%) | Aggregated IgG Recovered (%) | Final Composition Ratio | Ratio of Final Composition Ratio to Initial Composition Ratio |
| 1 | 96.6 | 3.4 | 28.4 | 68.3 | 73.1 | 70.6 | 1.1 | 64.2 | 2.26 |
| 2 | 96.8 | 3.2 | 30.3 | 83.8 | 78.2 | 75.7 | 0.5 | 151.4 | 5.00 |
| 3 | 96.7 | 3.3 | 29.3 | 80.7 | 90.0 | 87.0 | 0.6 | 145.0 | 4.95 |
| 4 | 96.8 | 3.2 | 30.3 | 11.9 | 98.3 | 95.2 | 2.8 | 34.0 | 1.12 |
| 6 | 96.8 | 3.2 | 30.3 | 73.3 | 70.9 | 68.6 | 0.9 | 76.2 | 2.51 |
| 7 | 96.4 | 3.6 | 26.8 | 76.2 | 91.5 | 88.2 | 0.9 | 98.0 | 3.66 |
| 8 | 95.1 | 4.9 | 19.4 | 6.3 | 97.2 | 92.4 | 4.6 | 20.1 | 1.04 |
| 9 | 97.1 | 2.9 | 33.5 | 3.2 | 99.1 | 96.2 | 2.8 | 34.3 | 1.02 |
| 11 | 95.8 | 4.2 | 22.8 | 92.5 | 80.6 | 77.2 | 0.3 | 257.3 | 11.29 |
| 12 | 95.1 | 4.9 | 19.4 | 5.7 | 97.4 | 92.6 | 4.6 | 20.1 | 1.04 |
| 13 | 96.4 | 3.6 | 26.8 | 2.2 | 99.2 | 95.6 | 3.5 | 27.3 | 1.02 |
| 14 | 96.2 | 3.8 | 25.3 | 0.9 | 99.4 | 95.6 | 3.8 | 25.1 | 0.99 |
| 16 | 95.2 | 4.8 | 19.8 | 74.8 | 87.8 | 83.6 | 1.2 | 69.6 | 3.52 |
| 17 | 95.1 | 4.9 | 19.4 | 1.9 | 99.4 | 94.5 | 4.8 | 19.7 | 1.01 |
| 18 | 95.1 | 4.9 | 19.4 | 1.3 | 99.3 | 94.4 | 4.8 | 19.7 | 1.01 |
| 19 | 96.0 | 4.0 | 24.0 | 1.8 | 99.7 | 95.7 | 3.9 | 24.5 | 1.02 |

The referenced descriptions contained in the patents, patent documents, and publications cited herein are incorporated by reference in their entirety as if each were individually incorporated. Various unforeseeable modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only, with the scope of the disclosure intended to be limited only by the claims set forth herein as follows.

We claim:

1. An article comprising:
   a) a porous substrate; and
   b) a copolymer covalently attached to the porous substrate, the copolymer comprising a hydrocarbon backbone and a plurality of pendant groups attached to the hydrocarbon backbone, wherein:
   1) each of a first plurality of pendant groups comprises:
      (a) at least one acidic group or salt thereof; and
      (b) a spacer group that directly links the at least one acidic group or salt thereof to the hydrocarbon backbone by a chain of at least 6 catenated atoms; and
   2) each of a second plurality of pendant groups comprises:
      (a) at least one acidic group or salt thereof; and
      (b) a spacer group that directly links the at least one acidic group or salt thereof to the hydrocarbon backbone by a chain of at least 6 catenated atoms; and
   wherein the first plurality of pendant groups are different than the second plurality of pendant groups; and
   wherein a mole ratio of the first plurality of pendant groups to the second plurality of pendant groups is in a range of 95:5 to 5:95.

2. The article of claim 1 wherein the copolymer covalently attached to the porous substrate comprises a reaction product of a monomer composition comprising:
   1) A first monomer comprising:
      (a) at least one ethylenically unsaturated group;
      (b) at least one acidic group or salt thereof; and
      (c) a spacer group that directly links the at least one ethylenically unsaturated group and the at least one acidic group or salt thereof by a chain of at least 6 catenated atoms; and
   2) a second monomer comprising:
      (a) at least one ethylenically unsaturated group;
      (b) at least one acidic group or salt thereof; and
      (c) a spacer group that directly links the at least one ethylenically unsaturated group and the at least one acidic group by a chain of at least 6 catenated atoms;
   wherein the second monomer is different than the first monomer; and
   wherein a mole ratio of the first monomer to the second monomer is in a range of 95:5 to 5:95.

3. The article of claim 1 wherein the at least one acidic group or salt thereof of the copolymer covalently bonded to the porous substrate is present at a density of at least 0.01 mmole/gram of filter media.

4. The article of claim 1 wherein the at least one acidic group or salt thereof of the copolymer covalently bonded to the porous substrate is present at a density of up to 0.6 mmole/gram of filter media.

5. The article of claim 2 wherein the at least one ethylenically unsaturated group of the first monomer and/or second monomer is selected from an ethenyl group, a 1-alkylethenyl group, and a combination thereof.

6. The article of claim 1 wherein the spacer group is a catenated heteroatom-containing hydrocarbon group.

7. The article of claim 2 wherein the first monomer is one of a class represented by the following general formula:

$$CH_2=CR^1-C(=O)-X-R^2-[Z-R^2]_n-L \quad (I)$$

wherein:
- $R^1$ is selected from hydrogen, an alkyl group, a cycloalkyl group, an aryl group, and a combination thereof;
- each $R^2$ is independently selected from a hydrocarbylene group, a heterohydrocarbylene group, and a combination thereof;
- X is —O— or —NR$^3$—, where $R^3$ is selected from hydrogen, a hydrocarbyl group, a heterohydrocarbyl group, and a combination thereof;
- Z is a heterohydrocarbylene group comprising at least one hydrogen bond donor, at least one hydrogen bond acceptor, or a combination thereof;
- n is an integer of 0 or 1; and
- L is a functional group comprising at least one acidic group or salt thereof.

8. The article of claim 2 wherein the second monomer is one of a class represented by the following general formula:

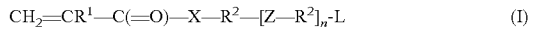

$$CH_2=CR^1-C(=O)-X-R^2-[Z-R^2]_n-L \quad (I)$$

wherein:
- $R^1$ is selected from hydrogen, an alkyl group, a cycloalkyl group, an aryl group, and a combination thereof;
- each $R^2$ is independently selected from a hydrocarbylene group, a heterohydrocarbylene group, and a combination thereof;
- X is —O— or —NR$^3$—, where $R^3$ is selected from hydrogen, a hydrocarbyl group, a heterohydrocarbyl group, and a combination thereof;
- Z is a heterohydrocarbylene group comprising at least one hydrogen bond donor, at least one hydrogen bond acceptor, or a combination thereof;
- n is an integer of 0 or 1; and
- L is a functional group comprising at least one acidic group or salt thereof.

9. The article of claim 1 which is a filter element having a contacting surface.

10. The article of claim 1 which is an array of sample containers, wherein each container includes the filter element having a contacting surface.

11. A process for capture or removal of a target biomaterial comprising:
- providing a filter element of claim 9; and
- allowing a biological solution comprising a target biomaterial to contact the contacting surface of the filter element under conditions effective for binding of the target biomaterial.

12. A process for separating aggregated proteins from monomeric proteins in a biological solution, the process comprising:
- providing at least one filter element having a contacting surface, wherein the filter element comprises filter media comprising:
  a) a porous substrate; and
  b) a copolymer covalently attached to the porous substrate, the copolymer comprising a hydrocarbon backbone and a plurality of pendant groups attached to the hydrocarbon backbone, wherein:
    1) Each of a first plurality of pendant groups comprises:
      (a) at least one acidic group or salt thereof; and
      (b) a spacer group that directly links the at least one acidic group or salt thereof to the hydrocarbon backbone by a chain of at least 6 catenated atoms; and
    2) each of a second plurality of pendant groups comprises:
      (a) at least one acidic group or salt thereof; and
      (b) a spacer group that directly links the at least one acidic group or salt thereof to the hydrocarbon backbone by a chain of at least 6 catenated atoms; and
  wherein the first plurality of pendant groups are different than the second plurality of pendant groups; and
  wherein a mole ratio of the first plurality of pendant groups to the second plurality of pendant groups is in a range of 95:5 to 5:95; and
- allowing an initial biological solution to contact the contacting surface of the filter element under conditions effective to separate the aggregated proteins from the monomeric proteins such that a final biological solution includes purified monomeric proteins.

13. The process of claim 12 wherein the copolymer covalently attached to the porous substrate comprises a reaction product of a monomer composition comprising
1) A first monomer comprising:
  (a) at least one ethylenically unsaturated group;
  (b) at least one acidic group or salt thereof; and
  (c) a spacer group that directly links the at least one ethylenically unsaturated group and the at least one acidic group or salt thereof by a chain of at least 6 catenated atoms; and
2) a second monomer comprising:
  (a) at least one ethylenically unsaturated group;
  (b) at least one acidic group or salt thereof; and
  (c) a spacer group that directly links the at least one ethylenically unsaturated group and the at least one acidic group or salt thereof by a chain of at least 6 catenated atoms;
wherein the second monomer is different than the first monomer; and
wherein a mole ratio of the first monomer to the second monomer is in a range of 95:5 to 5:95.

14. The process of claim 12 the conditions are effective to recover, in a final solution, at least 70% of the monomeric proteins present in the initial biological solution.

15. The process of claim 12 wherein the conditions are effective to remove at least 10% of the aggregated proteins from the initial biological solution.

* * * * *